(12) United States Patent
Meiri et al.

(10) Patent No.: US 10,130,464 B2
(45) Date of Patent: Nov. 20, 2018

(54) RETAINING MECHANISMS FOR PROSTHETIC VALVES

(71) Applicant: Edwards Lifesciences Corporation, Irvine, CA (US)

(72) Inventors: Oded Meiri, Moshav Ram-On (IL); Tamir S. Levi, Moshav Ein HaEmek (IL); Ofir Witzman, Kfar Saba (IL)

(73) Assignee: Edwards Lifesciences Corporation, Irvine, CA (US)

( * ) Notice: Subject to any disclaimer, the term of this patent is extended or adjusted under 35 U.S.C. 154(b) by 250 days.

(21) Appl. No.: 15/164,306

(22) Filed: May 25, 2016

(65) Prior Publication Data

US 2016/0262879 A1    Sep. 15, 2016

Related U.S. Application Data

(63) Continuation of application No. 13/794,311, filed on Mar. 11, 2013, now Pat. No. 9,370,420, which is a
(Continued)

(51) Int. Cl.
*A61F 2/24* (2006.01)
*A61B 17/04* (2006.01)
(Continued)

(52) U.S. Cl.
CPC ........ *A61F 2/2409* (2013.01); *A61B 17/0487* (2013.01); *A61B 17/122* (2013.01); *A61B 17/12013* (2013.01); *A61B 17/1227* (2013.01); *A61B 17/1285* (2013.01); *A61F 2/2418* (2013.01); *A61F 2/2427* (2013.01);
(Continued)

(58) Field of Classification Search
CPC ............ A61F 2/2427; A61F 2220/0016; A61F 2230/0054; A61F 2250/006; A61F 2/2418; A61F 2/2433; A61F 2/2436; A61B 17/0487; A61B 17/12013; A61B 17/122;
(Continued)

(56) References Cited

U.S. PATENT DOCUMENTS 3,657,744 A    4/1972    Ersek
4,035,849 A    7/1977    Angell et al.
(Continued)

FOREIGN PATENT DOCUMENTS

DE    19532846 A1    3/1997
DE    19907646 A1    8/2000
(Continued)

*Primary Examiner* — Julian W Woo
(74) *Attorney, Agent, or Firm* — Thomas C. Richardson

(57) ABSTRACT

Embodiments of methods, apparatus, and systems used to deliver a prosthetic heart valve to a deficient valve. In one embodiment, for instance, a support member is positioned to at least partially surround the native leaflets of a valve. A locking member is used to couple both ends of the support member, forming a support band. An expandable prosthetic heart valve is delivered into the native heart valve and expanded while the expandable prosthetic valve is at least partially within the support band, thereby causing one or more of the native leaflets of the native heart valve to be frictionally secured between the support band and the expanded prosthetic heart valve.

12 Claims, 35 Drawing Sheets

Related U.S. Application Data continuation of application No. 13/042,160, filed on Mar. 7, 2011, now Pat. No. 8,398,708.

(60) Provisional application No. 61/311,143, filed on Mar. 5, 2010.

(51) Int. Cl.
  *A61B 17/12* (2006.01)
  *A61B 17/122* (2006.01)
  *A61B 17/128* (2006.01)

(52) U.S. Cl.
  CPC .......... *A61F 2/2433* (2013.01); *A61F 2/2436* (2013.01); *A61B 2017/0488* (2013.01); *A61F 2220/0016* (2013.01); *A61F 2220/0075* (2013.01); *A61F 2230/0054* (2013.01); *A61F 2250/006* (2013.01)

(58) Field of Classification Search
  CPC ............ A61B 17/1227; A61B 17/1285; A61B 2017/0488
  USPC ........................................................ 606/113
  See application file for complete search history.

(56) References Cited

U.S. PATENT DOCUMENTS

| | | | |
|---|---|---|---|
| 4,917,085 A | 4/1990 | Smith | |
| 5,059,177 A | 10/1991 | Towne et al. | |
| 5,332,402 A | 7/1994 | Teitelbaum | |
| 5,411,552 A | 5/1995 | Andersen et al. | |
| 5,554,185 A | 9/1996 | Block et al. | |
| 5,840,081 A | 11/1998 | Andersen et al. | |
| 5,855,601 A | 1/1999 | Bessler et al. | |
| 5,928,250 A * | 7/1999 | Koike ............... | A61B 17/0057 606/139 |
| 5,980,533 A | 11/1999 | Holman | |
| 6,168,614 B1 | 1/2001 | Andersen et al. | |
| 6,287,339 B1 | 9/2001 | Vazquez et al. | |
| 6,419,696 B1 | 7/2002 | Ortiz et al. | |
| 6,425,916 B1 | 7/2002 | Garrison et al. | |
| 6,432,134 B1 | 8/2002 | Anson et al. | |
| 6,458,153 B1 | 10/2002 | Bailey et al. | |
| 6,527,979 B2 | 3/2003 | Constantz et al. | |
| 6,582,462 B1 | 6/2003 | Andersen et al. | |
| 6,652,578 B2 | 11/2003 | Bailey et al. | |
| 6,730,121 B2 | 5/2004 | Ortiz et al. | |
| 6,797,002 B2 | 9/2004 | Spence et al. | |
| 6,908,481 B2 | 6/2005 | Cribier | |
| 6,974,476 B2 | 12/2005 | McGuckin, Jr. et al. | |
| 7,018,408 B2 | 3/2006 | Bailey et al. | |
| 7,037,334 B1 | 5/2006 | Hlavka et al. | |
| 7,077,861 B2 | 7/2006 | Spence | |
| 7,101,395 B2 | 9/2006 | Tremulis et al. | |
| 7,125,421 B2 | 10/2006 | Tremulis et al. | |
| 7,201,772 B2 | 4/2007 | Schwammenthal et al. | |
| 7,235,042 B2 * | 6/2007 | Vanden Hoek ....... | A61F 2/2481 600/16 |
| 7,285,124 B2 * | 10/2007 | Foerster ............. | A61B 17/0469 606/139 |
| 7,429,269 B2 | 9/2008 | Schwammenthal et al. | |
| 7,442,204 B2 | 10/2008 | Schwammenthal et al. | |
| 7,524,330 B2 | 4/2009 | Berreklouw | |
| 7,585,321 B2 | 9/2009 | Cribier | |
| 7,618,446 B2 | 11/2009 | Andersen et al. | |
| 7,621,948 B2 | 11/2009 | Herrmann et al. | |
| 7,708,775 B2 | 5/2010 | Rowe et al. | |
| 7,737,060 B2 | 6/2010 | Strickler et al. | |
| 7,785,366 B2 | 8/2010 | Maurer et al. | |
| 7,951,195 B2 | 5/2011 | Antonsson et al. | |
| 8,062,355 B2 | 11/2011 | Figulla et al. | |
| 8,323,335 B2 | 12/2012 | Rowe et al. | |
| 8,377,115 B2 | 2/2013 | Thompson | |
| 8,398,708 B2 | 3/2013 | Meiri et al. | |
| 8,449,605 B2 | 5/2013 | Lichtenstein et al. | |
| 8,449,606 B2 | 5/2013 | Eliasen et al. | |
| 8,657,872 B2 | 2/2014 | Seguin | |
| 8,663,322 B2 | 3/2014 | Keranen | |
| 8,672,998 B2 | 3/2014 | Lichtenstein et al. | |
| 8,734,507 B2 | 5/2014 | Keranen | |
| 9,078,747 B2 | 7/2015 | Conklin | |
| 9,095,434 B2 | 8/2015 | Rowe | |
| 9,119,718 B2 | 9/2015 | Keranen | |
| 9,237,886 B2 | 1/2016 | Seguin et al. | |
| 9,326,853 B2 | 5/2016 | Olson et al. | |
| 9,364,326 B2 | 6/2016 | Yaron | |
| 9,463,268 B2 | 10/2016 | Spence | |
| 9,474,599 B2 | 10/2016 | Keranen | |
| 9,622,863 B2 | 4/2017 | Karapetian et al. | |
| 2002/0095173 A1 | 7/2002 | Mazzocchi et al. | |
| 2003/0225420 A1 | 12/2003 | Wardle | |
| 2004/0092858 A1 | 5/2004 | Wilson et al. | |
| 2004/0260389 A1 | 12/2004 | Case et al. | |
| 2005/0038493 A1 | 2/2005 | Feeser | |
| 2005/0096736 A1 | 5/2005 | Osse et al. | |
| 2005/0119735 A1 | 6/2005 | Spence et al. | |
| 2005/0137688 A1 | 6/2005 | Salahieh et al. | |
| 2005/0137691 A1 | 6/2005 | Salahieh et al. | |
| 2005/0137698 A1 | 6/2005 | Salahieh et al. | |
| 2005/0182486 A1 | 8/2005 | Gabbay | |
| 2005/0203574 A1 | 9/2005 | Mazzocchi | |
| 2005/0203614 A1 | 9/2005 | Forster et al. | |
| 2005/0203617 A1 | 9/2005 | Forster et al. | |
| 2006/0025857 A1 | 2/2006 | Bergheim et al. | |
| 2006/0161249 A1 | 7/2006 | Realyvasquez et al. | |
| 2006/0195134 A1 | 8/2006 | Crittenden | |
| 2006/0259135 A1 | 11/2006 | Navia et al. | |
| 2006/0276874 A1 | 12/2006 | Wilson et al. | |
| 2007/0100439 A1 | 5/2007 | Cangialosi et al. | |
| 2007/0203575 A1 | 8/2007 | Forster et al. | |
| 2007/0213813 A1 | 9/2007 | Von Segesser et al. | |
| 2007/0265700 A1 | 11/2007 | Eliasen et al. | |
| 2008/0033542 A1 | 2/2008 | Antonsson et al. | |
| 2008/0071361 A1 | 3/2008 | Tuval et al. | |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0071368 A1 | 3/2008 | Tuval et al. | |
| 2008/0071369 A1 | 3/2008 | Tuval et al. | |
| 2008/0082166 A1 | 4/2008 | Styrc et al. | |
| 2008/0125853 A1 | 5/2008 | Bailey et al. | |
| 2008/0208328 A1 | 8/2008 | Antocci et al. | |
| 2008/0208330 A1 | 8/2008 | Keranen | |
| 2008/0208332 A1 | 8/2008 | Lamphere et al. | |
| 2008/0221672 A1 | 9/2008 | Lamphere et al. | |
| 2008/0255660 A1 | 10/2008 | Guyenot et al. | |
| 2008/0255661 A1 | 10/2008 | Straubinger et al. | |
| 2008/0281411 A1 | 11/2008 | Berreklouw | |
| 2009/0005863 A1 | 1/2009 | Goetz et al. | |
| 2009/0054968 A1 | 2/2009 | Bonhoeffer et al. | |
| 2009/0054974 A1 | 2/2009 | McGuckin, Jr. et al. | |
| 2009/0062908 A1 | 3/2009 | Bonhoeffer et al. | |
| 2009/0076598 A1 | 3/2009 | Salahieh et al. | |
| 2009/0112309 A1 | 4/2009 | Jaramillo et al. | |
| 2009/0138079 A1 | 5/2009 | Tuval et al. | |
| 2009/0171432 A1 | 7/2009 | Von Segesser et al. | |
| 2009/0171447 A1 | 7/2009 | Von Segesser et al. | |
| 2009/0216322 A1 | 8/2009 | Le et al. | |
| 2009/0222076 A1 | 9/2009 | Figulla et al. | |
| 2009/0234443 A1 | 9/2009 | Ottma et al. | |
| 2009/0240320 A1 | 9/2009 | Tuval et al. | |
| 2009/0287299 A1 | 11/2009 | Tabor et al. | |
| 2009/0319037 A1 | 12/2009 | Rowe et al. | |
| 2010/0016958 A1 | 1/2010 | St. Goar et al. | |
| 2010/0145440 A1 | 6/2010 | Keranen | |
| 2010/0312333 A1 | 12/2010 | Navia et al. | |
| 2010/0318183 A1 | 12/2010 | Keranen | |
| 2010/0318184 A1 | 12/2010 | Spence | |
| 2012/0059458 A1 | 3/2012 | Buchbinder et al. | |
| 2012/0283820 A1 | 11/2012 | Tseng et al. | |
| 2014/0074299 A1 | 3/2014 | Endou et al. | |
| 2014/0172070 A1 | 6/2014 | Seguin | |
| 2014/0379074 A1 | 12/2014 | Spence et al. | |

(56) References Cited

U.S. PATENT DOCUMENTS

| | | |
|---|---|---|
| 2015/0230921 A1 | 8/2015 | Chau et al. |
| 2015/0282931 A1 | 10/2015 | Brunnett et al. |
| 2015/0335428 A1 | 11/2015 | Keranen |
| 2015/0374493 A1 | 12/2015 | Yaron et al. |
| 2016/0074165 A1 | 3/2016 | Spence et al. |
| 2016/0095705 A1 | 4/2016 | Keranen et al. |
| 2016/0184095 A1 | 6/2016 | Spence et al. |
| 2016/0199177 A1 | 7/2016 | Spence et al. |
| 2016/0256276 A1 | 9/2016 | Yaron |
| 2017/0007399 A1 | 1/2017 | Keranen |
| 2017/0007402 A1 | 1/2017 | Zerkowski et al. |
| 2017/0217385 A1 | 8/2017 | Rinkleff et al. |

FOREIGN PATENT DOCUMENTS

| | | |
|---|---|---|
| DE | 102006052564 B3 | 12/2007 |
| EP | 0592410 A1 | 4/1994 |
| EP | 0850607 A1 | 7/1998 |
| EP | 1432369 A1 | 6/2004 |
| EP | 1469797 A1 | 10/2004 |
| EP | 1521550 A2 | 4/2005 |
| EP | 1653888 A2 | 5/2006 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2806829 A2 | 12/2014 |
| FR | 2906454 A1 | 4/2008 |
| WO | 9117720 A1 | 11/1991 |
| WO | 0060995 A2 | 10/2000 |
| WO | 0149213 A2 | 7/2001 |
| WO | 0154625 A1 | 8/2001 |
| WO | 0247575 A2 | 6/2002 |
| WO | 2004112651 A2 | 12/2004 |
| WO | 2005084595 A1 | 9/2005 |
| WO | 2006011127 A2 | 2/2006 |
| WO | 2005102015 A3 | 4/2007 |
| WO | 2007067942 A1 | 6/2007 |
| WO | 2009024859 A2 | 2/2009 |
| WO | 2009155561 A2 | 12/2009 |
| WO | 2010121076 A2 | 10/2010 |
| WO | 2012063228 A1 | 5/2012 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |

* cited by examiner

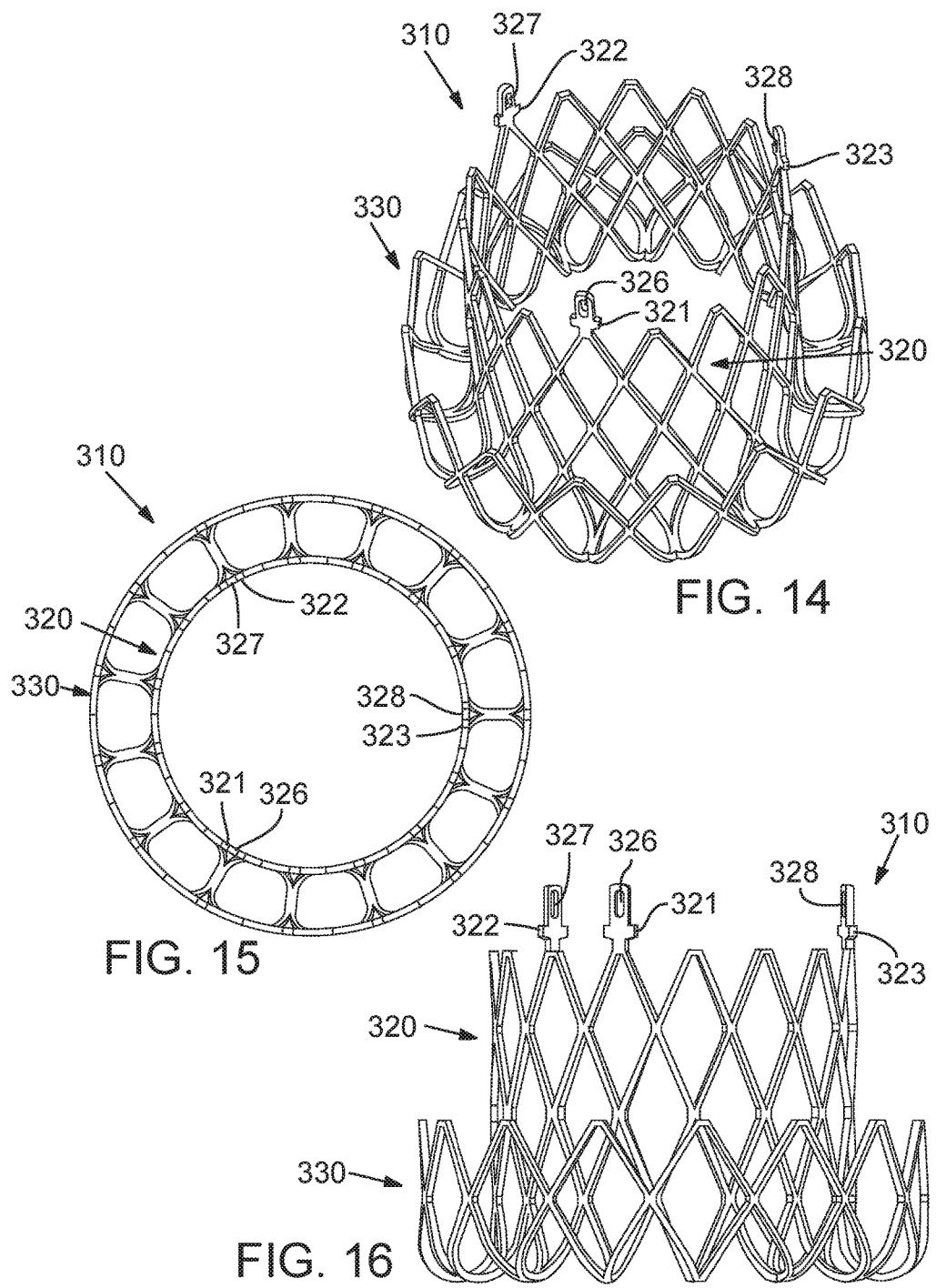

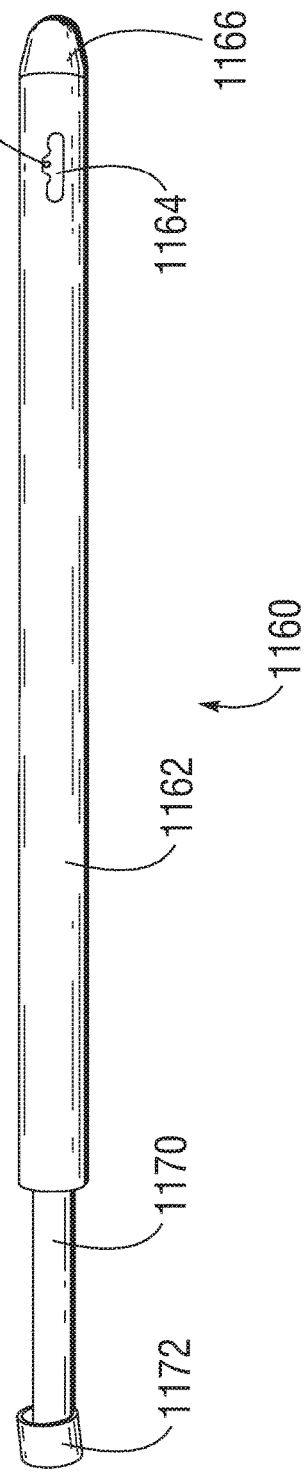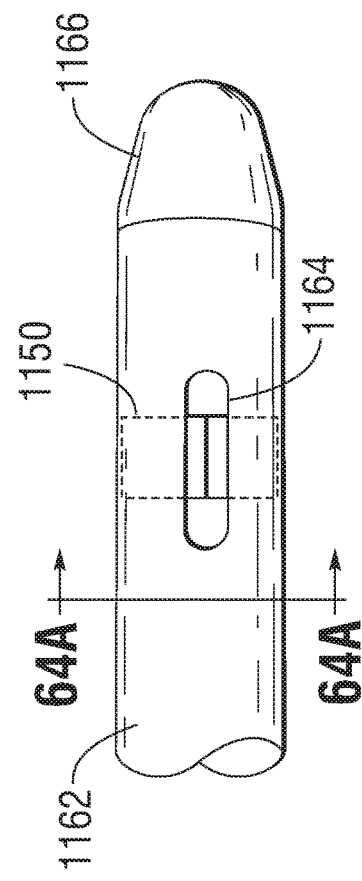

RETAINING MECHANISMS FOR PROSTHETIC VALVES

CROSS-REFERENCE TO RELATED APPLICATIONS

This application is a continuation of U.S. patent application Ser. No. 13/794,311, filed Mar. 11, 2013, now U.S. Pat. No. 9,370,420, which is continuation of U.S. patent application Ser. No. 13/042,160, filed Mar. 7, 2011, now U.S. Pat. No. 8,398,708, which claims the benefit of U.S. provisional application Ser. No. 61/311,143, filed. Mar. 5, 2010, all the disclosures of which are incorporated by reference.

FIELD

This application relates to methods, systems, and apparatus for safely replacing native heart valves with prosthetic heart valves.

BACKGROUND

Prosthetic heart valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery, but such surgeries are dangerous and prone to complication.

More recently a transvascular technique has been developed for introducing and implanting a prosthetic heart valve using a flexible catheter in a manner that is less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Balloon-expandable valves are commonly used for treating heart valve stenosis, a condition in which the leaflets of a valve (e.g., an aortic valve) become hardened with calcium. The hardened leaflets provide a good support structure on which the valve can be anchored within the valve annulus. Further, the catheter balloon can apply sufficient expanding force to anchor the frame of the prosthetic valve to the surrounding calcified tissue. There are several heart conditions, however, that do not involve hardened valve leaflets but which are still desirably treated by valve replacement. For example, aortic insufficiency (or aortic regurgitation) occurs when an aortic valve does not close properly, allowing blood to flow back into the left ventricle. One cause for aortic insufficiency is a dilated aortic annulus, which prevents the aortic valve from closing tightly. In such cases, the leaflets are usually too soft to provide sufficient support for a balloon-expandable prosthetic valve. Additionally, the diameter of the aortic annulus may continue to vary over time, making it dangerous to install a prosthetic valve that is not reliably secured in the valve annulus. Mitral insufficiency (or mitral regurgitation) involves these same conditions but affects the mitral valve.

Self-expanding prosthetic valves are sometimes used for replacing defective native valves with noncalcified leaflets. Self-expanding prosthetic valves, however, suffer from a number of significant drawbacks. For example, once a self-expanding prosthetic valve is placed within the patient's defective heart valve (e.g., the aorta or mitral valve), it continues to exert an outward force on the valve annulus. This continuous outward pressure can cause the valve annulus to dilate further, exacerbating the condition the valve was intended to treat. Additionally, when implanting a self-expanding valve, the outward biasing force of the valve's frame tends to cause the valve to be ejected very quickly from the distal end of a delivery sheath. This makes delivery of the valve very difficult and dangerous to the patient.

The size of the prosthetic valve to be implanted into a patient can also be problematic when treating aortic or mitral insufficiency. Specifically, the size of a prosthetic valve used to treat aortic or mitral insufficiency is typically larger than a prosthetic valve used to treat aortic or mitral stenosis. This larger valve size makes the delivery procedure much more difficult and dangerous to the patient.

Accordingly, there exists a need for improved methods, systems, and apparatus for delivering expandable prosthetic heart valves (e.g., balloon-expandable prosthetic valves). Embodiments of the methods, systems, and apparatus desirably can be used to replace native heart valves that do not have calcified leaflets (e.g., aortic valves suffering from aortic insufficiency). Furthermore, embodiments of the methods, systems, and apparatus desirably enable precise and controlled delivery of the prosthetic valves.

SUMMARY

Disclosed below are representative embodiments of methods, systems, and apparatus used to replace deficient native heart valves with prosthetic heart valves. Embodiments of the disclosed methods, systems, and apparatus can be used, for example, to replace an aortic valve suffering from aortic insufficiency or a mitral valve suffering from mitral insufficiency. These embodiments are not limiting, however, as the disclosed methods, systems, and apparatus can be more generally applied to replace any heart valve.

In certain embodiments, for example, a support structure is delivered to a position on or adjacent to the surface of the outflow side of a native heart valve of a patient, the support structure defining a support-structure interior. An expandable prosthetic heart valve is delivered into the native heart valve and into the support-structure interior. The expandable prosthetic heart valve can be expanded while the expandable prosthetic heart valve is in the support-structure interior and while the support structure is at the position on or adjacent to the surface of the outflow side of the native heart valve, thereby causing one or more native leaflets of the native heart valve to be frictionally secured between the support structure and the expanded prosthetic heart valve. The expandable prosthetic heart valve can be delivered from the inflow or the outflow side of the native heart valve. In certain embodiments, the native heart valve is an aortic valve, and the act of delivering the expandable prosthetic heart valve comprises delivering the prosthetic heart valve through the left ventricle of the patient's heart. In other embodiments, the native heart valve is an aortic valve, and the act of delivering the expandable prosthetic heart valve comprises delivering the prosthetic heart valve through the patient's aorta. In particular embodiments, the native heart valve is an aortic valve, the support structure is a support stent, and the act of delivering the support structure comprises advancing a first catheter through the aortic arch of the patient so that a distal end of the first catheter is near the aortic valve of the patient (the first catheter at least partially enclosing a stent-delivery catheter, an inner catheter, and the support stent in a compressed state) and advancing the stent-delivery catheter and the inner catheter through the first catheter, thereby causing the support stent to be deployed from the distal end of the first catheter and to expand into a decompressed state. In other particular embodiments, the native heart valve is a mitral valve, the support structure is a support band, and the act of delivering the support structure comprises advancing a first loop delivery catheter into the left ventricle of the patient so that a first distal end of the first loop delivery catheter extends around a first portion of the chordae tendineae, advancing a second loop delivery catheter into the left ventricle of the patient so that a second distal end of the second loop delivery catheter extends around a second portion of the chordae tendineae and so that the second distal end of the second loop delivery is adjacent to the first distal end of the first loop delivery catheter, advancing a support band material through an interior of the first loop delivery catheter and an interior of the second loop delivery catheter, attaching a locking member to portions of the support band material, and advancing the locking member along the portions of the support band material and into the left ventricle of the patient, thereby forming the support band around the chordae tendineae. In certain embodiments, the act of delivering the support structure comprises guiding the support structure to the position on or adjacent to the surface of the outflow side of the native heart valve and into a desired orientation, wherein the desired orientation aligns peaks of the support structure with either the tips or the commissures of the one or more native leaflets. In further embodiments, the support structure is disconnected from at least a delivery catheter once the one or more native leaflets of the native heart valve are frictionally secured between the support structure and the expanded prosthetic heart valve. The disconnecting can be performed by retracting an inner catheter relative to a stent-delivery catheter, thereby retracting inner prongs coupled to the inner catheter from corresponding apertures in retaining arms of the support stent. Alternatively, the disconnecting can be performed by cutting through material used to form the support structure, thereby releasing the support structure from a catheter. In certain embodiments, the act of expanding the expandable prosthetic heart valve comprises inflating a balloon of a balloon catheter, the expandable prosthetic heart valve being disposed around the balloon of the balloon catheter.

In other exemplary methods disclosed herein, a guide catheter is advanced through the aortic arch of a patient so that a distal end of the guide catheter is near the aortic valve of the patient. In these embodiments, the guide catheter at least partially encloses a stent-delivery catheter and a compressed support stent releasably connected to the stent-delivery catheter. The stent-delivery catheter is advanced through the guide catheter, thereby causing the support stent to be deployed from the distal end of the guide catheter and to become uncompressed. The uncompressed support stent is positioned adjacent to or on a surface of the aortic side of the aortic valve such that the leaflets of the aortic valve are circumscribed by the uncompressed support stent. The uncompressed support stent can then be disconnected from the stent-delivery catheter. In certain embodiments, to disconnect the support stent from the stent-delivery catheter, an inner catheter positioned in the interior of the stent-delivery catheter can be retracted, causing an inner prong attached to the inner catheter to withdraw from an aperture associated with the support stent, and/or at least one prong attached to the stent-delivery catheter can be disconnected from the support stent.

Other exemplary embodiments disclosed herein include apparatus for securing a prosthetic valve to a native heart valve. For example, certain embodiments comprise a support stent having an annular body that defines one or more peaks and one or more valleys along its circumference. The support stent can be radially compressible and self expandable. The support stent can be sized such that it can be positioned within the aorta of a patient at a location adjacent to the aortic valve and thereby circumscribe the aortic valve. The support stent can further comprise at least one retaining arm comprises an aperture at or near a respective one of the peaks. In particular embodiments, the support stent is formed from a single annular member. In some embodiments, the support stent consists of three peaks and three valleys. The shape formed by the three peaks and the three valleys can approximate the shape of the leaflets of the aortic valve when the aortic valve is fully opened. In certain embodiments, a projection of the annular body onto a first plane is ring shaped or starfish shaped, and the annular body defines the one or more peaks and the one or more valleys in a direction perpendicular to the first plane. For example, the annular body can be sinusoidal or saw-tooth shaped along its circumference. Certain embodiments further comprise a stent delivery catheter having an outer fork that includes one or more outer prongs. At least one of the outer prongs can comprise an aperture that is sized to receive at least a portion of one of the retaining arms of the support stent. An inner catheter can be positioned in an interior of the stent-delivery catheter and have an inner fork. The inner fork can comprise one or more inner prongs, and at least one of the inner prongs can be insertable through the aperture of the one of the retaining arms when the one of the retaining arms has been at least partially inserted through the aperture of a respective one of the outer prongs.

Other exemplary embodiments disclosed herein are systems for delivering a support frame for securing a prosthetic valve in a patient's native heart valve. Exemplary embodiments of the system comprise a guide catheter, a frame-delivery catheter positioned in the interior of the guide catheter, an inner catheter positioned in the interior of the frame-delivery catheter, and an expandable support frame positioned in the interior of the guide catheter in a radially compressed state. A distal end of the frame-delivery catheter can have an outer fork portion that comprises a plurality of flexible outer prongs. A distal end of the inner catheter can have an inner fork portion that comprises a plurality of flexible inner prongs. The expandable support frame can comprise a plurality of retaining arms, which can be releasably connected to corresponding ones of the outer prongs of the outer fork portion and corresponding ones of the inner prongs of the inner fork portion. The expandable support frame can be generally annular and comprise shaped portions configured to frictionally secure native leaflets of a patient's heart valve against an exterior surface of a prosthetic valve when the patient's heart valve has been replaced by the prosthetic valve. Alternatively, the expandable support frame can comprise a main body and a U-shaped lip that surrounds a bottom region of the support frame, the U-shaped lip having a diameter that is greater than a diameter of the main body. In particular embodiments, the guide catheter, frame-delivery catheter, and the inner catheter are axially slidable relative to one another. In some embodiments, the retaining arms of the expandable support frame comprise respective retaining arm apertures through which the corresponding ones of the inner prongs are inserted. The corresponding ones of the outer prongs can comprise, for example, respective outer prong apertures through which the respective retaining arms are inserted. In certain embodiments, the corresponding ones of the outer prongs and the corresponding ones of the inner prongs of the inner fork portion are configured such that relative retraction of either the corresponding ones of the inner prongs or the corresponding ones of the outer prongs causes release of the respective retaining arms.

Another disclosed embodiment is an apparatus comprising a support stent having an annular main body portion and a generally U-shaped rim portion at one end of the main body portion. The support stent of this embodiment is radially compressible into a compressed state and self expandable into an uncompressed state. Furthermore, the rim portion has a diameter that is greater than a diameter of the annular main body portion and that is sized so that an outer perimeter of the rim portion will engage the walls surrounding the aortic valve of a patient when the support stent is positioned within the aorta of the patient at a location adjacent to the aortic valve. In some embodiments, the support stent is made of a shape-memory alloy. In certain embodiments, the annular main body portion is sinusoidal or saw-tooth shaped along its circumference. In some embodiments, the rim portion is located around a bottom region of the main body portion. In certain embodiments, the support stent is made of multiple elements forming a criss-cross pattern. In particular embodiments, the apparatus further comprises at least one retaining arm at or near a top region of the main body portion.

In another disclosed embodiment, a distal end of a first delivery catheter is advanced into the left ventricle of a patient so that a distal portion of the first delivery catheter substantially circumscribes a first half of the patient's chordae tendineae. A distal end of a second delivery catheter is advanced into the left ventricle of the patient so that a distal portion of the second delivery catheter substantially circumscribes a second half of the patient's chordae tendineae and so that a distal end of the second delivery catheter contacts a distal end of the first delivery catheter, thereby forming a delivery catheter junction. A support band material is advanced through one of the first delivery catheter or the second delivery catheter, across the delivery catheter junction, and into the other one of the first delivery catheter or the second delivery catheter. The first delivery catheter and the second delivery catheter are retracted from the left ventricle of the patient. In certain embodiments, the distal end of the first delivery catheter and the distal end of the second delivery catheter are advanced through a puncture in the left ventricle. In other embodiments, the distal end of the first delivery catheter and the distal end of the second delivery catheter are advanced through the aorta of the patient. In some embodiments, the distal end of the first delivery catheter magnetically engages the distal end of the second delivery catheter. In some embodiments, a first steerable sheath and a second steerable sheath are advanced into the left ventricle. In these embodiments, the act of advancing the distal end of the first delivery catheter into the left ventricle comprises advancing the distal end of the first delivery catheter through an interior of the first steerable sheath, and the act of advancing the distal end of the second delivery catheter into the left ventricle comprises advancing the distal end of the second delivery catheter through an interior of the second steerable sheath. In certain embodiments, an introducer sheath is advanced into the left ventricle through a puncture in the left ventricle. In these embodiments, the act of advancing the first steerable sheath and the second steerable sheath into the left ventricle comprises advancing the first steerable sheath and the second steerable sheath through the introducer sheath. In some embodiments, a locking member is attached to portions of the support band material and advanced over the portions of the support band material, thereby adjusting a diameter of a loop formed by the support band material and the locking member and surrounding the chordae tendineae. The act of advancing the locking member over the portions of the support band material can be performed using a pusher tube. In some embodiments, the loop formed by the support band material and the locking member can be positioned around the outflow side of the mitral valve. An expandable prosthetic heart valve can be advanced into the mitral valve and the interior of the loop formed by the support band material and the locking member while the prosthetic heart valve is in a compressed state. The expandable prosthetic heart valve can be expanded into an uncompressed state, thereby causing one or more native leaflets of the mitral valve to be frictionally secured between the loop and the expandable prosthetic heart valve. Portions of the support band material that do not form part of the loop can be severed, thereby releasing the loop.

In another disclosed embodiment, a partial loop is formed around the chordae tendineae of a patient's heart with a cord of biocompatible material. A locking member is attached to portions of the cord of biocompatible material. The locking member is advanced toward the chordae tendineae along the portions of the cord of biocompatible material, thereby decreasing a diameter of a loop formed by the cord of biocompatible material and the locking member. In certain embodiments, an expandable prosthetic heart valve is positioned into the interior of the patient's mitral valve, the loop formed by the cord of biocompatible material and the locking member is positioned around an outflow side of the patient's mitral valve so that the native leaflets of the mitral valve open into the interior of the loop, and the expandable prosthetic heart valve is expanded, thereby causing an exterior surface of the expandable prosthetic heart valve to urge the native leaflets of the mitral valve against an interior surface of the loop and to frictionally secure the expandable prosthetic heart valve to the native leaflets of the mitral valve. In some embodiments, portions of the cord of biocompatible material are cut in order to release the loop formed by the cord of biocompatible material and the locking member. In certain embodiments, an expandable prosthetic heart valve is advanced into the interior of the patient's mitral valve and expanded. The exterior of the expandable prosthetic heart valve can comprise one or more fastening mechanisms configured to engage the native leaflets of the mitral valve and at least temporarily secure the expandable prosthetic heart to the native leaflets. In certain implementations of these embodiments, the loop formed by the cord of biocompatible material and the locking member is positioned around an outflow side of the patient's mitral valve so that the loop circumscribes the native leaflets of the mitral valve and the expanded prosthetic heart valve. In these embodiments, the act of advancing the locking member can decrease the diameter of the loop formed by the cord of biocompatible material and the locking member to a diameter that causes the expanded prosthetic heart valve to be frictionally secured to the native leaflets of the mitral valve. In certain particular embodiments, the locking member is locked at a desired position along the portions of the support band material, thereby forming a support band having a substantially fixed diameter. In some embodiments, the locking member can be unlocked, and the location of the locking member adjusted along the portions of the support band material. In certain embodiments, the act of forming the partial loop around the chordae tendineae of the patient's heart is performed using one or more delivery catheters inserted through the aortic arch of the patient. In other embodiments, the act of forming the partial loop around the chordae tendineae of the patient's heart is performed using one or more delivery catheters inserted through a puncture in the left ventricle of the patient.

Another disclosed embodiment is a system that comprises a first delivery catheter having a first distal end region and a first distal end, a second delivery catheter having a second distal end region and a second distal end, and an introducer sheath defining an interior that is configured to receive the first delivery catheter and the second delivery catheter. In these embodiments, the first distal end region is steerable into a first semi-circular shape, the second distal end region is steerable into a second semi-circular shape, the first distal end has a first magnetic polarity, and the second distal end has a second magnetic polarity opposite the first magnetic polarity. In certain embodiments, the introducer sheath is rigid and is sized for insertion through a puncture in the left ventricle of a patient. In other embodiments, the introducer sheath is bendable and is sized for insertion into the aortic arch of a patient. In some embodiments, the system further comprises a first catheter delivery sheath and a second catheter delivery sheath. In these embodiments, the first catheter delivery sheath defines a first interior configured to receive the first delivery catheter and has a first distal sheath region that naturally assumes a first arced shape. Further, the second catheter delivery sheath defines a second interior configured to receive the second delivery catheter and has a second distal sheath region that naturally assumes a second arced shape. In these embodiments, the interior of the introducer sheath is further configured to receive the first catheter delivery sheath, the second catheter delivery sheath, the first delivery catheter, and the second delivery catheter. In certain embodiments, the first catheter delivery sheath and the second catheter delivery sheath are manufactured at least in part from a shape-memory alloy.

Another disclosed embodiment is a system comprising a pusher tube defining a first pusher tube lumen and a second pusher tube lumen and a locking member defining a first locking member lumen and a second locking member lumen. In these embodiments, the first and second pusher tube lumens are sized to receive respective portions of a cord of material, and the first and second locking member lumens are also sized to receive the respective portions of the cord and are further configured to allow movement of the locking member in a first direction along the respective portions of the cord when pushed by the pusher tube but prevent movement of the locking member in a second direction opposite the first direction along the respective portions of the cord. In certain embodiments, the pusher tube further comprises a rotatable cutting element located at a distal end of the pusher tube, the rotatable cutting element being controllable from a proximal region of the pusher tube. In some embodiments, the first locking member lumen and the second locking member lumen each comprise one or more angled collars or teeth. In certain embodiments, the system further comprises an introducer sheath having an introducer sheath interior through which the pusher tube and the locking member are advanceable. In some embodiments, the system further comprises a prosthetic-heart-valve-delivery catheter. In these embodiments, the introducer sheath interior is further configured to simultaneously receive the pusher tube and the prosthetic-heart-valve-delivery catheter.

Another disclosed embodiment is a system comprising a locking member configured to receive two portions of a cord of biocompatible material and to secure the two portions in a desired position relative to one another, an adjustment tool configured to position the locking member into the desired position and to engage a locking mechanism in the locking member that secures the locking member to the two portions at the desired position, a balloon catheter on which an expandable prosthetic heart valve is disposed, and an introducer sheath defining an interior in which the adjustment tool and the balloon catheter can be simultaneously located. In certain embodiments, the adjustment tool is further configured to disengage the locking mechanism in the locking member, thereby unlocking the locking member from the two portions of the cord. In particular embodiments, the locking member comprises a pin member and a ring member. The pin member can have a first end, a second end, and openings for receiving the two portions of the cord, and the ring member can have openings for receiving the two portions of the cord and be configured to receive at least a portion of the first end of the pin member. In some embodiments, the adjustment tool comprises a fork member positioned at a distal end of the adjustment tool, an inner push member, and an outer push member. In these embodiments, the inner push member can be contained within a lumen of the adjustment tool and the outer push member can have a greater diameter than the inner push member and surround at least a portion of the inner push member.

Another disclosed embodiment comprises a support band having an annular body that defines a support band interior. The support band of this embodiment is formed from a biocompatible material having a first end that is secured to an opposite second end via a locking mechanism. The support band of this embodiment is sized such that it can be positioned adjacent to the outflow side of the mitral valve of a patient and thereby circumscribe the native leaflets of the mitral valve. Moreover, the support band interior has a fixed diameter when the first end is secured to the second end such that when an expandable prosthetic heart valve is expanded within the mitral valve and within the support band interior, the native leaflets of the mitral valve become pinched between the expandable prosthetic heart valve and the support band, thereby frictionally securing the expandable prosthetic heart valve to the mitral valve. In certain embodiments, the first end of the support band has a larger diameter than the second end, and the first end of the support band defines an interior into which the second end can be inserted and secured by the locking mechanism. In some embodiments, the locking mechanism comprises a snap-fit connection formed between the first end and the second end of the support band. In certain embodiments, the locking mechanism comprises a locking member having a first lumen configured to receive the first end of the support band and a second lumen configured to receive the second end of the support band, the first lumen and the second lumen each comprising one or more angled teeth or collars that allow movement of the locking mechanism along the support band in only a single direction. In some embodiments, the locking mechanism comprises a multi-element mechanism that can be selectively locked to and unlocked from the first end and the second end of the support band. In certain embodiments, one or more clamps are positioned on the support band.

In another disclosed embodiment, a prosthetic heart valve is delivered into an interior of a native heart valve and expanded. A support band is delivered to a position on or adjacent to the surface of the outflow side of the native heart valve such that an interior of the support band surrounds at least a portion of the prosthetic heart valve and at least a portion of one or more native leaflets of the native heart valve. The diameter of the support band is adjusted until the one or more native leaflets of the native heart valve are frictionally secured between the support band and the prosthetic heart valve. The prosthetic heart valve can be an expandable prosthetic heart valve and expanded once it is delivered into the interior of the native heart valve. The support band can be formed from a shape-memory metal or cord of support band material and an adjustable locking member through which portions of the cord extend. During delivery of the support band, the support band can be disconnected from at least a delivery catheter once the one or more native leaflets of the native heart valve are frictionally secured between the support band and the prosthetic heart valve (e.g., by cutting through material used to form the support band).

In another disclosed embodiment a support member is advanced so that the support member at least partially surrounds native leaflets of a heart valve. The support member includes a locking member coupled to a proximal end of the support member. A distal end of the support member is advanced to engage the locking member and couple the distal end of the support member to the locking member to form a closed loop support band that at least partially surrounds the native leaflets. A prosthetic heart valve is expanded inside the closed loop support band so that the native leaflets are in contact with an outside surface of the prosthetic device and an inside surface of the support band. In certain embodiments, the support member comprises an internal lumen. The act of advancing the support member can include advancing a guidewire to an outflow side of a mitral valve, advancing the guidewire at least partially surround the native leaflets, and advancing the internal lumen of the support member over the guidewire. In certain embodiments, the act of advancing the internal lumen of the support member comprises advancing a proximal end of the locking member using a pusher tube. In other embodiments, the act of advancing the guidewire to at least partially surround the native leaflets comprises advancing a precurved catheter out of a delivery catheter, advancing the guidewire out of the precurved catheter, and advancing the guidewire in the generally circular shape until the guidewire at least partially surrounds the leaflets. The precurved catheter is configured to bend in a predetermined manner when it is advanced out of the delivery catheter and the guidewire is precurved so that it will bend to form a generally circular shape when advanced from the precurved catheter. In certain embodiments, the guidewire forms a circular shape that is in a plane that is generally perpendicular to a longitudinal axis of the delivery catheter. IN other embodiments, a snare catheter is advanced out of the delivery catheter to capture a distal end of the guidewire and pull the distal end of the guidewire into a receiving area of the locking member. The receiving area can be configured to receive and engage the distal end of the support member. In certain embodiments, the native heart valve can be a mitral valve and the act of advancing the support member so that the support member at least partially surrounds the native leaflets comprises advancing the support member to at least partially surround chordae tendineae associated with both native leaflets of the mitral valve. In other embodiments, the support member is delivered percutaneously and the prosthetic heart valve is delivered transapically. In still other embodiments, the support member and prosthetic heart valve are delivered transapically. In some embodiments, the locking member comprises a receiving area and the act of advancing the distal end of the support member to engage the locking member comprises advancing the distal end of the support member into the receiving area and securing the distal end of the support member in the receiving area. In certain embodiments, the distal end of the support member comprises a nose cone with a grooved section and the act of securing the distal end of the support member comprises advancing the grooved section of the nose cone until a biased tab member engages the grooved section of the nose cone to restrict proximal movement of the nose cone relative to the locking member.

In other embodiments, a support band is provided for at least partially surrounding native leaflets of a heart valve to facilitate the securing of a prosthetic device in the valve annulus by frictionally engaging the native leaflets between the support band and the prosthetic valve. The support band comprises an elongate support member having a proximal end and a distal end and a locking member coupled to the proximal end of the support member. The locking member can have a receiving area and a securing member. The securing member can be configured to restrict proximal movement of the distal end of the support member relative to the locking member when the distal end of the support member is advanced into the receiving area. In certain embodiments, the securing member comprises a lumen extending along its length to receive a guidewire therethrough. In other embodiments, the securing member comprises a tab member that is biased to at least partially extend into the receiving area and engage a distal end of the support member. In other embodiments, the distal end of the support member comprises a nose cone with a grooved section, with the grooved section being configured to mate with the tab member when the nose cone is received in the receiving area of the locking member.

In another embodiment, a delivery system for encircling native leaflets of a heart valve to deliver a support band that at least partially surrounds the native leaflets is provided. The system comprises a delivery catheter with a lumen of a first diameter, a precurved catheter with a lumen and an outer diameter that is smaller than the first diameter, and a precurved guidewire receivable in the lumen of the precurved catheter. The precurved catheter is receivable in the lumen of the delivery catheter and biased to return to a predetermined curved configuration when it is advanced out of an opening in the delivery catheter. The precurved guidewire is biased to return to a predetermined curved configuration when it is advanced out of the precurved catheter. In some embodiments, the precurved catheter has a first bending section at its distal end and a second bending section proximal to the first bending section. When the first and second bending sections are advanced out of the delivery catheter, the first bending section is in a plane that is generally perpendicular to a longitudinal axis of the delivery catheter and the second bending section is in a plane that is at an angle of less than 90 degrees relative to the longitudinal axis of the delivery catheter. In other embodiments, when the precurved guidewire is advanced out of the precurved catheter, the precurved guidewire forms a generally circular shape that is in the same general plane as the first bending section of the precurved catheter. In other embodiments, the system further comprises a support band that has an elongate support member and a locking member. The elongate support member has a lumen for receiving the guidewire, and the locking member is coupled to a proximal end of the support member and has a receiving area for receiving the distal end of the support member. In certain embodiments, the locking member further comprises a securing member to secure the distal end of the support member in the receiving area. The securing member can comprise a tab member that is biased to at least partially extend into the receiving area and engage the distal end of the support member. In certain embodiments, the distal end of the support member can comprise a nose cone with a grooved section, with the grooved section being configured to mate with the tab member when the nose cone is received in the receiving area of the locking member.

The foregoing and other objects, features, and advantages of the disclosed technology will become more apparent from the following detailed description, which proceeds with reference to the accompanying figures.

BRIEF DESCRIPTION OF THE DRAWINGS

FIG. 3 shows the delivery system before the support structure is deployed, and FIG. 4 shows the delivery system after the support structure is deployed.

FIG. 14 is a perspective view of another exemplary embodiment of a support structure according to the disclosed technology.

FIG. 15 is a top view of the support structure embodiment shown in FIG. 14

FIG. 16 is a side view of the support structure embodiment shown in FIG. 14.

In FIGS. 19-27, the support band is deployed using a transapical approach.

FIG. 62 illustrates a delivery system for delivering a support member at least partially around native leaflets of a heart valve.

FIG. 63 illustrates an enlarged view of a portion of the delivery system of FIG. 62.

DETAILED DESCRIPTION

General Considerations

Figure 1:
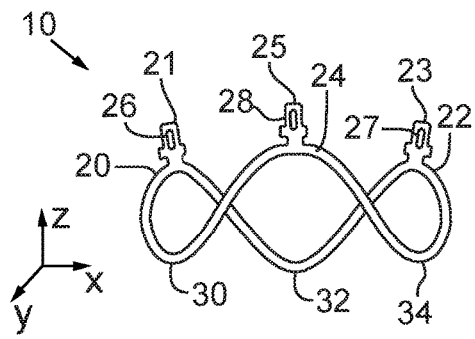
FIG. 1 is a perspective view of an exemplary embodiment of a support structure according to the disclosed technology.

Disclosed below are representative embodiments of a support structure (sometimes referred to as a "support stent," "support frame," "support band," or "support loop") that can be used to secure a prosthetic heart valve within a native heart valve. For illustrative purposes, embodiments of the support structure are described as being used to secure a transcatheter heart valve ("THV") in the aortic valve or the mitral valve of a heart. It should be understood that the disclosed support structure and THV can be configured for use with any other heart valve as well. Also disclosed herein are exemplary methods and systems for deploying the support structure and corresponding THV. Although the exemplary methods and systems are mainly described in connection with replacing an aortic or mitral valve, it should be understood that the disclosed methods and systems can be adapted to deliver a support structure and THV to any heart valve.

For illustrative purposes, certain embodiments of the support structure are described as being used in connection with embodiments of the balloon-expandable THV described in U.S. Patent Application Publication No. 2007/0112422 (U.S. application Ser. No. 11/280,063), which is hereby expressly incorporated herein by reference. It should be understood, however, that this particular usage is for illustrative purposes only and should not be construed as limiting. Instead, embodiments of the disclosed support structure can be used to secure a wide variety of THVs delivered through a variety of mechanisms (e.g., self-expanding heart valves, other balloon-expanding heart valves, and the like). For instance, any of the embodiments described in U.S. Pat. No. 6,730,118 can be used with embodiments of the disclosed support structure. U.S. Pat. No. 6,730,118 is hereby expressly incorporated herein by reference.

The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

Exemplary Embodiments for Replacing Aortic Valves

FIG. 1 is a perspective view showing an exemplary embodiment of a support stent or frame 10. Support stent 10 has a generally annular or torroidal body formed from a suitable shape-memory metal or alloy, such as spring steel, Elgiloy®, or Nitinol. Desirably, the material from which the support stent 10 is fabricated allows the support stent to automatically expand to its functional size and shape when deployed but also allows the support stent to be radially compressed to a smaller profile for delivery through the patient's vasculature. In other embodiments, however, the stent is not self expanding. In these embodiments, and as more fully explained below, other mechanisms for expanding the stent can be used (e.g., a balloon catheter).

In the illustrated embodiment, the projection of the support stent 10 onto an x-y plane has a generally annular or torroidal shape. The illustrated support stent 10 further defines a number of peaks and valleys (or crests and troughs) along its circumference. For example, the support stent 10 is sinusoidally shaped in the z direction. In other embodiments, the support stent 10 is shaped differently in the z direction (e.g., sawtooth-shaped, ringlet-shaped, square-wave shaped, or otherwise shaped to include peaks and valleys).

The illustrated support stent 10 includes three peaks 20, 22, 24 and three valleys 30, 32, 34. In the illustrated embodiment, the peaks 20, 22, 24 are positioned above the valleys 30, 32, 34 in the z direction. In some embodiments, the peaks have greater radii than the valleys 30, 32, 34, or vice versa. For instance, in some embodiments, the projection of the support stent 10 onto an x-y plane forms a closed shape having a variable radius (e.g., a starfish shape).

The size of the support stent 10 can vary from implementation to implementation. In particular embodiments, the support stent 10 is sized such that the support stent can be positioned within the aorta of a patient at a location adjacent to the aortic valve, thereby circumscribing the aortic valve. Furthermore, in order to frictionally secure a prosthetic heart valve in its interior, certain embodiments of the support stent 10 have a diameter that is equal to or smaller than the diameter of the prosthetic heart valve when fully expanded. In particular embodiments, for instance, the support stent can have an inner or outer diameter between 10 and 50 mm (e.g., between 17 and 28 mm) and a height between 5 and 35 mm (e.g., between 8 and 18 mm). Furthermore, the thickness of the annular body of the support stent 10 may vary from embodiment to embodiment, but in certain embodiments is between 0.3 and 1.2 mm.

Figure 2:
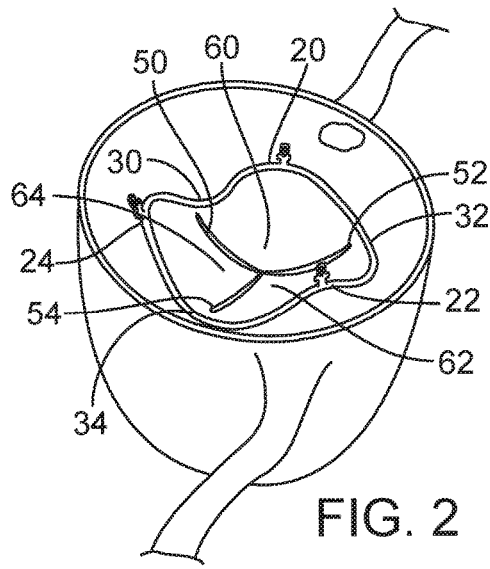
FIG. 2 is a cross-sectional view of a native aortic valve with the support structure of FIG. 1 positioned therein.

FIG. 2 is a perspective view of the exemplary support stent 10 positioned on the surface of an outflow side of a native aortic valve and further illustrates the shape of the support stent. In particular, it can be seen from FIG. 2 that the valleys 30, 32, 34 of the support stent 10 are shaped so that they can be placed adjacent to commissures 50, 52, 54 of the native leaflets 60, 62, 64 of the aortic valve. Furthermore, in the illustrated embodiment, the peaks 20, 22, 24 are shaped so that they generally approximate or mirror the size and shape of the leaflets 60, 62, 64 but are slightly smaller and lower than the height of the leaflets 60, 62, 64 at their tips when the aortic valve is fully opened. In other embodiments, the peaks 20, 22, 24 are oriented so that they are adjacent to the commissures 50, 52, 54 of the native leaflets 60, 62, 64 and the valleys are opposite the apexes of the leaflets 60, 62, 64. The support stent 10 can be positioned in any other orientation within the aortic valve as well.

It should be understood that the shape of the support stent or frame 10 can vary from implementation to implementation. For example, in some embodiments, the support stent is not sinusoidal or otherwise shaped in the z-plane. In other embodiments, the support stent is shaped as a cylindrical band or sleeve. In general, the support stent or frame can be any shape that defines an interior through which a THV can be inserted, thereby causing the native leaflets of the aortic valve (or other heart valve) to be pinched or securely held between the support stent and the THV. Furthermore, the support stent can have a more complex structure. For example, although the support stent illustrated in FIGS. 1 and 2 is formed from a single annular member (or strut), the support stent can comprise multiple annular elements that interlock or are otherwise connected to one another (e.g., via multiple longitudinal members).

Returning to FIG. 1, the illustrated support stent 10 also include retaining arms 21, 23, 25 that can be used to help position and deploy the support stent 10 into its proper location relative to the native aortic valve. The retaining arms 21, 23, 25 can have respective apertures 26, 27, 28. An exemplary deployment system and procedure for deploying the support stent 10 using the retaining arms 21, 23, 25 are described in more detail below. The support stent 10 can also have one or more barbs located on its surface. Such barbs allow the support stent 10 to be more securely affixed to the tissue surrounding the stent or the leaflets of the aorta.

Figure 3:
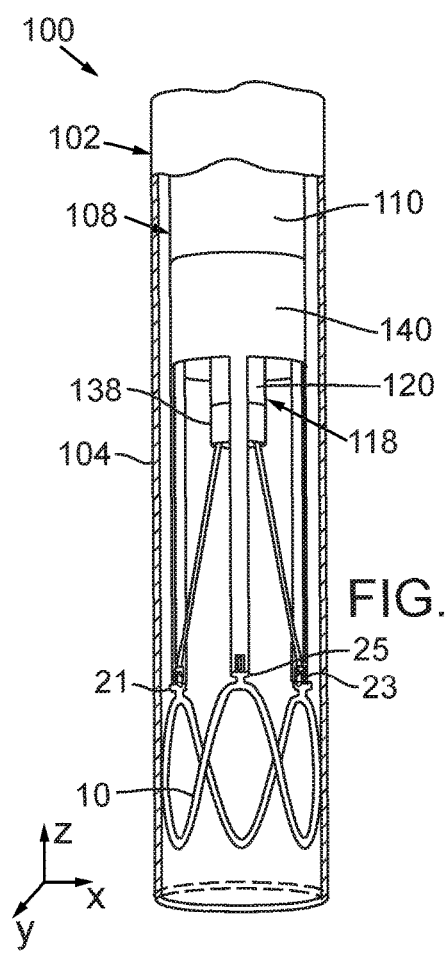
FIGS. 3 and 4 are perspective views of an exemplary delivery system for the support structure of FIG. 1. In particular.
Figure 4:
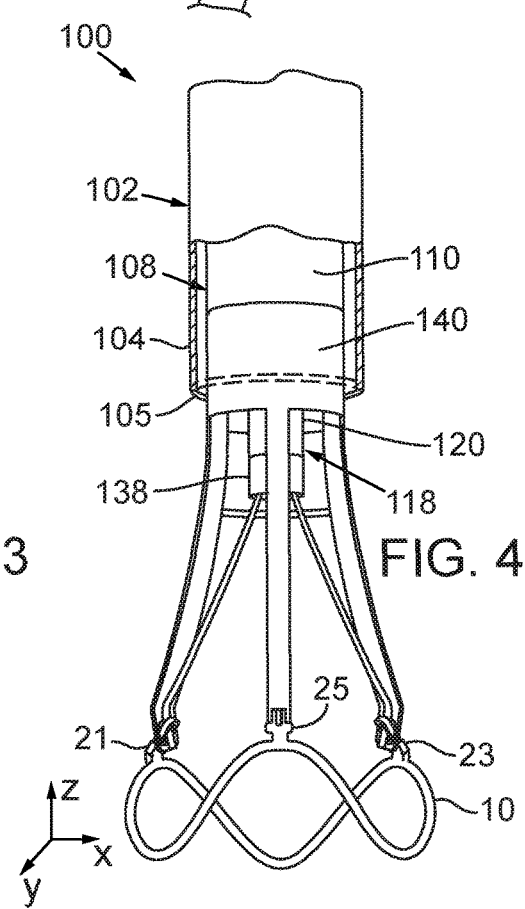

FIGS. 3 and 4 are side views of the distal end portion of an exemplary delivery apparatus 100 for delivering the support stent 10 to its location adjacent the native aortic valve through a patient's vasculature. In particular, FIG. 3 shows the delivery apparatus when the support stent 10 is in a compressed, predeployed state, whereas FIG. 4 shows the delivery apparatus when the support stent 10 is in a decompressed, deployed state. The delivery apparatus 100 comprises a guide catheter 102 having an elongated shaft 104, whose distal end 105 is open in the illustrated embodiment. In other embodiments, the distal end 105 of the guide catheter 102 can be tapered into a conical shape comprising multiple "flaps" forming a protective nose cone that can be urged apart when the support stent 10 and any interior catheters are advanced therethrough. Furthermore, for illustrative purposes, the guide catheter 102 is shown as being partially cut away, thus revealing the catheters in its interior.

A proximal end (not shown) of the guide catheter 102 is connected to a handle of the delivery apparatus 100. During delivery of a support stent, the handle can be used by a surgeon to advance and retract the delivery apparatus through the patient's vasculature. In a particular use, the delivery apparatus 100 is advanced through the aortic arch of a patient's heart in the retrograde direction after having been percutaneously inserted through the femoral artery. The guide catheter can be configured to be selectively steerable or bendable to facilitate advancement of the delivery system 100 through the patient's vasculature. An exemplary steerable guide catheter as can be used in embodiments of the disclosed technology is described in detail in U.S. Patent Application Publication No. 2007/0005131 (U.S. patent application Ser. No. 11/152,288), which is hereby expressly incorporated herein by reference.

The delivery apparatus 100 also includes a stent delivery catheter 108 positioned in the interior of the guide catheter 102. The stent delivery catheter 108 has an elongated shaft 110 and an outer fork 140 connected to a distal end portion of the shaft 110. The shaft 110 of the stent delivery catheter 108 can be configured to be moveable axially relative to the shaft 104 of the guide catheter 102. Furthermore, the shaft 110 of the stent delivery catheter 108 can be sized so that its exterior wall is adjacent to or in contact with the inner wall of the shaft 104 of the guide catheter 102.

The delivery apparatus 100 can also include an inner catheter 118 positioned in the interior of the stent delivery catheter 108. The inner catheter 118 can have an elongated shaft 120 and an inner fork 138 secured to the distal end portion of the shaft 120. The shaft 120 of the inner catheter 118 can be configured to be moveable axially relative to the shaft 104 of the guide catheter 102 and relative to the shaft 110 of the stent delivery catheter 108. Furthermore, the shaft 120 of the inner catheter 118 can be sized so that its exterior wall is adjacent to or in contact with the inner wall of the shaft 110 of the stent delivery catheter 108. A guide wire (not shown) can be inserted into the interior of the inner catheter 118. The guide wire can be used, for example, to help ensure proper advancement of the guide catheter 102 and its interior catheters through the vasculature of a patient.

Figure 5:
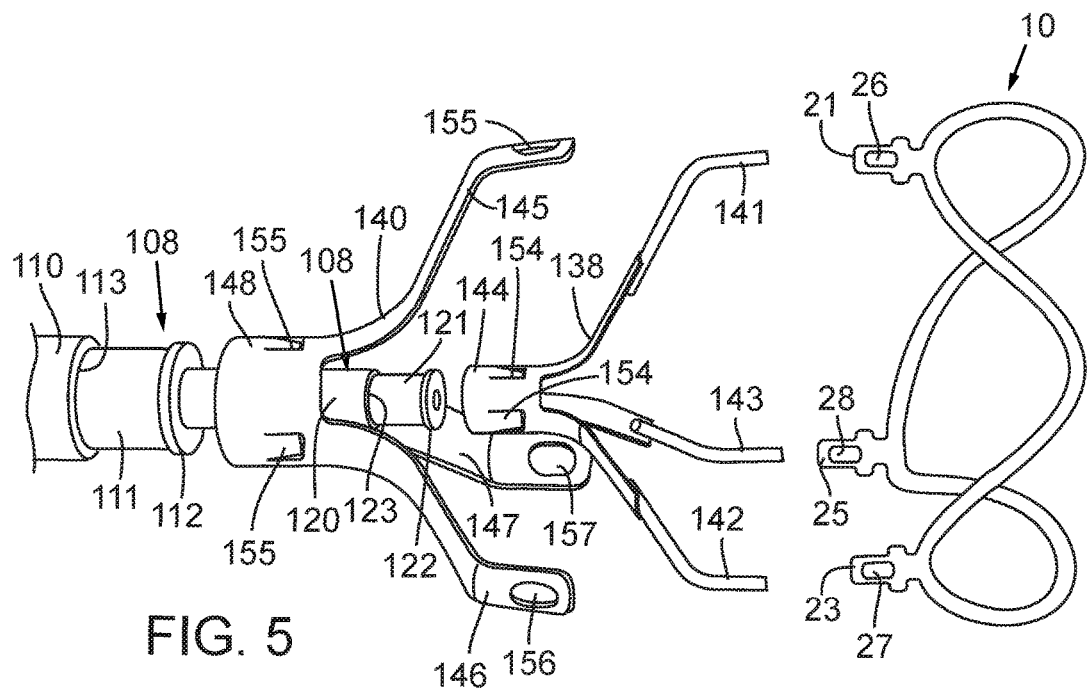
FIG. 5 is an exploded view of the components of the exemplary delivery system shown in FIGS. 3 and 4.

As best shown in FIG. 5, a stent retaining mechanism is formed from the inner fork 138 attached to the distal end portion of the shaft 120 of the inner catheter 118 and the outer fork 140 attached to the distal end portion of the shaft 110 of the stent delivery catheter 108. The inner fork 138 includes a plurality of flexible inner prongs 141, 142, 143 (three in the illustrated embodiment) at is distal end corresponding to the retaining arms 21, 23, 25 of the support stent 10, and a head portion 144 at its proximal end. The outer fork 140 includes a plurality of flexible outer prongs 145, 146, 147 (three in the illustrated embodiment) at its distal end corresponding to the retaining arms 21, 23, 25 of the stent 10, and a head portion 148 at its proximal end. The distal end portions of the outer prongs 145, 146, 147 are formed with respective apertures 155, 156, 157 sized to receive the retaining arms 21, 23, 25.

Figure 6:
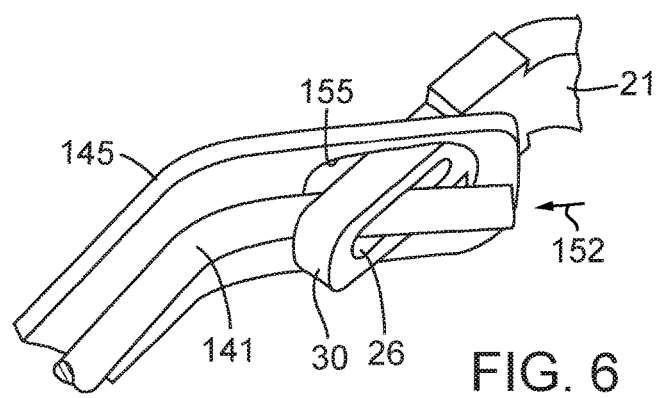
FIG. 6 is a zoomed-in perspective view showing the mechanism for releasably connecting the support structure to the exemplary delivery system of FIGS. 3 and 4.

FIG. 6 is a zoomed-in view of one of the retaining arms 21, 23, 25 as it interfaces with corresponding prongs of the outer fork 140 and the inner fork 138. In this example, retaining arm 21 is shown, though it should be understood that the retaining mechanism is similarly formed for the retaining arms 23, 25. The distal end portion of the outer prong 145 is formed with the aperture 155. When assembled, the retaining arm 21 of the stent is inserted through the aperture 155 of the prong 145 of the outer fork and the prong 141 of the inner fork is inserted through the aperture 26 of the retaining arm 21 so as to retain the retaining arm 21 in the aperture 155.

Retracting the inner prong 141 proximally (in the direction of arrow 152) to remove the prong from the aperture 26 allows the retaining arm 21 to be removed from the aperture 155, effectively releasing the retaining arm from the retaining mechanism. For instance, the outer prong 145 and the retaining arm 21 can be formed such that when the inner prong 141 is withdrawn from the aperture 26, the outer prong 145 flexes radially inward (downward in FIG. 7) and/or the retaining arm 21 of the support stent flexes radially outward (upward in FIG. 7), thereby causing the retaining arm 21 to be removed from the aperture 155. In this manner, the retaining mechanism formed by the inner fork 138 and the outer fork 140 create a releasable connection with the support stent 10 that is secure enough to retain the support stent to the stent delivery catheter 108 and to allow the user to adjust the position of the support stent after it is deployed. When the support stent 10 is positioned at the desired location adjacent to the leaflets of the aortic valve, the connection between the support stent and the retaining mechanism can be released by retracting the inner fork 138 relative to the outer fork 140, as further described below. In other embodiments, the function of the inner fork and the outer fork can be reversed. For example, the prongs of the inner fork can be formed with apertures sized to receive the corresponding retaining arms of the support stent and the prongs of the outer fork can be inserted through the apertures of the retaining arms when the retaining arms are placed through the apertures of the prongs of the inner fork.

As best shown in the exploded view in FIG. 5, the head portion 144 of the inner fork can be connected to the distal end portion of the shaft 120 of the inner catheter 118. In the illustrated embodiment, for example, the head portion 144 of the inner fork is formed with a plurality of angularly spaced, inwardly biased retaining flanges 154. An end piece of the shaft 120 can be formed as a cylindrical shaft having an annular groove 121. On the distal side of the annular groove 121, the shaft 120 can have a collar 122 with an outer diameter that is slightly greater than the diameter defined by the inner free ends of the flanges 154. Thus, the inner fork 138 can be secured to the end piece by inserting head portion 144 of the inner fork onto the end piece of the shaft 120 until the flanges 154 flex inwardly into the annular groove 121 adjacent the collar 122, thereby forming a snap-fit connection between the head portion 144 and the shaft 120. The head portion 144 can have a proximal end that engages an annular shoulder 123 of the shaft 120 that is slightly larger in diameter so as to prevent the head portion from sliding longitudinally along the shaft 120 in the proximal direction.

The head portion 148 of the outer fork can be secured to a distal end portion of the shaft 110 of the stent delivery catheter 108 in a similar manner. As shown in FIG. 5, the head portion 148 can be formed with a plurality of angularly spaced, inwardly biased retaining flanges 155. An end piece of the shaft 110 can be formed as a cylindrical shaft having an annular groove 111. On the distal side of the annular groove 111, the shaft 110 can have a collar 112 with an outer diameter that is slightly greater than the diameter defined by the free ends of the flanges 155. Thus, the outer fork 140 can be secured to the end piece of the shaft 110 by inserting the shaft 110 onto the head portion 148 until the flanges flex inwardly into the groove 111, thereby forming a snap-fit connection between the head portion 148 and the shaft 110. The head portion 148 can have a proximal end that engages an annular shoulder 123 of the shaft 110 that is slightly larger so as to prevent the head portion from sliding longitudinally along the shaft 110 in the proximal direction.

In FIG. 3, the support stent 10 is shown in a radially compressed state in the interior of the elongated shaft 104 of the guide catheter 102. In the radially compressed state, the distance along the z axis between a peak and an adjacent valley of the support stent is greater than the distance along the z axis between the peak and the adjacent valley when the support stent is in it uncompressed state. The distal end portion of the shaft 104 can also be referred to as a delivery sheath for the stent 10. In this undeployed and compressed state, the prongs of the outer fork 140 and the inner fork 138 of the stent delivery catheter 108 and the inner catheter 118 engage the retaining arms 21, 23, 25 of the support stent 10 in the manner described above with respect to FIGS. 5 and 6. To deploy the support stent 10 in the illustrated embodiment (advance the stent from the delivery system), the stent delivery catheter 108 and the inner catheter 118 are advanced toward the distal end 105 of the guide catheter 102 using one or more control handles or mechanisms (not shown) located at the proximal end of the guide catheter 102. This action causes the support stent 10 to be advanced outwardly through the distal end 105 of the guide catheter 102 and expand into its relaxed, uncompressed state (shown, for example, in FIGS. 1 and 2).

FIG. 4 is a perspective view showing the support stent 10 after it has been advanced from the distal end of the guide catheter 102. As seen in FIG. 4, the support stent 10 now assumes its relaxed, uncompressed shape but remains connected to the outer fork 140 and the inner fork 138 at its retaining arms 21, 23, 25. In this configuration, the support stent 10 can be rotated (in the clockwise or counter-clockwise directions) or repositioned (in the proximal and distal directions and/or into a different position in the x-y plane) into a proper orientation adjacent to its intended target area. For example, the support stent 10 can be positioned against the upper surfaces of leaflets of the aortic valve in the manner illustrated in FIG. 2 while the support stent 10 remains connected to the delivery system 100 via the retaining arms 21, 23, 25. As more fully illustrated below in FIGS. 7-12, a prosthetic valve (e.g., a THV) can be delivered to the aortic valve through a transapical approach (e.g., through the apex of the heart and through the left ventricle) and deployed within the native valve such that the prosthetic valve is secured in place by frictional engagement between the support stent, the native leaflets, and the prosthetic valve.

In particular embodiments, the support stent 10 is shaped so that the THV can be positioned in the interior of the support stent along with the native leaflets of the aortic valve. More specifically, the support stent 10 can be shaped such that the native leaflets become trapped or pinched between the support stent 10 and the exterior of the THV when the THV is installed. For instance, the diameter of the support stent 10 can be equal to or smaller than the maximum diameter of the THV when fully expanded, thus causing the THV to be frictionally fit to the leaflets of the aortic valve and the support stent 10. This friction fit creates a solid foundation for the THV that is independent of the state or condition of the leaflets in the aortic valve. For example, THVs are most commonly used for treating aortic stenosis, a condition in which the leaflets of the aortic valve become hardened with calcium. The hardened leaflets typically provide a good support structure for anchoring the THV within the aortic annulus. Other conditions may exist, however, in which it is desirable to implant a THV into the aortic valve and which do not result in a hardening of the leaflets of the aortic valve. For instance, the support stent 10 can be used as a foundation for a THV when treating patients with aortic insufficiency. Aortic insufficiency results when the aortic annulus dilates such that the aortic valve does not close tightly. With this condition, the aortic annulus is larger than normal and would otherwise require a large THV. Using a support stent or frame (such as the support stent or frame 10), however, a smaller THV can be used, thereby making the THV delivery process easier and safer. Furthermore, the use of a support stent protects against displacement of the THV if there is any further dilation of the aortic valve.

A support stent can be used to secure a THV in any situation in which the aorta or aortic valve may not be in condition to help support the THV and is not limited to cases of aortic insufficiency. For example, a support stent 10 can be used in cases in which the aortic annulus is too dilated or in which the leaflets of the aorta are too weak or soft. The support stent can be used to create an anchor for the THV, for instance, in cases in which the native leaflet tissue is too soft because of excess collagen in the aorta.

Figure 7:
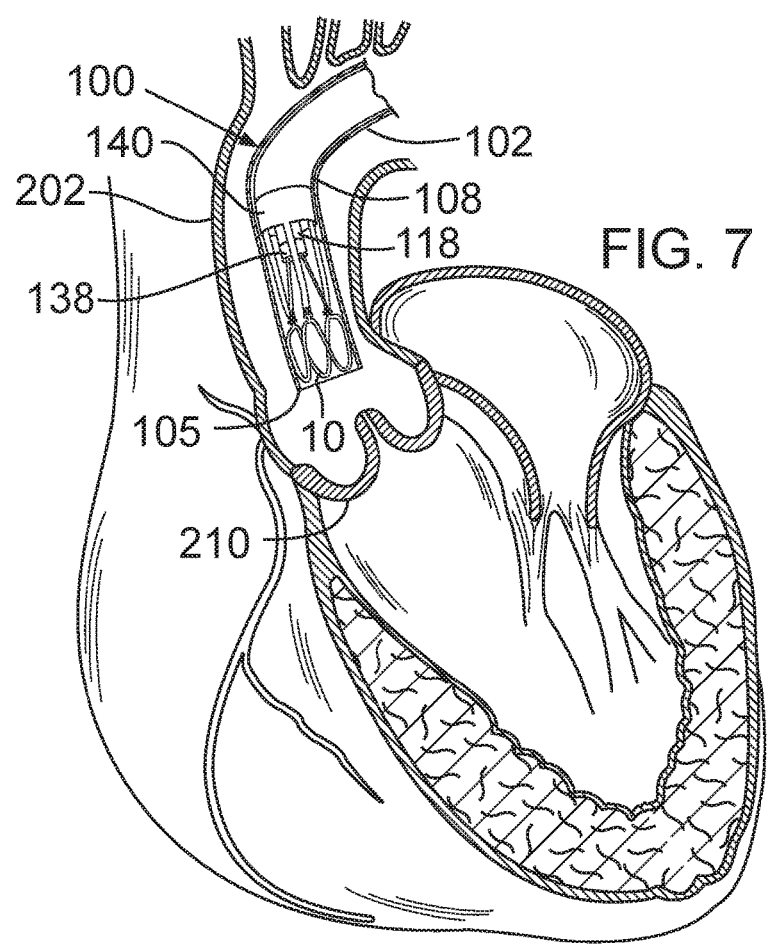
FIGS. 7 and 8 are cross-sectional views of a patient's heart illustrating how the delivery system of FIGS. 3 and 4 can operate to deploy the support structure of FIG. 1 to a desired position on the patient's aortic valve.
Figure 8:
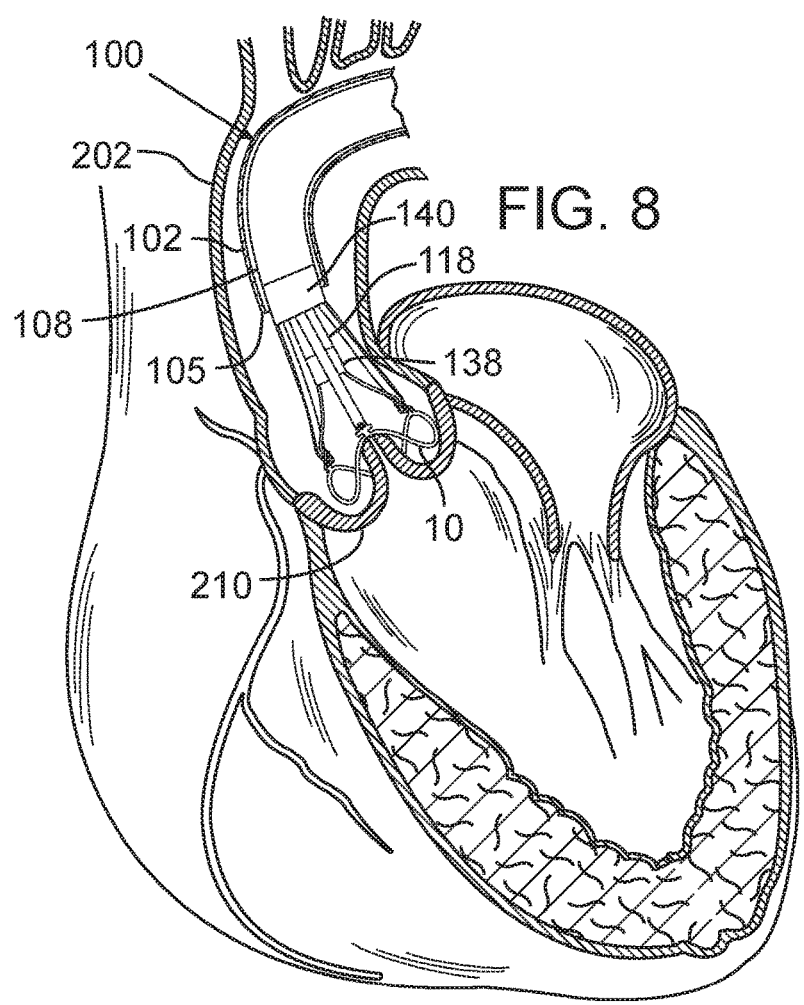

FIGS. 7-13 illustrate one exemplary procedure for deploying the support stent and securing a THV to the support stent. In particular, FIGS. 7-8 are cross-sectional views through the left side of a patient's heart showing the acts performed in delivering the support stent 10 through the aortic arch to the aortic valve. FIGS. 9-13 are cross-sectional views through the left side of a patient's heart showing the acts performed in deploying a THV 250 and having it engage the support stent 10. In order to better illustrate the components of the delivery system 100, the guide catheter 102 is shown partially cut away in FIGS. 7-13. For the sake of brevity, certain details concerning the delivery system of the THV 250 are omitted. Additional details and alternative embodiments of the delivery system for the THV 250 that may be used with the support stent described herein are discussed in U.S. Patent Application Publication No. 2007/0112422 (U.S. application Ser. No. 11/280,063), which is hereby expressly incorporated herein by reference.

FIG. 7 shows the guide catheter 102 of the delivery system 100 as it is advanced through the aortic arch 202 into a position near the surface of the outflow side of the aortic valve 210. The delivery system 100 can be inserted through the femoral artery of the patient and advanced into the aorta in the retrograde direction. FIG. 7 also shows the stent delivery catheter 108, the inner catheter 118, and the support stent 10. In FIG. 7, the support stent 10 is in its radially compressed, predeployment state. Also seen in FIG. 7 are the outer fork 140 and the inner fork 138, which couple the radially compressed support stent 10 to the distal ends of the stent delivery catheter 108 and the inner catheter 118, respectively.

FIG. 8 shows the support stent 10 after it has been advanced through the distal end of the guide catheter 102 and assumes its final, uncompressed shape in a position above and adjacent to the aortic valve 210. The support stent 10 can also be placed directly on the surface of the outflow side of the aortic valve. FIG. 8 shows that the stent delivery catheter 108 and the inner catheter 118 have been advanced though the distal end of the guide catheter 102, thereby pushing the support stent 10 out of the guide catheter and allowing it to expand into its natural shape. In particular embodiments, the support stent 10 is rotated and positioned as necessary so that the support stent generally circumscribes the aortic valve and so that the peaks of the support stent are aligned with the tips of the natural leaflets of the aortic valve 210. Therefore, when the THV is inserted and expanded within the aortic valve 210, the leaflets of the aortic valve will engage at least the majority of the surface in the interior of the support stent 10. This alignment will create an overall tighter fit between the support stent 10 and the THV. In other embodiments, the support stent 10 is rotated and positioned as necessary so that the peaks of the support stent 10 are aligned with the commissures or other portions of the aortic valve. The position of the guide catheter 102 and the support stent 10 relative to the aortic valve 210, as well as the position of other elements of the system, can be monitored using radiopaque markers and fluoroscopy, or using other imaging systems such as transesophageal echo, transthoracic echo, intravascular ultrasound imaging ("IVUS"), or an injectable dye that is radiopaque.

Also seen in FIG. 8 are the prongs of the outer fork 140 and the prongs of the inner fork 138. In the exemplary procedure, the prongs of the outer fork 140 and the inner fork 138 remain secured to the support stent 10 until the THV is deployed and frictionally engaged to the support stent. The inner and outer forks desirably form a connection between the stent 10 and the delivery system that is secure and rigid enough to allow the surgeon to hold the stent 10 at the desired implanted position against the flow of blood while the THV is being implanted.

In FIG. 8, the support stent 10 is self-expanding. In other embodiments, however, the support stent may not be self-expanding. In such embodiments, the support stent can be made of a suitable ductile material, such as stainless steel. In addition, a mechanism for expanding the support stent can be included as part of the delivery system 100. For example, the support stent can be disposed around a balloon of a balloon catheter in a compressed state. The balloon catheter can have a shaft that is interior to the inner catheter 118. Because the stent 10 is not self-expanding, the distal end portion of the guide catheter 102 need not extend over the compressed support stent. During delivery of the support stent, the support stent, balloon catheter, inner catheter 118, and stent delivery catheter 108 can be advanced from the distal end of the guide catheter 102. The balloon portion of the balloon catheter can be inflated, causing the support stent to expand. The balloon portion can subsequently be deflated and the balloon catheter withdrawn into the delivery system 100 to remove the balloon from the interior of the support stent while the support stent remains connected to the inner catheter for positioning of the support stent. The delivery of the support stent otherwise proceeds as in the illustrated embodiment using the self-expanding support stent 10.

Figure 9:
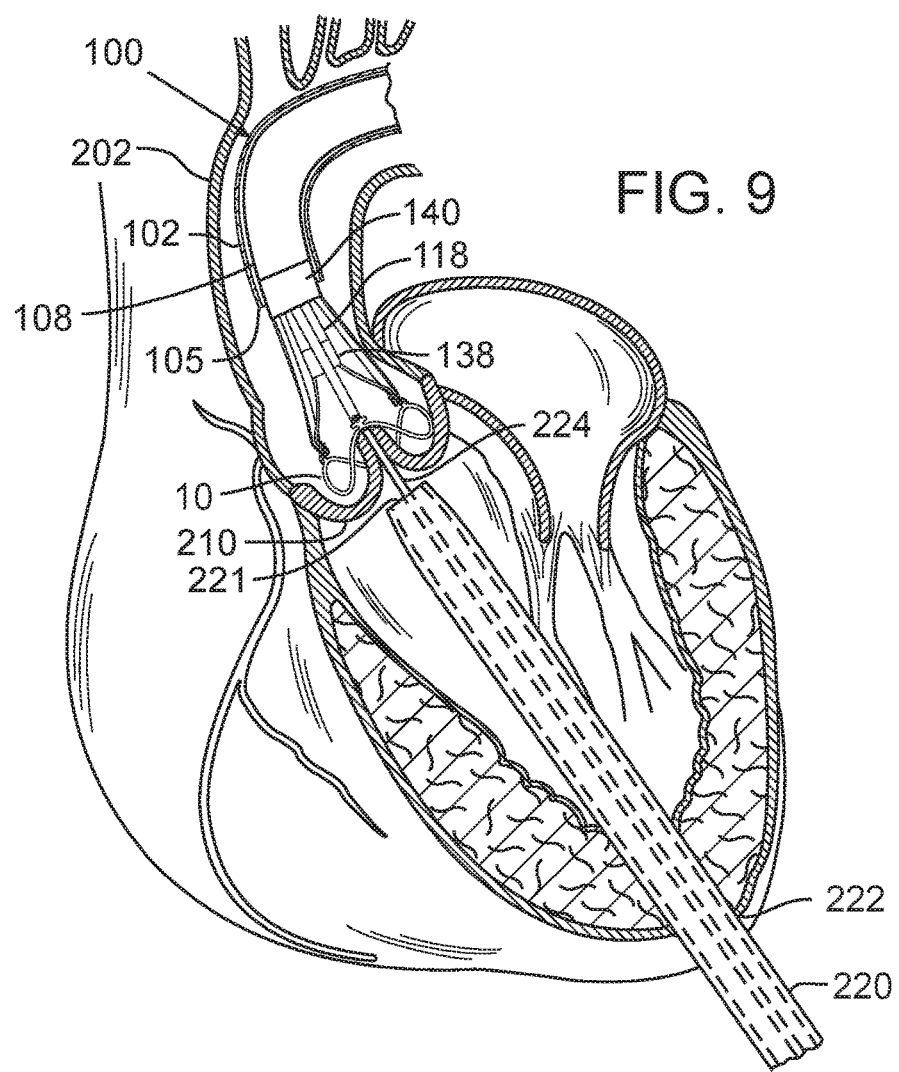
FIGS. 9-13 are cross-sectional views of a patient's heart illustrating how an exemplary transcatheter heart valve ("THV") can be deployed to the patient's aortic valve and frictionally secured to the native leaflets using the support structure of FIG. 1.

FIG. 9 shows an introducer sheath 220 passing into the left ventricle through a puncture 222 and over a guidewire 224 that extends upward through the aortic valve 210. The surgeon locates a distal tip 221 of the introducer sheath 220 just to the inflow side of the aortic valve 210. The position of the introducer sheath 220 relative to the aortic valve 210, as well as the position of other elements of the system, can be monitored using radiopaque markers and fluoroscopy, or using other imaging systems.

Figure 10:
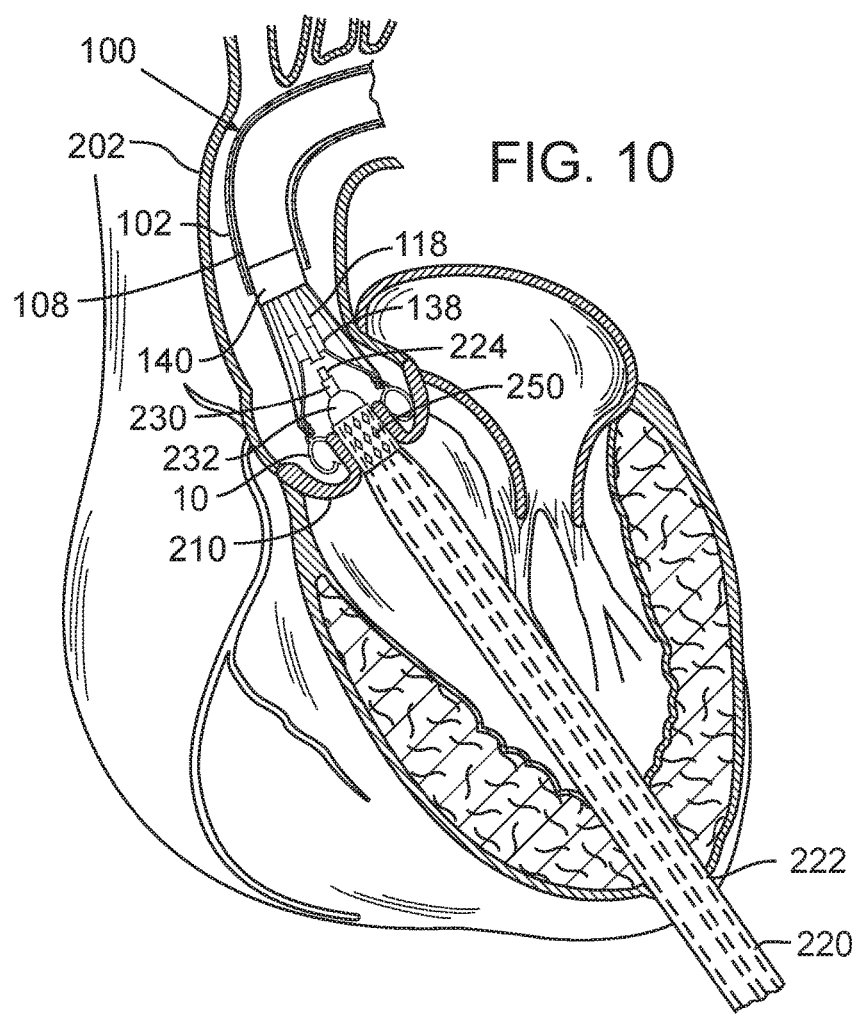
Figure 11:
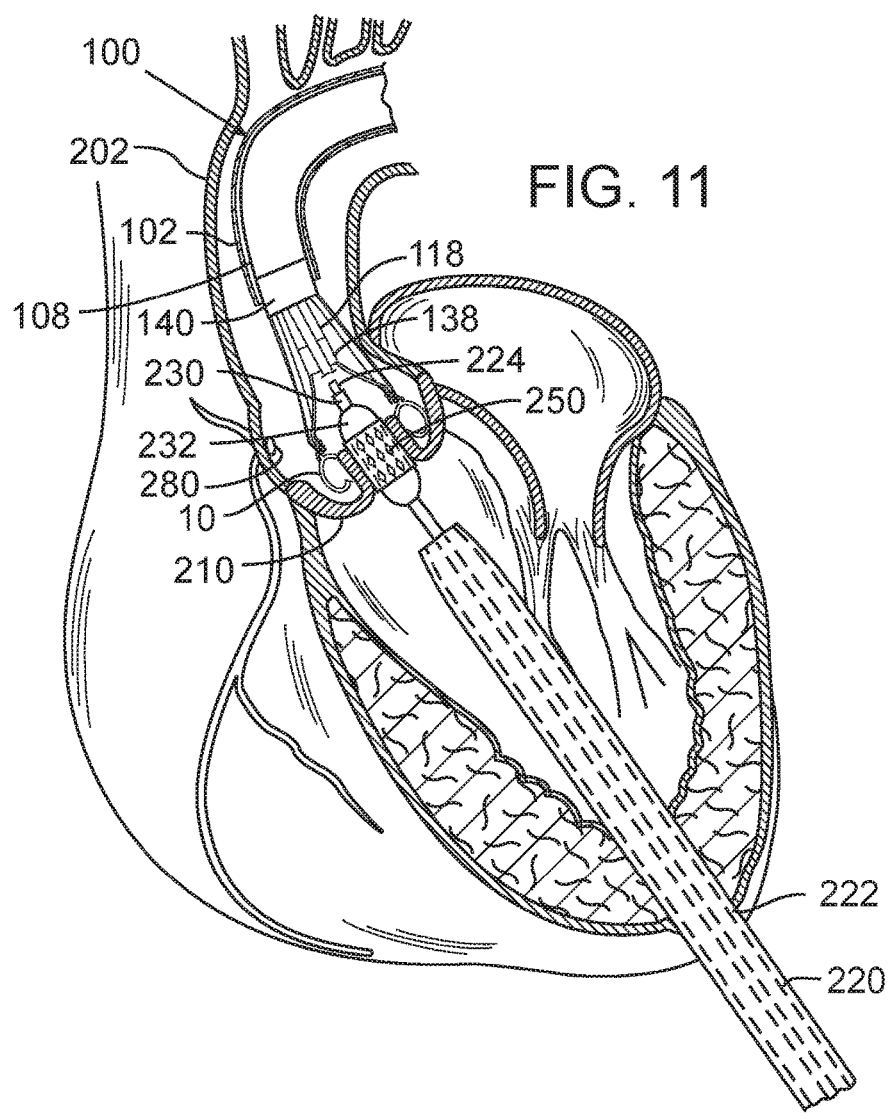
Figure 12:
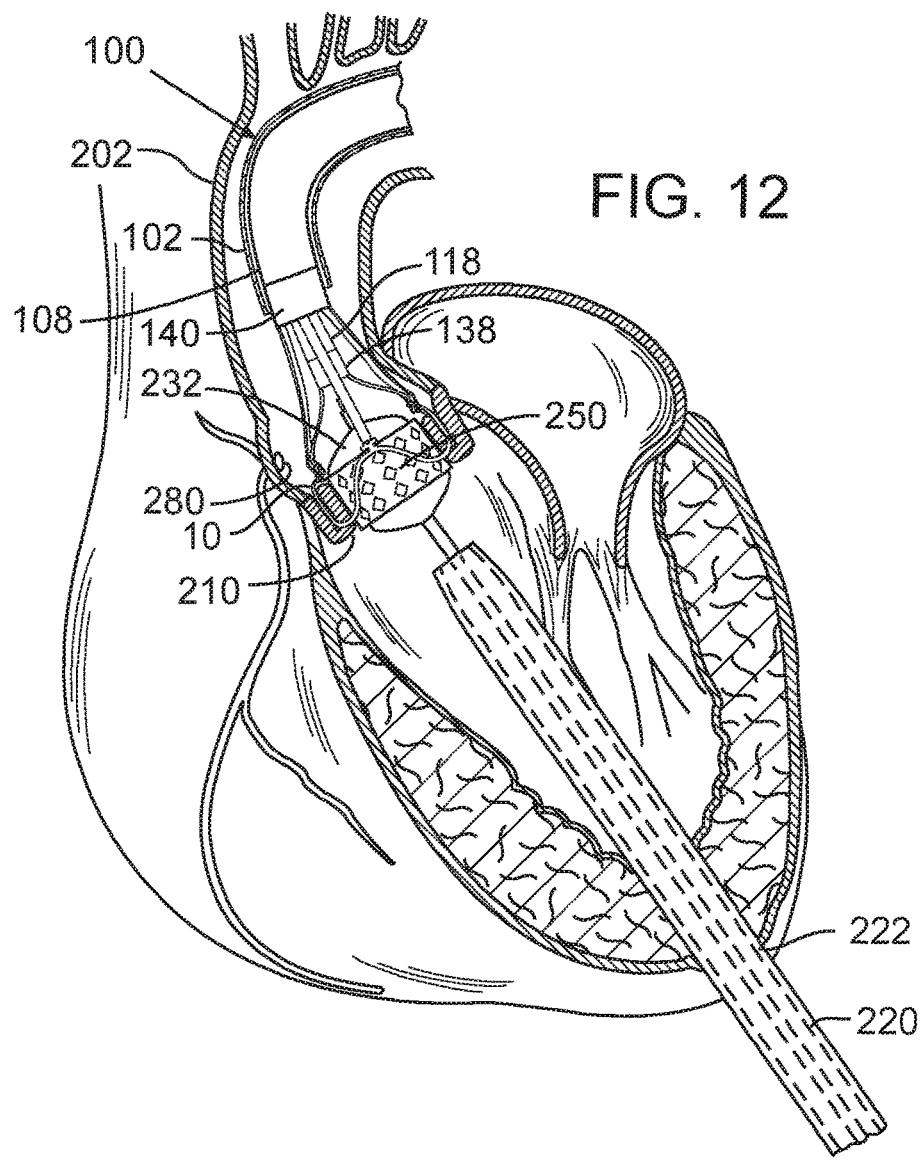
Figure 13:
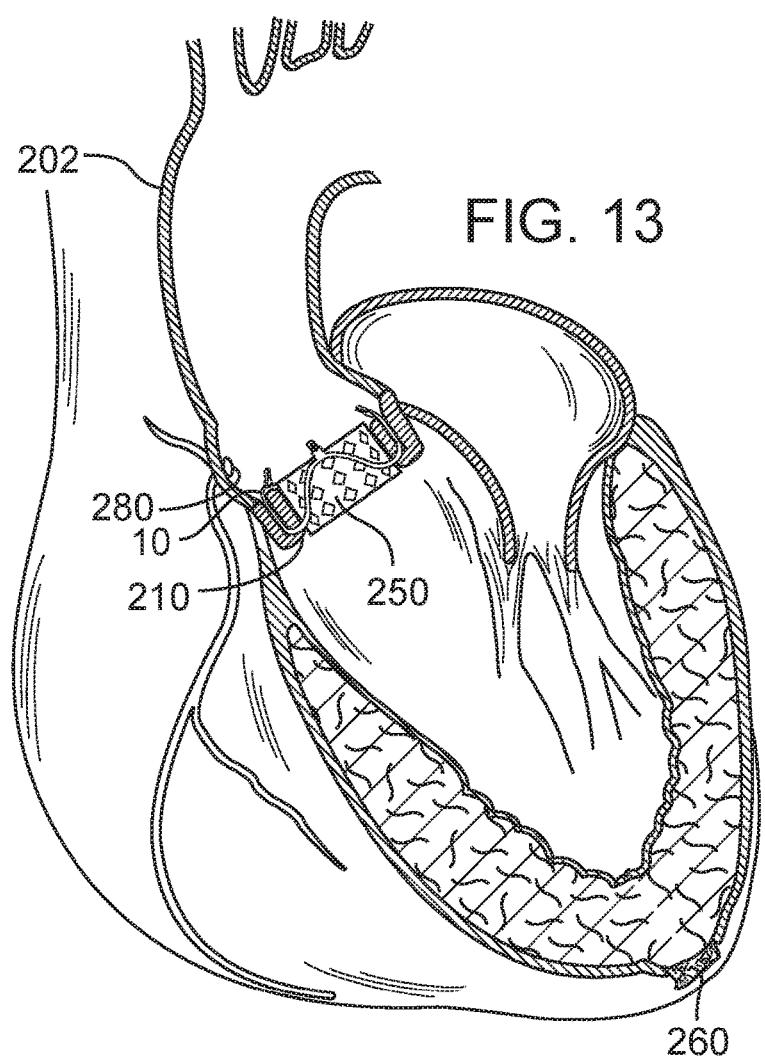

FIG. 10 shows the advancement of the balloon catheter 230 over the guidewire 224 and through the introducer sheath 220. Ultimately, as seen in FIG. 11, the THV 250 is located at the aortic annulus and between the native aortic leaflets. FIG. 11 also illustrates retraction of the introducer sheath 220 from its more distal position in FIG. 10. Radiopaque markers may be provided on the distal end of the introducer sheath 220 to more accurately determine its position relative to the valve 210 and balloon 232. In order to better illustrate the components of the delivery system for the THV, FIGS. 10-11 do not show the front third of the support stent 10 or the corresponding outer and inner prong of the outer fork and the inner fork, respectively. Furthermore, for purpose of illustrating the relative position of the support stent 10 on the THV 250, FIGS. 12-13 show the front third of the support stent 10 and the front of the THV 250, but do not show the portions of the native heart valve that would be secured by the front of the support stent 10. It is to be understood, however, that a corresponding leaflet of the native heart valve would be secured between the support stent 10 and the THV 250.

Again, the precise positioning of the THV 250 may be accomplished by locating radiopaque markers on its distal and proximal ends. In some embodiments, the surgeon can adjust the position of the valve 250 by actuating a steering or deflecting mechanism within the balloon catheter 230. Furthermore, the rotational orientation of the valve 250 can be adjusted relative to the cusps and commissures of the native aortic valve by twisting the balloon catheter 230 from its proximal end and observing specific markers on the valve (or balloon catheter) under fluoroscopy. One of the coronary ostia 280 opening into one of the sinuses of the ascending aorta is also shown in FIG. 11, and those of skill in the art will understand that it is important not to occlude the two coronary ostia with the prosthetic valve 250.

FIG. 11 shows the THV 250 in its contracted or unexpanded state crimped around the balloon 232. When the surgeon is satisfied of the proper positioning and rotational orientation of the valve 250, the balloon 232 is expanded to engage the support stent 10 as seen in FIG. 12. The engagement of the support stent 10 to the exterior of the THV 250 pinches the leaflets of the aortic valve between the support stent and the THV 250, and thereby secures the THV within the annulus of the aortic valve. Once secured into this position, the inner catheter 118 of the delivery system 100 can be retracted, thereby causing the prongs of the inner fork 138 to become disengaged from the retaining arms of the support stent 10. Once the prongs of the inner fork 138 are disengaged, the prongs of the outer fork 140 can be disengaged from the retaining arms by retracting the stent delivery catheter 108. Once disengaged from the support stent, the delivery system 100 can be retracted from the aortic arch and removed from the patient.

It should be noted that the valve 250 can take a variety of different forms and may comprise an expandable stent portion that supports a valve structure. The stent portion desirably has sufficient radial strength to hold the valve at the treatment site and to securely engage the support stent 10. Additional details regarding balloon expandable valve embodiments that can be used in connection with the disclosed technology are described in U.S. Pat. Nos. 6,730,118 and 6,893,460, both of which are hereby expressly incorporated herein by reference.

Once the valve 250 is properly implanted, as seen in FIG. 13, the balloon 232 is deflated, and the entire delivery system including the balloon catheter 230 is withdrawn over the guidewire 224. The guidewire 224 can then be withdrawn, followed by the introducer sheath 220. Ultimately, purse-string sutures 260 at the left ventricular apex can be cinched tight and tied to close the puncture.

FIGS. 14-16 shows another embodiment of a support stent or frame 310 that can be used to help secure a THV into the interior of a native heart valve, such as the aortic valve. In particular, FIG. 14 is a perspective view of the support stent 310, FIG. 15 is a top view of the support stent 310, and FIG. 16 is a side view of the support stent 310. Like support stent 10, support stent 310 has a generally annular or torroidal body formed from a suitable shape-memory metal or alloy, such as spring steel, Elgiloy®, or Nitinol. The support stent 310 is also radially compressible to a smaller profile and can self expand when deployed into its functional size and shape. In other embodiments, however, the support stent 310 is not self expanding.

The support stent 310 includes a generally cylindrical main body portion 320 and a rim portion 330. The support stent 310 can be a mesh structure, which can be formed, for example, from multiple elements in which approximately half of the elements are angled in a first direction and approximately half of the elements are angled in a second direction, thereby creating a criss-cross or diamond-shaped pattern. In the illustrated embodiment, the rim portion 330 has a greater diameter than the main body portion 320 and is formed as an extension at a bottom region of the main body portion that is folded outwardly from the main body portion and back toward a top region of the main body portion. The rim portion 330 thus forms a U-shaped rim or lip around the bottom region of the support stent 310. In general, the rim portion 330 is designed to have a diameter that is slightly larger than the walls of the aortic arch that surround the aortic valve. Thus, when the support stent 310 is delivered to the aortic valve and deployed at the aorta, the rim portion 330 expands to engage the surrounding aorta wall and frictionally secures the support stent 310. At the same time, the main body portion 320 defines an interior into which an expandable THV can be expanded and which further engages the native leaflets of the aortic valve. Thus, the main body portion 320 operates in the same manner as the support stent 10 described above and illustrated in FIGS. 1-12, whereas the rim portion 330 of the support stent 310 operates to secure the support stent in place by engaging the walls of the aorta that surround the aortic valve.

As best seen in FIGS. 14 and 16, the support stent 310 further includes retaining arms 321, 322, 323 that can be used to help position and deploy the support stent 310 into its proper location relative to the native aortic valve. The retaining arms 321, 322, 323 can have respective apertures 326, 327, 328. In general, the retaining arms 321, 322, 323 are constructed and function in a similar manner as retaining arms 21, 23, 25 described above in the embodiment illustrated in FIGS. 1-12.

Figure 17:
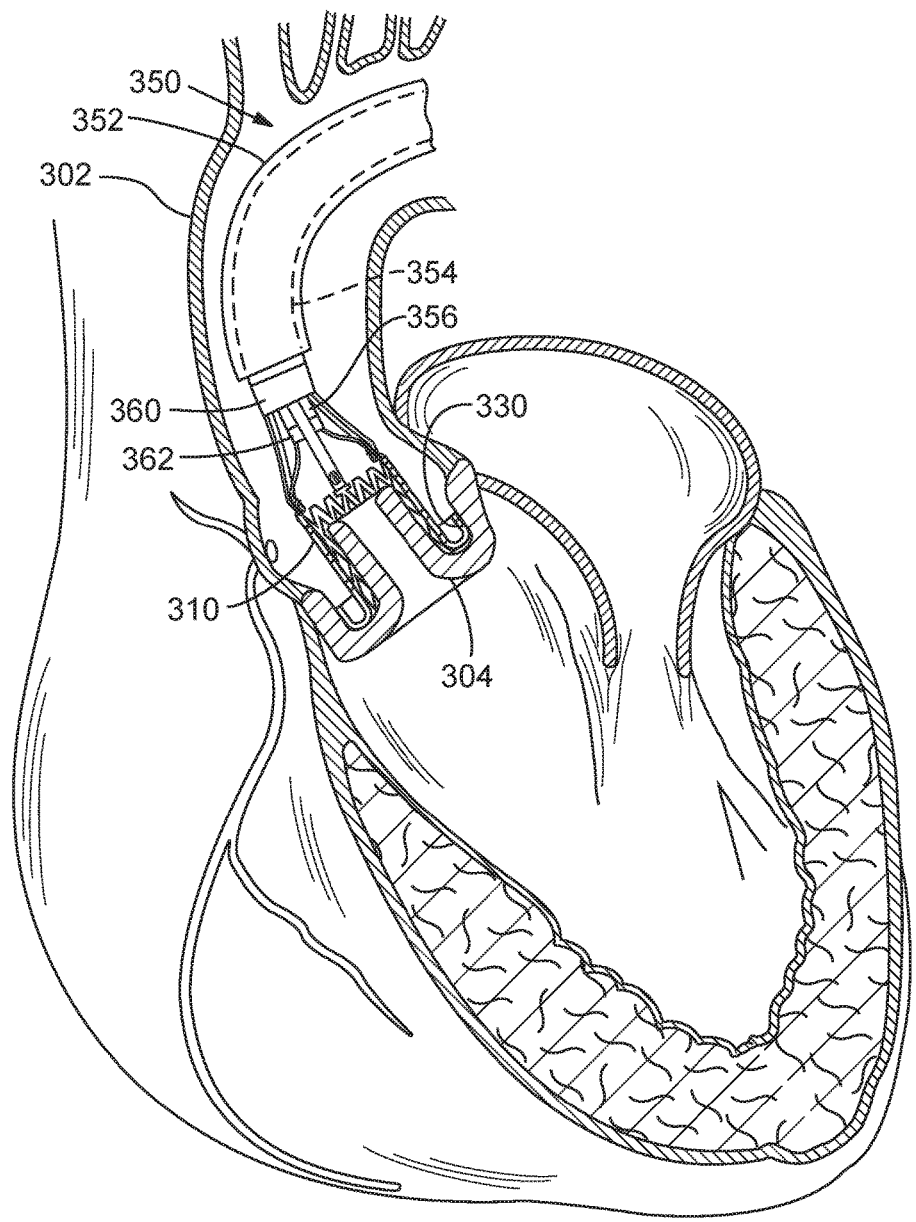
FIG. 17 is a cross-sectional view of a patient's heart illustrating how a delivery system can operate to deploy the support structure of FIG. 14 to a desired position on the patient's aortic valve.
Figure 18:
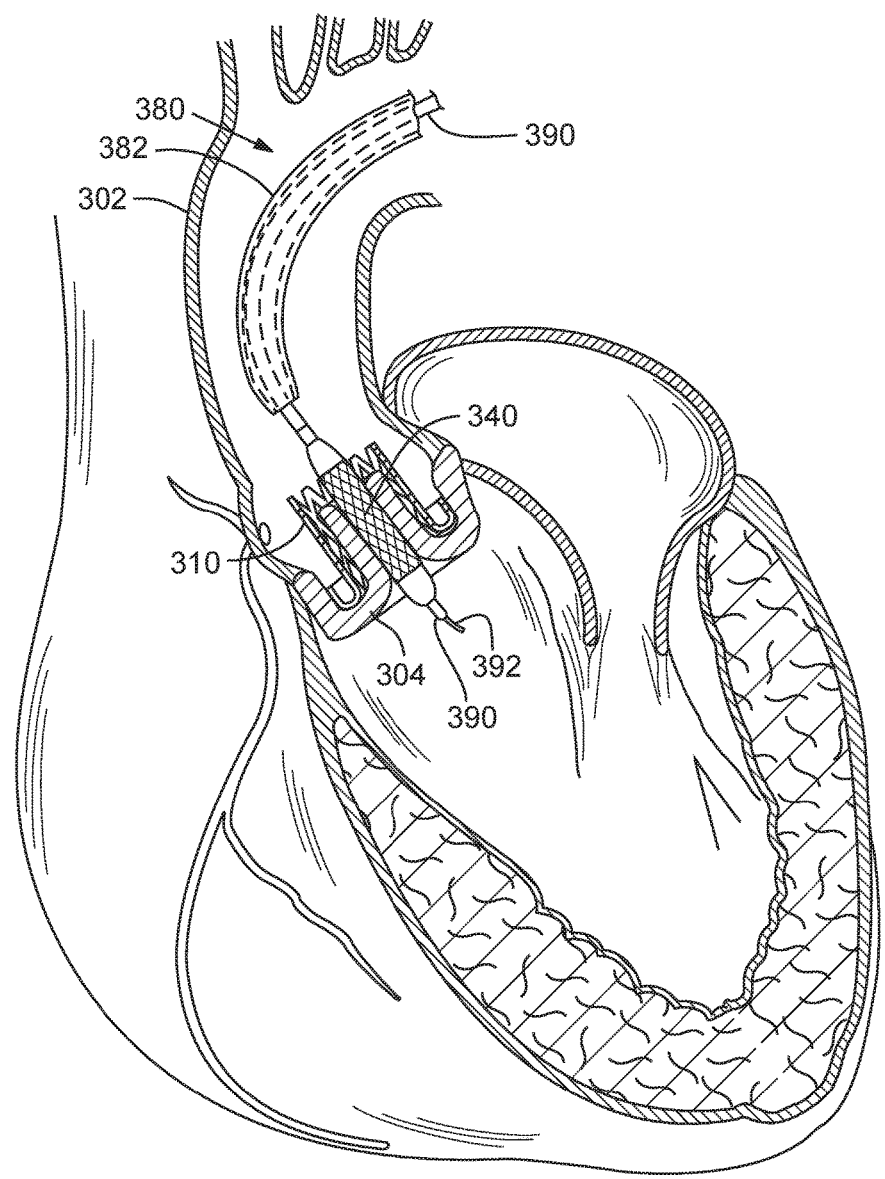
FIG. 18 is a cross-sectional view of a patient's heart illustrating how an exemplary THV can be deployed through the aortic arch and into the patient's aortic valve, where it can be frictionally secured to the native leaflets using the support structure of FIG. 14.

FIGS. 17-18 illustrate one exemplary procedure for deploying the support stent 310 and securing a THV 340 within an interior of the support stent. In particular, FIGS. 17-18 are cross-sectional views through the left side of a patient's heart showing the acts performed in delivering the support stent 310 through the aortic arch to the aortic valve. For the sake of brevity, certain details concerning the delivery system of the THV 340 are omitted. Additional details and alternative embodiments of the delivery system for the THV 340 that may be used with the support stent described herein are discussed in U.S. Patent Application Publication No. 2008/0065011 (U.S. application Ser. No. 11/852,977) and U.S. Patent Application Publication No. 2007/0005131 (U.S. application Ser. No. 11/152,288), which are hereby expressly incorporated herein by reference.

FIG. 17 shows an outer catheter 352 (which can be a guide catheter) of a delivery system 350 as it is advanced through the aortic arch 302 into a position near the surface of the outflow side of the aortic valve 304. The delivery system 350 can be inserted through the femoral artery of the patient and advanced into the aorta in the retrograde direction. FIG. 17 also shows a stent delivery catheter 354, an inner catheter 356, and the support stent 310. Also seen in FIG. 17 are the outer fork 360 and the inner fork 362, which couple the support stent 310 to the distal ends of the stent delivery catheter 354 and the inner catheter 356, respectively.

More specifically, FIG. 17 shows the support stent 310 after it has been advanced through the distal end of the guide catheter 352 and assumes its final, uncompressed shape in a position adjacent to the aortic valve 304. In order to better illustrate the components of the delivery system for the THV, FIGS. 17-18 do not show the entire front side of the support stent 310 or the corresponding valve leaflet that would be secured by the front side of the support stent 310. It is to be understood, however, that in practice the entire support stent 310 would exist and engage a corresponding leaflet of the native heart valve.

The support stent 310 can be positioned adjacent to the aortic valve 304 so that the rim portion 330 of the support stent engages the walls surrounding the aortic valve 304 and exerts an outward force against those walls, thereby securing the support stent 310 within the aorta. This positioning can be achieved, for example, by advancing the guide catheter 352 to a position directly adjacent the aortic valve 304 while the stent delivery catheter 354 and the inner catheter 356 are undeployed and while the support stent 310 remains in its compressed state. The guide catheter 352 can then be retracted while the stent delivery catheter 354 and the inner catheter 356 are held in place, thereby allowing the support stent 310 to expand toward its natural shape. As with the delivery system 100 described above, the position of the guide catheter 352 and the support stent 310 relative to the aortic valve 304, as well as the position of other elements of the system, can be monitored using radiopaque markers and fluoroscopy, or using other imaging systems such as transesophageal echo, transthoracic echo, IVUS, or an injectable dye that is radiopaque.

Once the support stent 310 is positioned into the desired location adjacent the aortic valve 304, the prongs of the inner fork 362 can be disengaged from the corresponding apertures of the retaining arms of the support stent 310. For example, the inner catheter 356 can be retracted into the interior of the stent delivery catheter 354, thereby releasing the support stent 310 from the outer fork 360 and the inner fork 362. The delivery system 350 can then be retracted from the aorta and removed from the patient's body.

With the support stent 310 secured to the aortic valve, a THV (such as any of the THVs discussed above) can be introduced. In contrast to the procedure illustrated in FIGS. 7-13, a delivery system having a delivery catheter that is advanced through the patient's aorta can be used to deliver the THV. In other words, a transfemoral approach can be used. For instance, any of the exemplary systems and methods described in U.S. Patent Application Publication No. 2008/0065011 (U.S. application Ser. No. 11/852,977) or U.S. Patent Application Publication No. 2007/0005131 (U.S. application Ser. No. 11/152,288) can be used with the support stent 310. Alternatively, the transapical approach shown in FIGS. 7-13 can be used.

FIG. 18 shows delivery system 380 comprising an outer catheter 382 (which can be a guide catheter) and a balloon catheter 390 extending through the guide catheter. The balloon catheter 390 has a balloon at its distal end on which the THV is mounted. As with the delivery system 350, the delivery system 380 can be inserted through the femoral artery of the patient and advanced into the aorta in the retrograde direction. FIG. 18 further shows a guidewire 392 that has been first inserted into the patient's vasculature and advanced into the left ventricle. The delivery system can then be inserted into the body and advanced over the guidewire 392 until the THV is positioned within the interior of the aortic valve. As shown, the THV is not only in the interior of the aortic valve 304 but also in the interior of the main body portion of the support stent 310.

FIG. 18 shows the THV 340 in its contracted (or unexpanded) state crimped around the balloon portion of the balloon catheter 390. When the surgeon is satisfied of the proper positioning, the balloon of the balloon catheter 390 can be expanded such that the THV 340 expands and urges the native leaflets of the aortic valve against the support stent 310, thereby securing the THV within the annulus of the aortic valve. Once the THV 340 is properly implanted, the balloon of the balloon catheter 390 is deflated, and the entire delivery system 380 including the balloon catheter is withdrawn over the guidewire 392. The guidewire 392 can then be withdrawn.

Other methods of delivering a support stent and THV to the aortic valve or any other heart valve are also possible. For example, in certain embodiments, the support stent and the THV are delivered surgically to the desired heart valve (e.g., in an open-heart surgical procedure). Furthermore, in certain embodiments in which the support stent and THV are delivered surgically, non-compressible support stents and/or THVs are used.

Exemplary Embodiments for Replacing Mitral Valves

The mitral valve can also suffer from valve insufficiency, which may be desirably treated through the implantation of a prosthetic valve. As with aortic valve insufficiency, mitral valve insufficiency often causes the valve annulus to be dilated and the valve leaflets to be too soft to provide reliable support for securing a prosthetic valve. Accordingly, and according to certain exemplary embodiments of the disclosed technology, it is desirable to use a support structure to help secure a transcatheter heart valve ("THV") within a patient's mitral valve. As with the support stents and frames described above, the mitral valve support structure is desirably positioned on the outflow side of the mitral valve. The THV can be inserted into the interiors of the native mitral valve and the support structure and then expanded such that the mitral valve leaflets are frictionally engaged between the exterior surface of the THV and the interior surface of the support structure. Alternatively, the support structure can be deployed after the THV is positioned and expanded within the mitral valve. The diameter of the support structure can then be adjusted such that the valve leaflets are frictionally engaged against the exterior of the THV. By using a support structure to secure the THV, a smaller THV can be used, thereby making the THV delivery process easier and safer. Furthermore, the use of a support structure protects against displacement of the THV if there is any further dilation of the aortic valve. Moreover, when a support structure is used to secure the THV, the native leaflets function as a sealing ring around the valve that prevents paravalvular leaks.

The support structure for the mitral valve can have a variety of shapes. For example, in some embodiments, the support structure has a sinusoidal shape as with the support stent 110, but in other embodiments does not have a sinusoidal shape or is not otherwise shaped in the z-plane. In further embodiments, the support stent is shaped as a cylindrical band or sleeve. The support frame can also have a more complex structure. In general, any of the shapes and materials used for embodiments of the aortic valve support structures described above can be used for embodiments of the mitral valve support structures and vice versa.

In one exemplary embodiment, the mitral valve support structure is made of a suitable biocompatible material that can be delivered through one or more delivery catheters and formed into a band or loop. For this reason, the structure is sometimes referred to herein as a "support band" or "support loop." The biocompatible material may comprise, for example, nylon, silk, polyester, or other synthetic biocompatible material. The biocompatible material may alternatively comprise a natural material, such as catgut. In still other embodiments, the support structure is formed of a biocompatible shape-memory metal or alloy, such as spring steel, Elgiloy®, or Nitinol.

Figure 23:
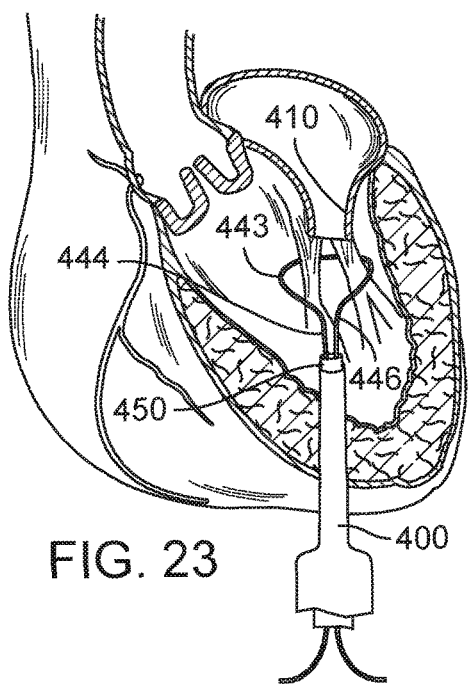
Figure 24:
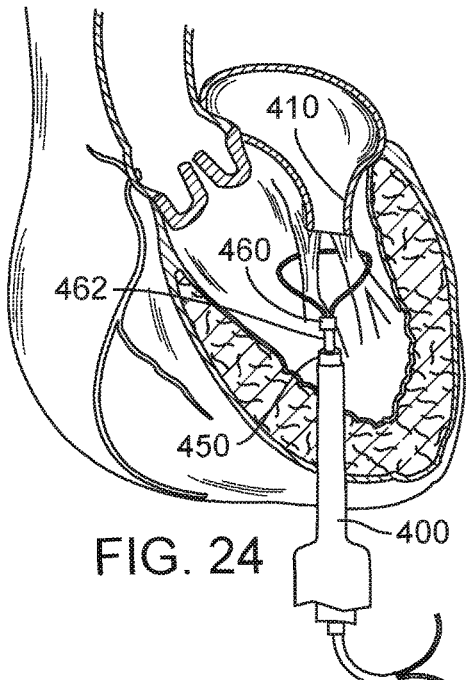
Figure 25:
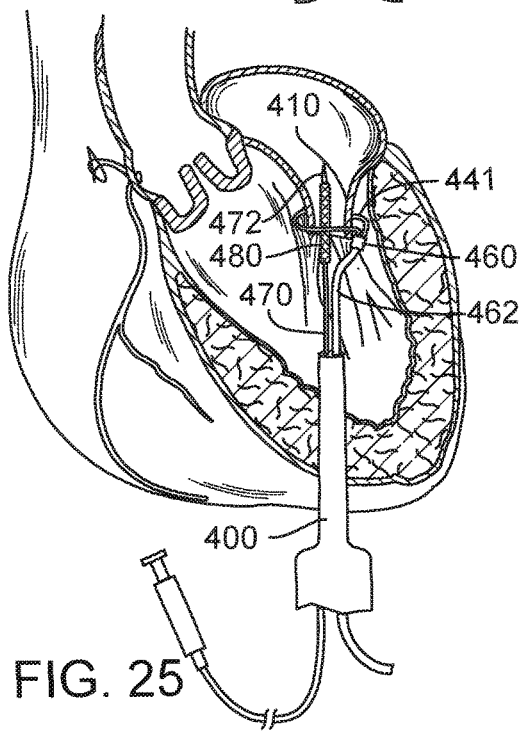
Figure 26:
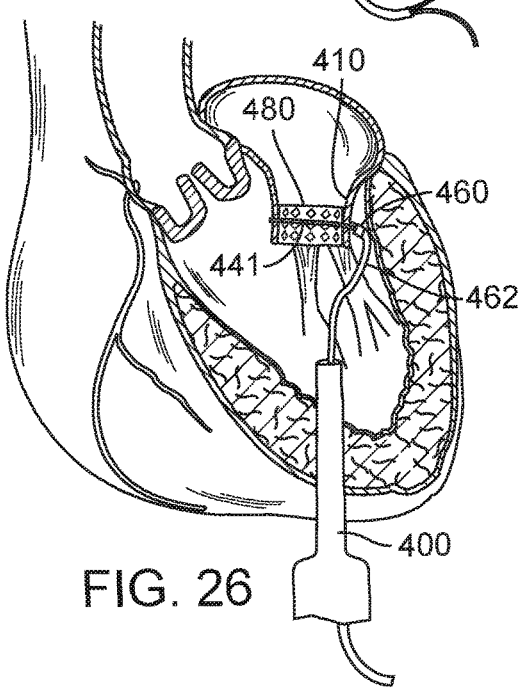
Figure 27:
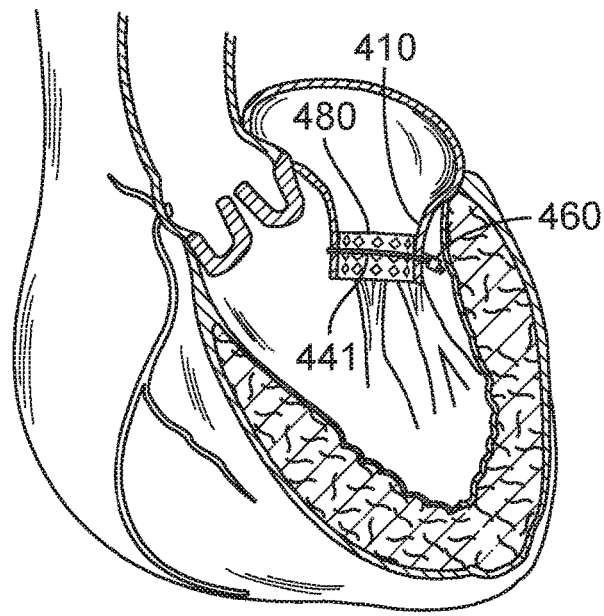

FIGS. 19-27 show one exemplary procedure for delivering a support structure to the mitral valve and having it secure a THV into its desired position within the mitral valve. In particular, FIGS. 19-24 are cross-sectional views through the left side of a patient's heart showing the acts performed in delivering the support structure using a transapical approach. FIGS. 25-27 are cross-sectional views through the left side of a patient's heart showing the acts performed in deploying a THV and having it engage the mitral valve leaflets and the interior of the support structure. It should be noted that FIGS. 19-27 are schematic in nature and thus do not necessarily depict a precise representation of the delivery process. For example, the patient's ribcage is not shown for illustrative purposes and the size of the sheaths used with the delivery system have been altered somewhat in order to better illustrate the procedure. One of ordinary skill in the art, however, will readily understand the range and types of sheaths and catheters that can be used to implement the depicted procedure.

Figure 19:
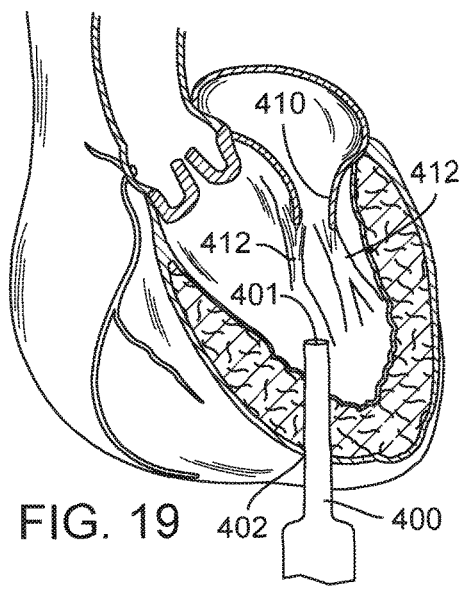
FIGS. 19-27 are cross-sectional view of a patient's heart illustrating how an exemplary support band can be deployed around the native leaflets of a patient's mitral valve and used to secure a THV to the native leaflets of the mitral valve.

FIG. 19 shows an introducer sheath 400 inserted into the left ventricle of a patient's heart through a puncture 402. In particular implementations, the introducer sheath 400 is positioned so that it is not directly centered about the outflow side of the mitral valve, but rather is offset from the center. In particular, the introducer sheath 400 can be positioned so that it is on the exterior side of the space enclosed by chordae tendineae 412. It should be noted that in FIGS. 19-27, the chordae tendineae 412 of the left ventricle are only partially shown. It is to be understood, however, that the chordae tendineae 412 are respectively attached to each of the mitral valve leaflets and to the papillary muscles of the left ventricle. A surgeon can locate a distal tip 401 of the introducer sheath 400 near the outflow side of the mitral valve (e.g., within 1-10 millimeters).

Figure 20:
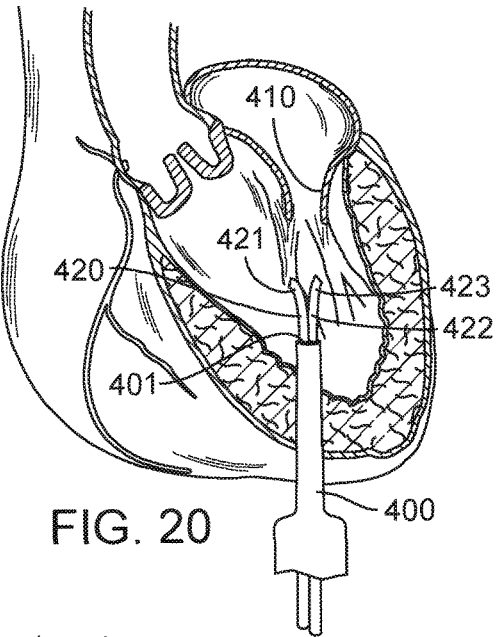

FIG. 20 shows a first catheter delivery sheath 420 and a second catheter delivery sheath 422 being advanced through the interior of the introducer sheath 400. The introducer sheath 400 can define two or more separate lumens through which the first and the second catheter delivery sheaths 420, 422 can be inserted or can define a single lumen sufficiently large to receive both the first and the second catheter delivery sheaths 420, 422. The first and second catheter delivery sheaths 420, 422 can be shaped so that they arc outwardly from each other when advanced out of the distal tip 401 of the introducer sheath 400. For example, in the illustrated embodiment, the first and second catheter delivery sheaths 420, 422 have end regions 421, 423 that arch about 90 degrees (or some other amount, such as between 45-90 degrees) when they are in their natural state. The amount of arching may vary from implementation to implementation but is desirably selected so that the tips of the end portions 421, 423 are in approximately the same plane. In other embodiments, the catheter delivery sheaths 420, 422 are not used as part of the support structure delivery procedure.

Figure 21:
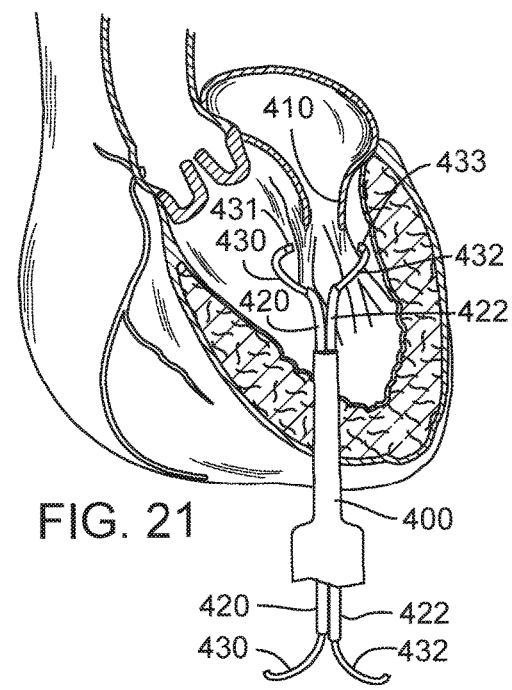

In FIG. 21, a first loop delivery catheter 430 is advanced through the interior of the first catheter delivery sheath 420 and extended substantially around the exterior of one half of the chordae tendineae (e.g., the medial half of the chordae tendineae). Similarly, a second loop delivery catheter 432 is advanced through the interior of the second catheter delivery sheath 422 and extended substantially around the exterior of the other half of the chordae tendineae (e.g., the lateral half of the chordae tendineae). The loop delivery catheters 430, 432 can be steerable catheters having end regions that can be selectively deformed or arched by an operator. Such steerable catheters are well known in the art. The loop delivery catheters 420, 432 can additionally be magnetic or have magnetic distal end portions. For example, in the illustrated embodiment, the first loop delivery catheter 430 has a magnetic distal end portion 431 with a first polarity, and the second loop delivery catheter 432 has a magnetic distal end portion 433 with a second polarity opposite the first polarity. As a result of their magnetization, the end portions 431, 433 are attracted to one another and will form a contiguous junction when in sufficient proximity to each other. Other mechanisms for engaging the end portions 431, 433 to one another are also possible (e.g., a hook mechanism, an adhesive, an enlarged diameter of one end portion, and other such mechanisms). When the end portions 431, 433 are engaged to one another, the first and the second loop delivery catheters 430, 432 form a single interior or lumen through which a support band material can be advanced. Furthermore, when the end portions 431, 433 are engaged to one another, the first and the second loop delivery catheters 430, 432 create a partial loop that circumscribes the chordae tendineae.

Figure 22:
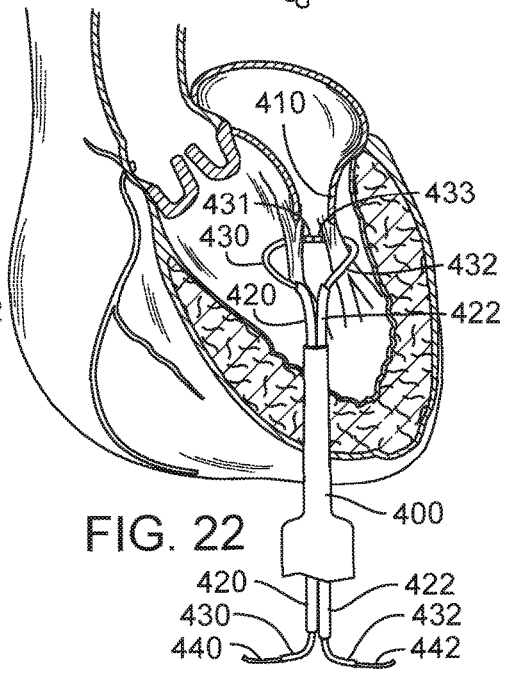

FIG. 22 shows the magnetic distal end portions 431, 433 after the first and second loop delivery catheters 430, 432 are arched around the chordae tendineae and after the distal end portions have been magnetically engaged to one another. In this configuration, a cord 440 of biocompatible material can be advanced through the interior of one of the loop delivery catheters 430, 432 and into the interior of the other one of the loop delivery catheters. As used herein, the term "cord" refers to a slender length of material that can be formed from a single strand, fiber, or filament, or can comprise multiple strands, fibers, or filaments. In one particular implementation, an end 442 of the cord 440 can be advanced from a proximal end of the first loop delivery catheter 430, through the interior of the first loop delivery catheter, through the junction formed by the distal end portions 431, 433, and through the interior of the second loop delivery catheter 432 until it appears on the proximate end of the second loop delivery catheter 432. In one particular embodiment, the cord 440 is a guidewire (e.g., a guidewire made of stainless steel or other suitable metal). The guidewire can then be attached to another cord of biocompatible material used to form the support band and pulled through the interior of the first and the second loop delivery catheters 430, 432, thereby positioning the cord of biocompatible material around the chordae tendineae in a partial loop. With the cord of biocompatible material delivered around the chordae tendineae, the first and second loop delivery catheters 430, 432 and the first and second catheter delivery sheaths 420, 422 can be retracted from the introducer sheath 400.

FIG. 23 shows a cord 443 of biocompatible material used to form the support band positioned around the chordae tendineae after the first and second loop delivery catheters 430, 432 and the first and second catheter delivery sheaths 430, 422 have been withdrawn. In FIG. 23, a sheath 450 is inserted over both ends of the cord 443 and over a first portion 444 and a second portion 446 of the cord 443, which run through the length of the sheath 450.

As shown in FIG. 24, a locking member 460 can be advanced over the first and second portions 444, 446 of the cord 443 and into the left ventricle. The locking member 460 can be advanced, for example, by a pusher tube 462 that pushes the locking member 460 over the portions 444, 446 of the cord 440. In one particular embodiment, the locking member 460 includes lumens or other openings configured to receive each of the two portions 444, 446 and permits movement along the portions 444, 446 in only a single direction. In certain other embodiments, the locking member 460 can be unlocked from the portions 444, 446 of the cord 440 and advanced in both directions along the cord 440. In the illustrated embodiment, the pusher tube 462 is further configured to sever the portions of the cord 440 that extend through a proximal side of the locking member 460, thereby releasing a support band 441 formed by the locking member 460 and the loop-shaped portion of the cord 443 from the pusher tube 462. As more fully shown in FIG. 25, the pusher tube 462 can further be formed of a shape memory material or include a deflection mechanism that allows the pusher tube to have an arched shape toward its distal end. On account of this arched shape, the pusher tube 462 can be used to better position the support band 441 formed by the loop-shaped portion of the cord 443 and the locking member 460 adjacent to the outflow side of the mitral valve such that the native leaflets of the mitral valve open into an interior of the support band 441.

As shown in FIG. 25, the sheath 450 can be withdrawn from the introducer sheath 400 once the locking member 460 and the pusher tube 462 are advanced into the left ventricle. A balloon catheter 470 can be advanced through the introducer sheath 400 and into the interior of the mitral valve 410 of the patient. Although not shown in the illustrated embodiment, the balloon catheter may be guided by a guidewire into the center of the mitral valve. Ultimately, and as seen in FIG. 25, a balloon portion 472 of the balloon catheter 470 around which a THV 480 is crimped can be located within the mitral annulus. Radiopaque markers or other imaging enhancers may be provided on the distal end of the introducer sheath 400 and the balloon catheter 470 to more accurately determine the position of the THV 480 relative to the native valve 410. In some embodiments, a surgeon can adjust the position of the THV 480 by actuating a steering or deflecting mechanism within the balloon catheter 470.

As also shown in FIG. 25, the locking member 460 and the pusher tube 462 can be positioned so as not to interfere with the balloon catheter 470. Furthermore, with the THV 480 properly positioned within the mitral valve 410, the pusher tube 462 can be used to position the support band 441 formed by the loop-shaped remaining portion of the cord 443 around the native valve leaflets of the mitral valve. Radiopaque markers or other suitable imaging enhancers can be provided on the pusher tube 462, the locking member 460, and/or the loop-portion of the cord to allow for the proper positioning of the support band 441 relative to the valve leaflets. With the THV 480 in its desired position, the balloon portion 472 of the balloon catheter 470 can be inflated, thereby expanding the THV 480 against the native valve leaflets and causing the leaflets to frictionally engage the interior surface of the support band 441. This expansion secures the THV 480 to the native valve leaflets. In other words, the expansion pinches the native leaflets of the mitral valve between the support band 441 and the THV 480, and thereby secures the THV within the annulus of the mitral valve.

As shown in FIG. 26, with the THV 480 secured against the native mitral valve leaflets and the support band 441, the balloon portion 472 of the balloon catheter 470 can be deflated and the balloon catheter withdrawn from the introducer sheath 400. The pusher tube 462 can then be disengaged from the loop 441. For example, the pusher tube 462 can comprise a cutting element at its distal end that can be activated by the surgeon from the proximal end. An example of one suitable cutting element is shown below with respect to FIG. 39. Alternatively, a separate cutting device (e.g., a cutting catheter or catheter having a controllable cutting element) can be inserted through the introducer sheath 400 and used to cut the portions of the cord 443 that extend through the proximal side of the locking member 460 and do not form part of the support band 441.

FIG. 27 shows the THV 480 secured within the native mitral valve after the support band 441 has been released from the pusher tube 462 and the pusher tube has been retracted from the introducer sheath 400. It should be noted that the THV 480 can take a variety of different forms and may comprise an expandable stent portion that supports a valve structure. The stent portion desirably has sufficient radial strength to hold the valve at the treatment site and to securely engage the support band 441.

It will be understood by those of ordinary skill in the art that the above-described loop deployment technique can be modified in a number of manners without departing from the disclosed technology. For example, in some embodiments, the THV is delivered and expanded into the mitral valve before the support band is delivered to the left ventricle. In these embodiments, the THV can be temporarily secured within the mitral valve. For example, the THV can be temporarily secured to the mitral valve using one or more anchoring members on the exterior of the THV (e.g., anchoring members having a main body and one or more hook-shaped or umbrella-shaped barbs). The THV can also be temporarily secured within the mitral valve through the use of one or more spring-loaded clamps, rivets, clasps, or other such fastening mechanisms. With the THV temporarily secured, the support band can be delivered around the native leaflets as described above and the diameter of the support band reduced until a desired frictional fit is created between the support band, the leaflets, and the THV. Any of the locking members described herein that allow the diameter of the support band to be adjusted can be used to achieve the desired diameter.

Figure 28:
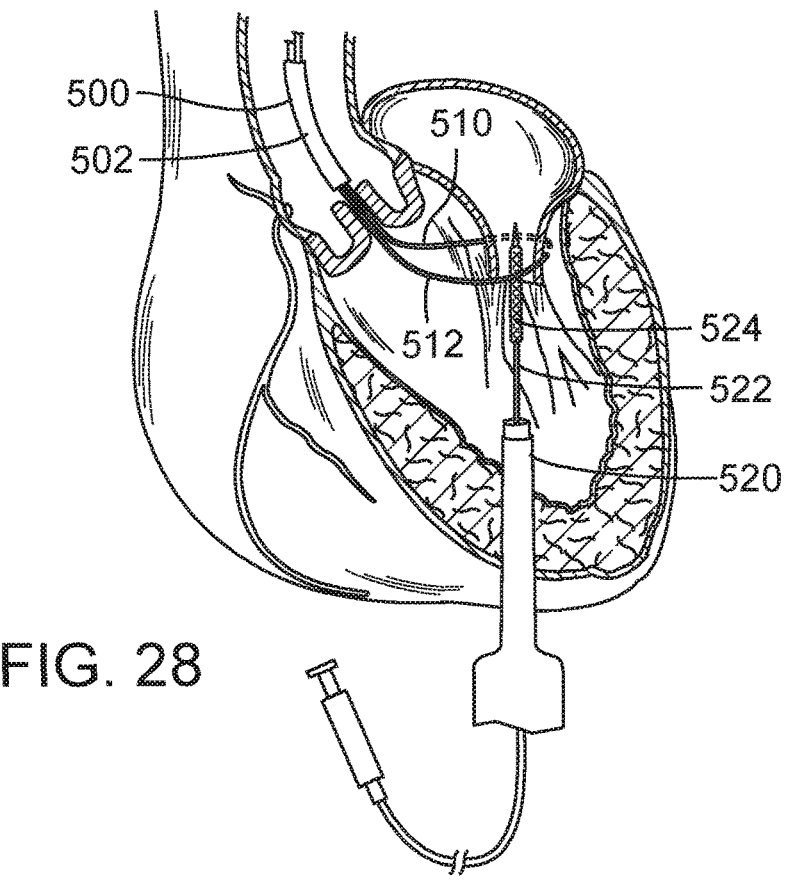
FIG. 28 is a cross-sectional view of a patient's heart illustrating how an exemplary support band as in FIGS. 19-27 can be deployed through the aortic arch.

Further, although the delivery method shown in FIGS. 19-27 uses a transapical approach, a delivery system adapted for introduction through the patient's aortic arch can alternatively be used. FIG. 28 shows an example of such a delivery system 500. In particular, FIG. 28 shows the delivery system 500 after a delivery catheter has been advanced through the aortic arch to a position adjacent the aortic valve and as a first loop delivery catheter 510 and a second loop delivery catheter 512 are deployed through the distal end of a delivery catheter 502. As with the procedure described above, the first and second loop delivery catheters 510, 512 can be steerable and comprise magnetic distal end portions that allow the catheters 510, 512 to engage one another on a distal side of the chordae tendineae, thereby forming a delivery lumen through which biocompatible material for the support band or loop can be deployed. Also shown in FIG. 28 is an introducer sheath 520 and a balloon delivery catheter 522 for deploying a THV 524. Besides the adaptations for aortic delivery, the delivery procedure can otherwise be substantially similar or identical to the procedure shown in FIGS. 19-27.

Still other delivery variations are possible. For instance, the support band may be formed of a shape-memory material that assumes a C-shape when not acted on by any external forces. The support band can be further configured such that one end of the C-shaped member is hollow and has a slightly larger diameter than the opposite end. To deliver the C-shaped support band, the support band can be stretched into a linear form and advanced through a delivery catheter (e.g., using a pusher element). In particular, the distal end of the delivery catheter can be positioned adjacent the chordae tendineae such that when the support band is advanced out of the distal end, it wraps around the chordae tendineae. After the support band is deployed from the distal end of the delivery catheter, a clamping device that is designed to engage the C-shaped support band and urge the ends of the support band together can be inserted into the heart (e.g., through the delivery catheter, the introducer sheath, or through a separate catheter). The clamping device can be used to urge one end of the support band into the hollow opposite end of the band. The ends can be crimped so that the support band forms a ring-shaped support band (e.g., using the clamping device or other device). In other embodiments, the hollow end of the support band can comprise a shoulder that engages an angled collar on the other end of the support band when the ends are urged together, thereby form a snap-fit connection. With the ends of the support band secured to one another, the support band can be positioned around the native leaflets of the mitral valve (e.g., using the clamping device or other positioning device) as a balloon catheter delivers a THV. Upon expansion, the THV will pinch the native valve leaflets between the outer surface of the THV and the interior surface of the support band, thereby securing the THV within the mitral valve.

In still another embodiment, the support band includes one or more clamping or fastening devices that can be used to clamp or fasten the support band to the native leaflets of the mitral leaflets. For example, the clamping or fastening devices can comprise spring-loaded clamps, anchoring members having one or more hook or umbrella-shaped barbs, clasps, or other such clamping or fastening mechanisms. In this embodiment, the support band still has a substantially fixed diameter such that when the THV is expanded into the interior of the mitral valve, the THV causes the native valve leaflets to be pinched against the interior surface of the support band, thereby securing the THV within the mitral valve. In still other embodiments, the THV itself can include one or more clamping or fastening devices designed to clamp or fasten the THV to the native leaflets of the mitral valve (e.g., any of the clamping or fastening mechanisms described above). In this embodiment, the THV can be secured directly to the native leaflets without the use of a support band or other support structure.

Figure 29:
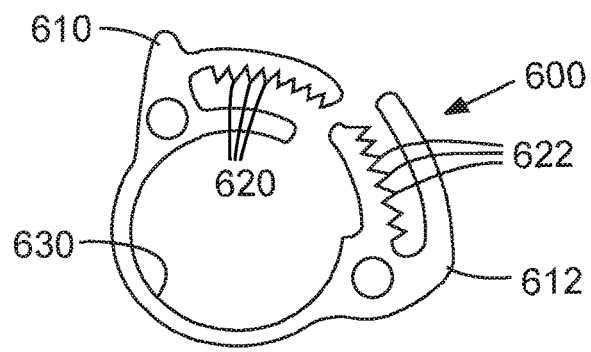
FIG. 29 is a top view of an exemplary locking member that can be used to secure portions of a cord of support band material to one another and thereby form a loop.

FIG. 29 shows one exemplary embodiment of a locking member that can be used for locking member 460 shown in FIGS. 19-27. In particular, FIG. 29 shows locking member 600, which can be a clamp, such as an adjustable, C-shaped clamp with interlocking teeth around a portion of the clamp. The locking member 600 has two arms 610, 612, each formed with interlocking teeth 620, 622. Interlocking teeth 620, 622 are configured to lock the clamp in one or more positions of varying circumference when pressure is applied to the two arms 610, 612 and pushes the arms together. Referring to FIG. 23, the cord portions (such as portions 446, 446) can be inserted into the interior 630 of the locking member 600. The arms 610, 612 can be pushed together and tightened so that the portions 444, 446 are secured in place (e.g., using a clamping device inserted into the left ventricle through the introducer sheath or using the pusher tube 462 modified to include a clamping mechanism). The interior 630 can additionally have grooves to increase the friction and decrease the slippage between the locking member 600 and the portions of the cord secured therein.

Figure 30:
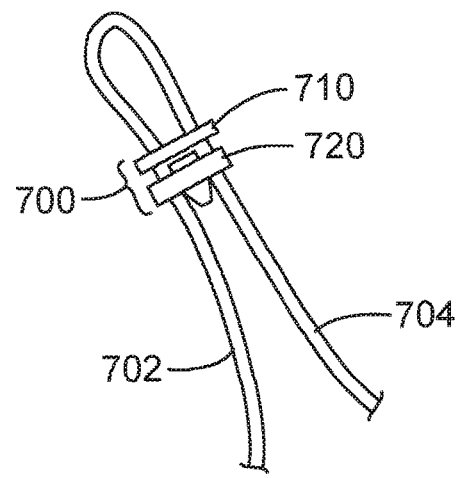
FIG. 30 is a top view of another exemplary locking member that can be used to secure portions of a cord of support band material to one another and thereby form a loop.
Figure 31:
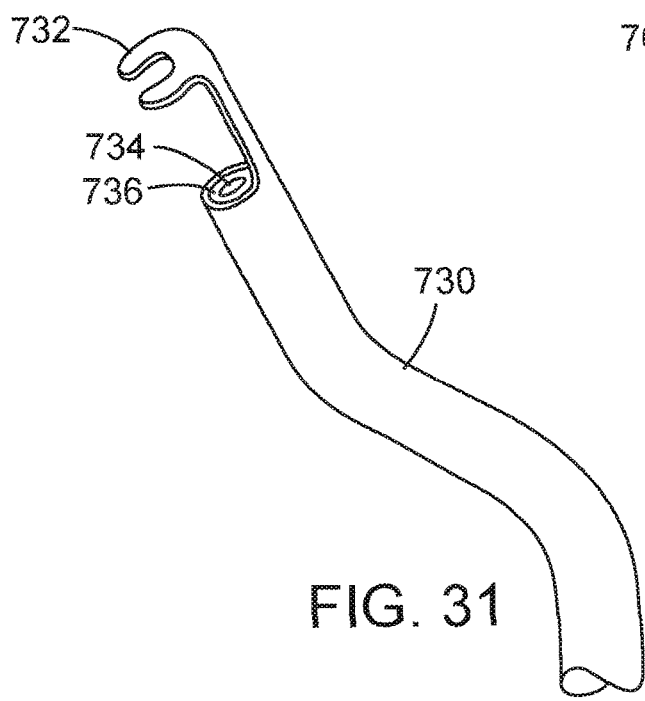
FIG. 31 is a perspective view of an exemplary adjustment tool (or pusher tube) that can be used in connection with the locking member of FIG. 30.
Figure 32:
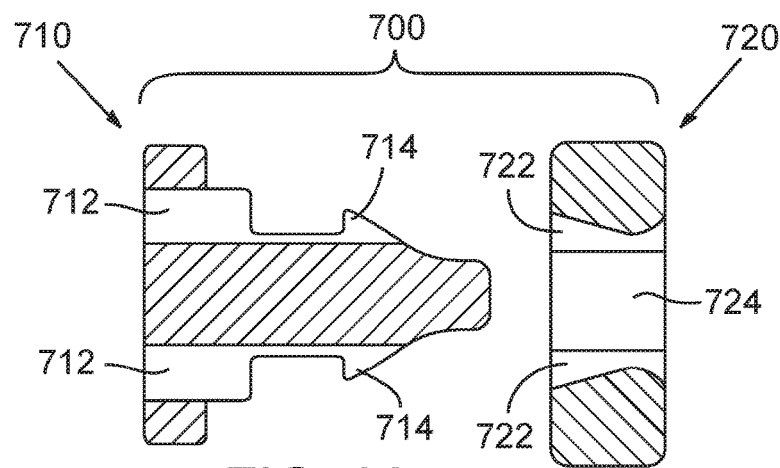
FIG. 32 is a cross-sectional side view of the exemplary locking member of FIG. 30.

FIGS. 30-37 depict another exemplary embodiment of a locking member that can be used for locking member 460 shown in FIGS. 19-27. In particular, FIGS. 30-37 show an adjustable locking member 700, which can be attached to two portions of a cord, thereby forming the support band. As best seen in FIGS. 30 and 32, the adjustable locking member 700 comprises a tapered, plastic pin 710 that fits into a tapered, plastic snap ring 720. When pin 710 and ring 720 are locked together, the adjustable locking member 700 is prevented from moving relative to the portions of the cord that are captured within the adjustable locking member 700 (e.g., cord portions 702, 704 in FIG. 30).

FIG. 31 illustrates an exemplary pusher tube (or adjustment catheter) 730 that can be used to introduce, position, and lock the adjustable locking member 700 in a desired position. The exemplary pusher tube 730 in the illustrated configuration has a fork member 732, an unlocking push member 734 that is extendable through the fork member 732, and a locking push member 736 that is extendable over the unlocking push member 734. Fork member 732 is configured so that it can move the adjustable locking member 700 over the cord portions to which it is connected. In particular, fork member 732 can engage the adjustable locking member 700 when it is positioned along the cord portions (but not yet in a locked position) such that by moving the pusher tube 730 in one direction along the length of the cord portions, adjustable locking member 700 is also moved. By moving the adjustable locking member 700 in this manner, the effective diameter of the support band formed by the cord and the adjustable locking member 700 can be modified.

Push members 734, 736 are slidably movable relative to each other and the fork member 732 to effect locking and unlocking of the adjustable locking member 700, as further described below. The unlocking push member 734 unlocks the adjustable locking member 700 from the locked position and the locking push member 736 locks the adjustable locking member 700 from the unlocked position.

FIG. 32 depicts the adjustable locking member 700, according to one embodiment, in more detail. The pin 710 comprises pin slots or holes 712 (which accept the cord portions) and locking members or flanges 714 (which extend outward to secure the pin to the ring in a locked position). Ring 720 comprises ring slots or holes 722 (which accepts the cord portions) and pin receiving hole 724 (which receives the pin to secure the pin to the ring in a locked position). The locking members 714 are deformable to allow the pin member to be inserted throughout ring member and form a snap-fit connection sufficient to hold the ring member on the pin member.

Figure 33:
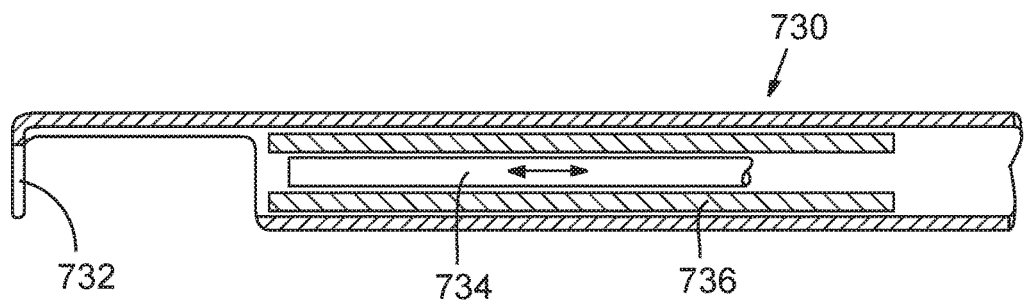
FIG. 33 is a cross-sectional side view of the exemplary adjustment tool of FIG. 31.

FIGS. 33-37 depict the relationship between the adjustable locking member 700 and the pusher tube 730, according to one embodiment, and their functions relative to one another. As discussed above, the pusher tube 730 comprises fork member 732, unlocking push member 734, and locking push member 736. FIG. 33 shows the pusher tube 730 in more detail. Both the unlocking push member 734 and the locking push member 736 are slidably movable within the pusher tube 730 along the longitudinal direction identified by the arrows shown in FIG. 33. The unlocking push member 734 is desirably a solid member that is sized to fit within the locking push member 736, which is desirably cylindrical with a longitudinally extending hollow section or lumen for receiving the unlocking push member 734.

Figure 34:
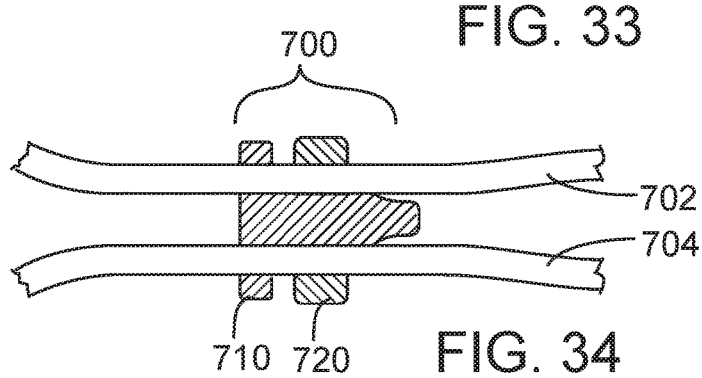
FIGS. 34-37 are cross-sectional views illustrating how the exemplary adjustment tool of FIG. 31 can be used to adjust, lock, and unlock the exemplary locking member of FIG. 30.

FIG. 34 shows the adjustable locking member 700 with the pin 710 and the ring 720 locked together. In the locked position, the cord portions 702, 704 pass inside the ring 720 and around the pin 710 (through the ring holes and pin holes) and are captured between these two components. The cord portions 702, 704 are held in place relative to each other, and the pin 710 and the ring 720 are held in place relative to the cord portions 702, 704 by the friction created at the surface interfaces.

Figure 35:
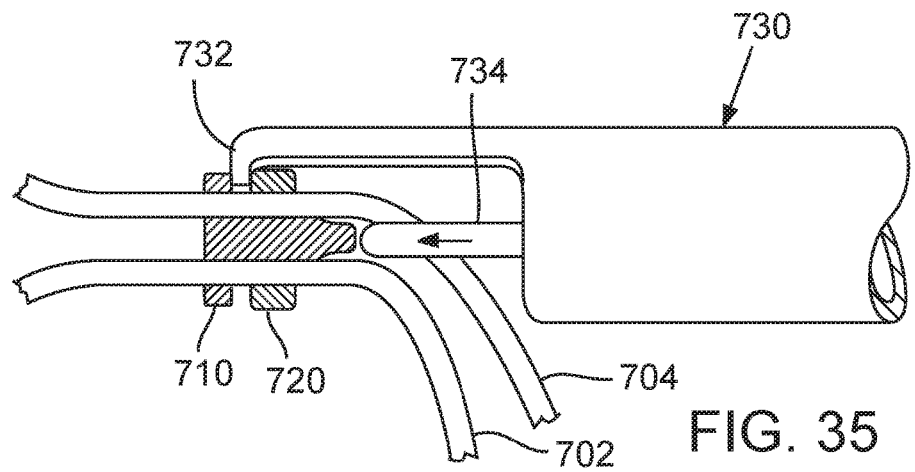
Figure 36:
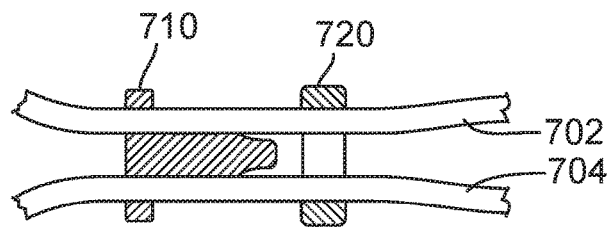

Referring to FIGS. 35 and 36, to unlock the adjustable locking member 700, the fork member 732 is inserted between the pin 710 and the ring 720, and the unlocking push member 734 is extended from the pusher tube 730 to push the pin 710 and the ring 720 apart. The fork member 732 holds the ring 720 in place, while the unlocking push member 734 applies longitudinal pressure against the tip of the pin 710, forcing it out of the ring 720. The unlocking push member 734 is desirably sized so that it can fit at least partially through the pin receiving hole 724 to assist in unlocking the pin 710 and the ring 720 from one another. Once the pin 710 and the ring 720 are separated, the adjustable locking member 700 can be moved relative to the cord portions 702, 704 in order to adjust the diameter of the support band formed by the cord portions 702, 704.

Figure 37:
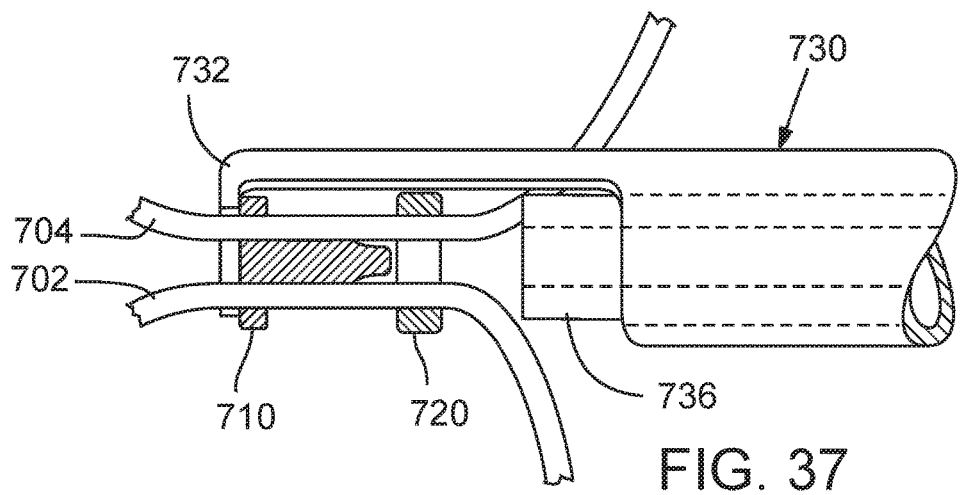

Referring to FIG. 37, the manner in which the pusher tube 730 can be used to secure the pin 710 and the ring 720 together is shown. The fork member 732 is placed at the far (distal) end of the pin 710 and the locking push member 736 is extended from the pusher tube 730. The locking push member 736 is configured with a cylindrical surface that is sized to mate with the area of the ring 720 that surrounds the pin receiving hole. While the fork member 732 holds the pin 710 in place, the locking push member 736 forces the ring 720 onto the pin 710 and locks the pin and the ring together. Once the adjustable locking member 700 is locked, the frictional engagement of the adjustable locking member with the cord portions maintains the position of the adjustable locking member relative to the cord portions 702, 704. The three-point connection system described above permits a surgeon to perform fine adjustments of the diameter of the support band around the chordae tendineae and around the outflow side of the native leaflets of the mitral valve.

Figure 38:
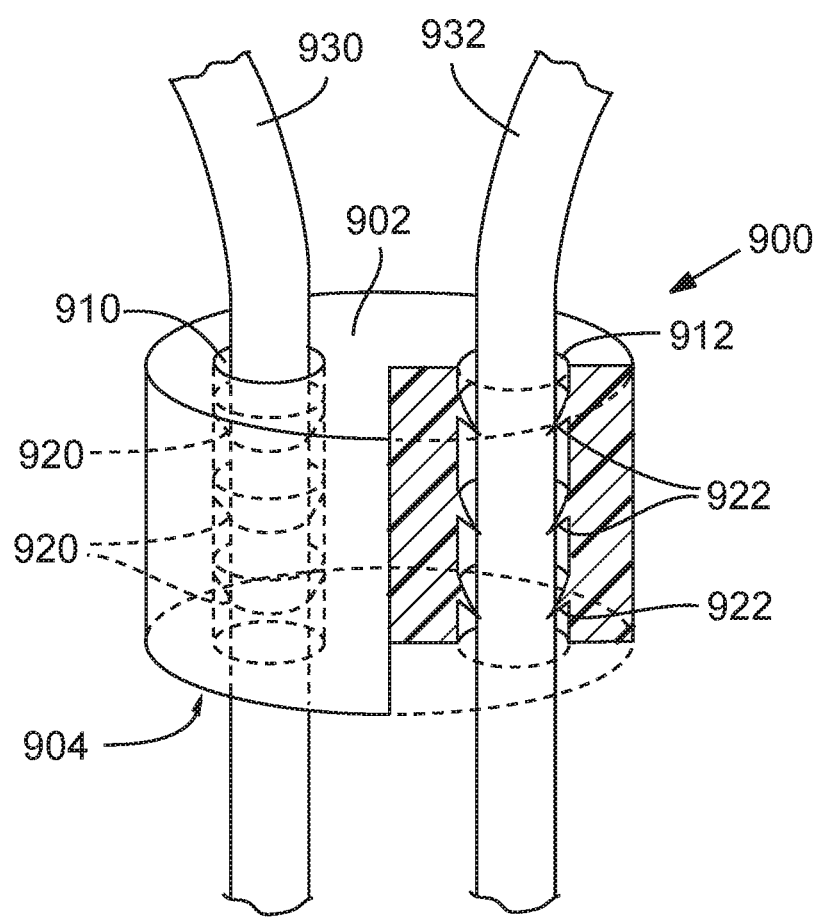
FIG. 38 is a cross-sectional perspective view of another exemplary locking member that can be used to secure portions of a cord of support band material to one another and thereby form a loop.
Figure 39:
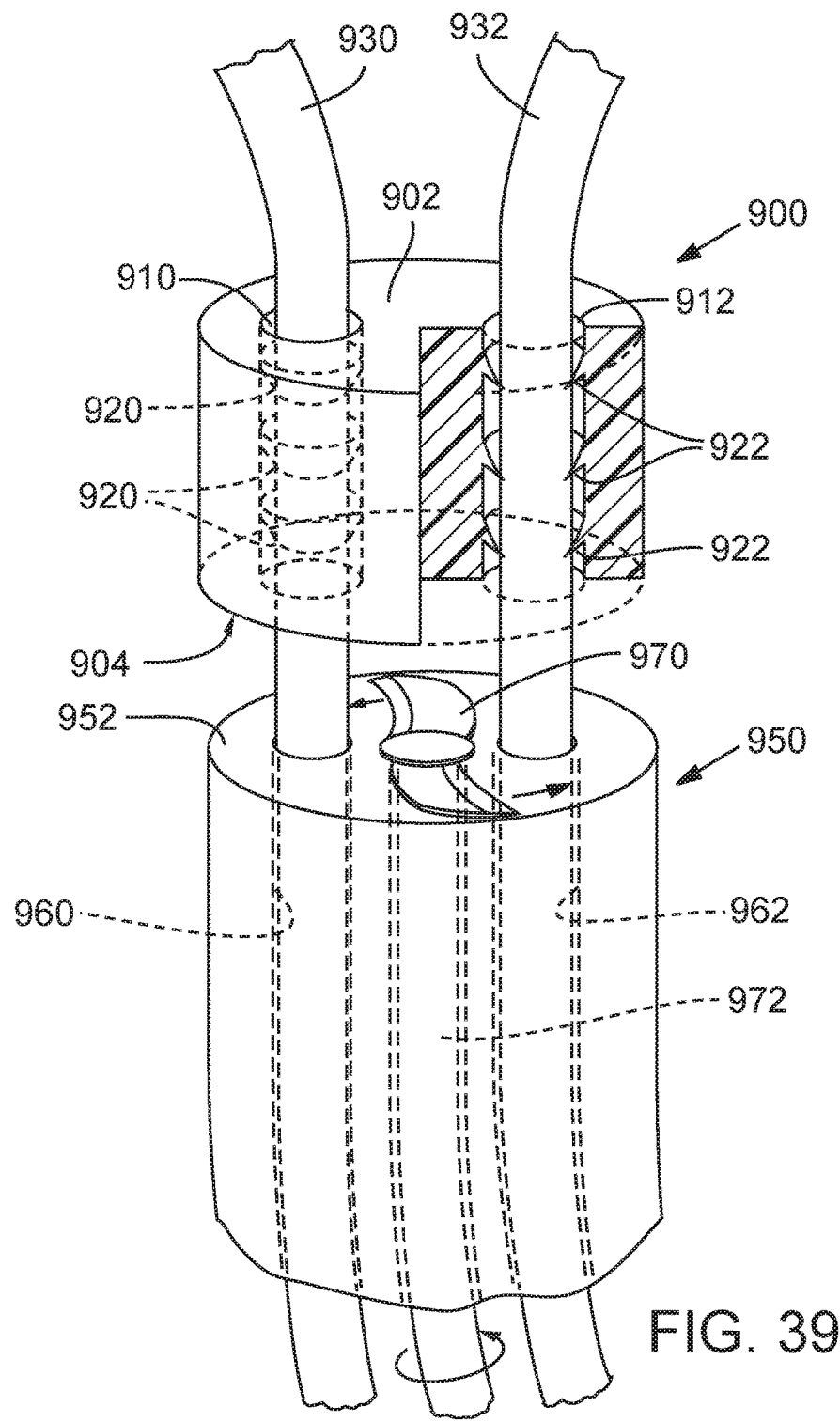
FIG. 39 is a cross-sectional perspective view of an exemplary pusher tube that can be used in connection with the exemplary locking member of FIG. 38.

FIGS. 38-39 depict another exemplary embodiment of a locking member that can be used for locking member 460 shown in FIGS. 19-27. In particular, FIG. 38 shows an adjustable locking member 900 having a generally cylindrical body with two lumens (or apertures) 910, 912 formed therein that extend from a top surface 902 to a bottom surface 904 of the body. In the illustrated embodiment, and as best seen in the cut-away portion of FIG. 38 showing the lumen 912, the interior of the lumens 910, 912 comprises a plurality of teeth (or collars) 920, 922 that are angled toward the bottom surface 904. The teeth 920 can have some flexibility and be formed to allow a cord portion, such as cord portion 930 or cord portion 932, to slide through the lumens 910, 912 in a first direction, but not in an opposite second direction. In other words, the teeth 920, 922 of the adjustable locking member 900 allow for one-way movement of the locking member 900 along the cord portions 930, 932. In this way, the adjustable locking member 900 can be used to securely form the support band and allows for the diameter of the support band to be adjusted to its desired size.

FIG. 39 shows an exemplary embodiment of a pusher tube 950 that can be used with the adjustable locking member 900 (e.g., the pusher tube 950 can be used as the pusher tube 462 shown in FIGS. 19-27). The exemplary pusher tube 950 includes lumens 960, 962 through which the cord portions 930, 932 can extend. In a particular embodiment, the lumens 960, 962 have a sufficiently large diameter and a smooth interior that allows the cord portions 930, 932 to more easily slide therethrough. In the illustrated embodiment, the pusher tube 950 further includes a rotatable blade 970 at its distal end 902. The rotatable blade 970 can be rotatable about a central axis of the pusher tube 950 and connected to an interior rod member 972 that extends through a central lumen of the pusher tube 950. A handle (not shown) can be attached to the interior rod member 972 at its proximal end and allow for an operator to manually rotate the rotatable blade 970 in order to sever the pusher tube 950 from the adjustable locking member 900.

Another system and method for delivering a support band (support loop) that at least partially encircles the chordae tendineae and/or native leaflets of a mitral valve is shown in FIGS. 40-47. As described in other embodiments herein, the support band is preferably positioned on the outflow side of the mitral valve and, after a THV is expanded within the valve, the native valve leaflets are frictionally engaged and in contact with an exterior surface of the THV and an interior surface of the support band. As described in more detail below, a method for positioning a support band around the native leaflets of a valve can include directing a guidewire around the native leaflets, delivering a support member over the guidewire, and securing a locking member to both ends of the support member to form the support band.

Figure 40:
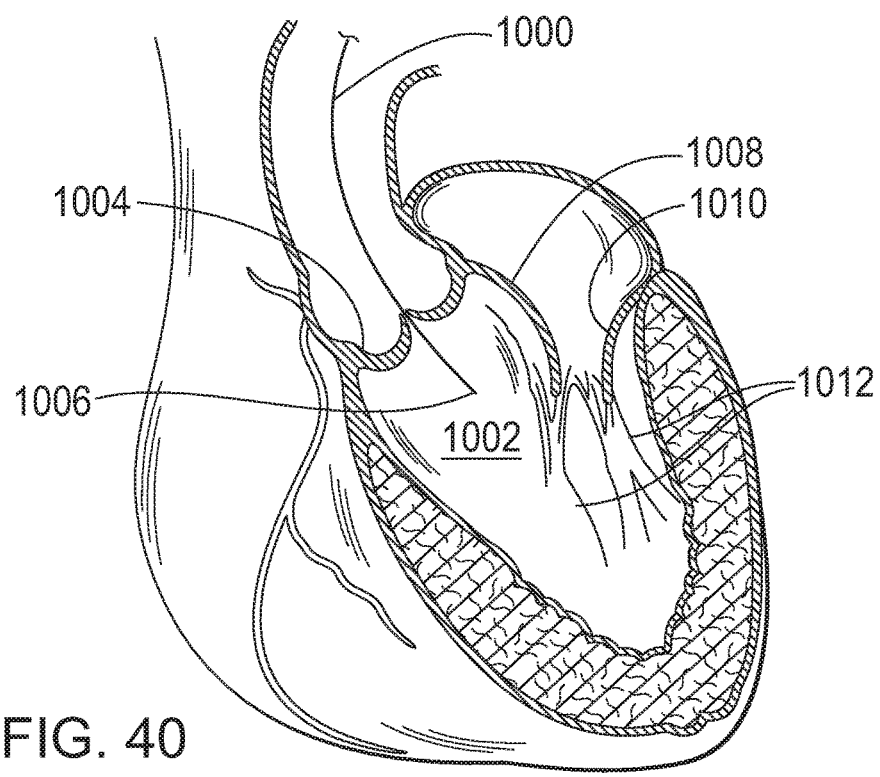
FIG. 40 is a cross-sectional view of a patient's heart illustrating the delivery of a guide wire into a left ventricle.
Figure 41:
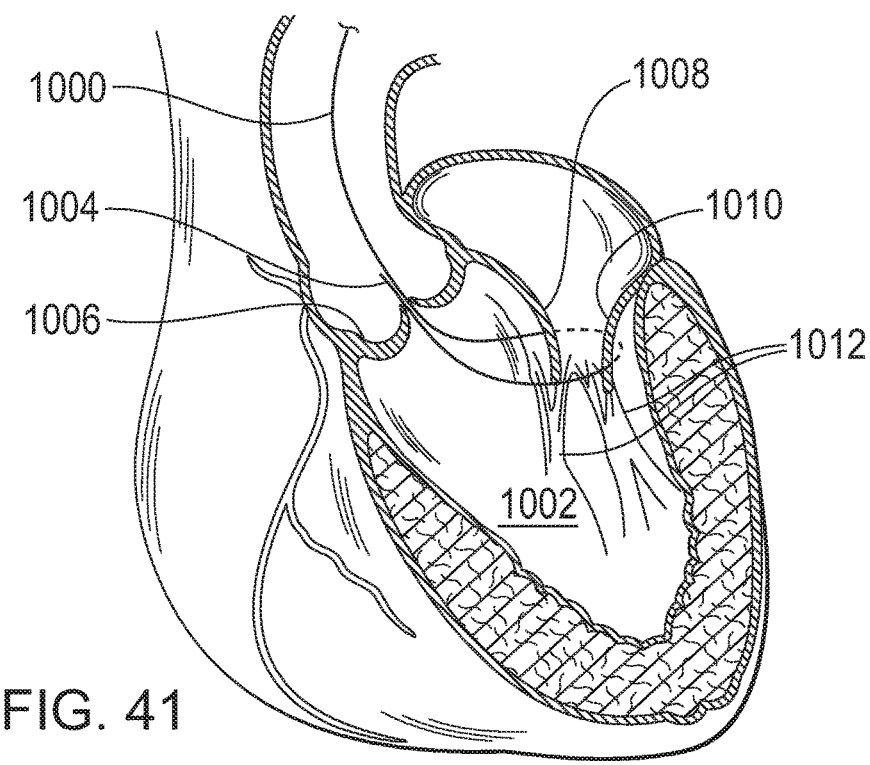
FIG. 41 is a cross-sectional view of a patient's heart illustrating a guide wire positioned to at least partially surround leaflets of a native valve.

To facilitate delivery of the support band to a position where it generally surrounds the native valve leaflets of the mitral valve, a guidewire 1000 can be advanced into a left ventricle 1002 of the patient's heart. FIG. 40 illustrates a guidewire 1000 being advanced through the aortic arch and the aortic valve annulus 1004, and into the left ventricle 1002. As shown in FIG. 41, a distal end 1006 of the guidewire 1000 can be advanced around first and second native leaflet 1008, 1010 and the chordae tendineae 1012, so that guidewire 1000 at least partially surrounds the native leaflets.

Figure 42A:
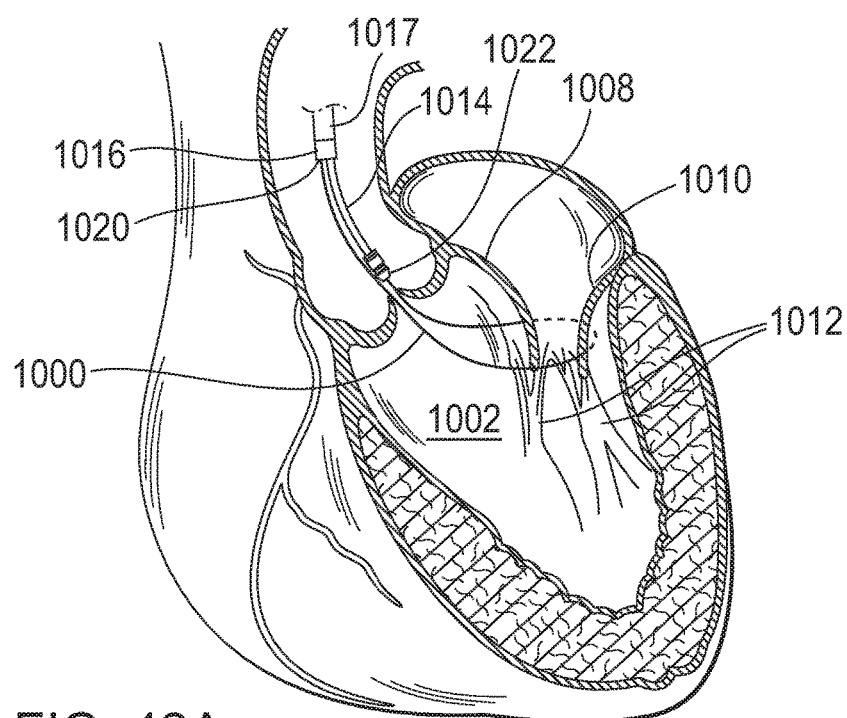
FIG. 42A is a cross-sectional view of a patient's heart illustrating the delivery of a support member over a guide wire.

A support member 1014 can be delivered over the wire 1000 as shown in FIG. 42A. The support member 1014 can comprise a generally cylindrical member with an opening (lumen) that extends along its length so that the support member can be delivered over guidewire 1000. Support member 1014 can be constructed of any suitable biocompatible material that can be delivered through one or more delivery catheters and formed into a band or loop as discussed herein. The biocompatible material may comprise, for example, nylon, polyester, or other synthetic biocompatible material. In still other embodiments, the support member can be formed of a biocompatible shape-memory metal or alloy, such as spring steel, Elgiloy®, or Nitinol.

In one particular embodiment, support member 1014 comprises a braided tube. The braided tube can comprises stainless steel with a PET/Cotton coating. The size of support member 1014 can vary; however, in a preferred embodiment, the outer diameter of support member 1014 is preferably between about 0.5 and 2 mm, and more preferably between 1 and 1.5 mm, and even more preferably about 1.3 mm.

Figure 42B:
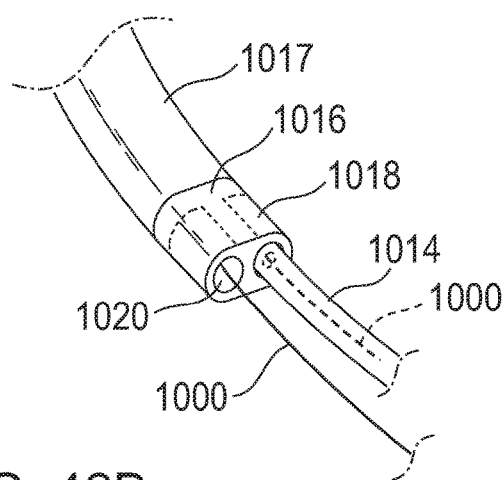
FIG. 42B is an enlarged view of a locking member shown in FIG. 42A.

As shown in FIG. 42B, a locking member 1016 can be secured to a proximal end 1018 of support member 1014 using any suitable securing mechanism. For example, an adhesive and/or mechanical fixation device can be provided to chemically and/or mechanically secure proximal end 1018 to locking member 1016. The proximal end 1018 can be secured to locking member 1016 before support member 1014 and locking member 1016 are introduced into the patient's body.

Alternatively, the proximal end 1018 can be secured to locking member 1016 after support member 1014 and locking member 1016 are introduced into the patient's body. For example, the locking member 1016 can be introduced into the body first, and support member 1014 can be introduced into the body and advanced (e.g., pushed) through locking member 1016. In such a case, a distal end of support member 1014 can be configured to pass entirely through locking member 1016, while proximal end 1018 is configured to engage with an inner surface of the locking member 1016 to restrict further distal movement of support member 1014 through locking member 1016.

Locking member 1016 can also comprise a receiving area 1020 that is configured to receive a distal end 1022 (FIG. 42A) of support member 1014. Distal end 1022 and receiving area 1020 are preferably configured to have a complementary mating configuration that causes distal end 1022 to be securely engaged within receiving area 1020, such as that shown in FIG. 44 and discussed below.

Referring again to FIG. 42A, in operation, guidewire 1000 can be maneuvered at least partially around the native leaflets and then support member 1014 can be delivered over guidewire 1014 into the left ventricle. Preferably, the distal end portion of guidewire 1000 is moved into and/or through receiving area 1020 to form a loop around the native leaflets (as shown in FIG. 42A) to facilitate the delivery of distal end 1022 over the guidewire 1000 and into receiving area 1020. To facilitate entry of the guidewire 1000 a snare catheter (see, for example, FIG. 54) can be delivered through or adjacent to receiving area 1020 to capture and retrieve the distal end of guidewire 1000 and pull it into receiving area 1020. As support member 1014 is advanced over guidewire 1000, distal end 1022 advances around the native leaflets (tracking the path of guidewire 1000) and returns towards receiving area 1020 of locking member 1016 to form a loop around the native leaflets.

To facilitate advancement of support member 1014, a pushing member 1017 (e.g., a catheter or tube) can be positioned proximal to the locking member 1016. Pushing member 1017 can be moved distally to advance support member 1014 over guidewire 1000 to push or otherwise advance support member over guidewire 1000. Pushing member 1017 can be separate from locking member 1016 or it can be removable coupled to locking member 1016 so that it engages locking member 1016 while pushing locking member 1016 distally, but can be disengaged from locking member 1016 after the support member 1014 is in the desired position and/or the support band is formed.

Figure 43:
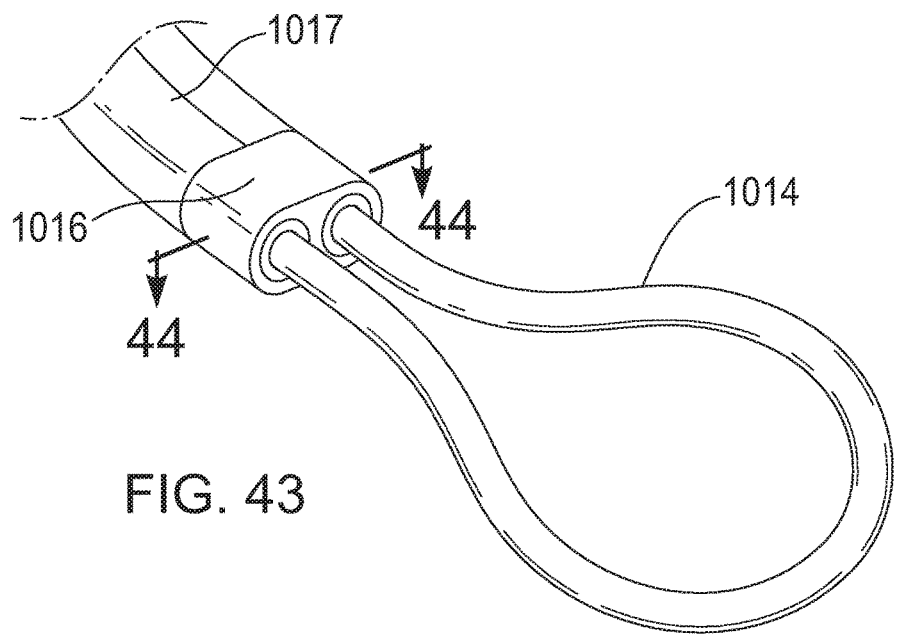
FIG. 43 is an enlarged view of a support band formed by a locking member and a support member.
Figure 44:
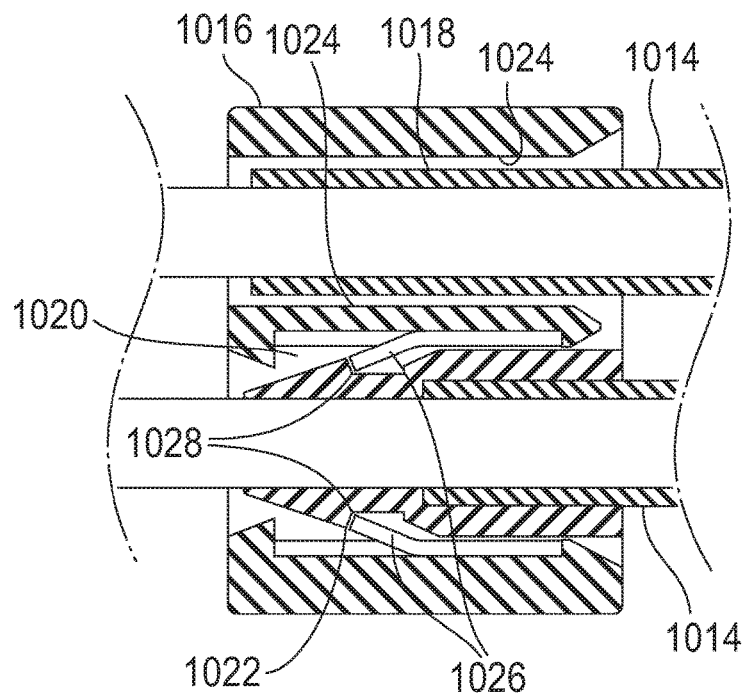
FIG. 44 is a cross-sectional view of the locking member shown in FIG. 43, taken along line 44-44.
Figure 45:
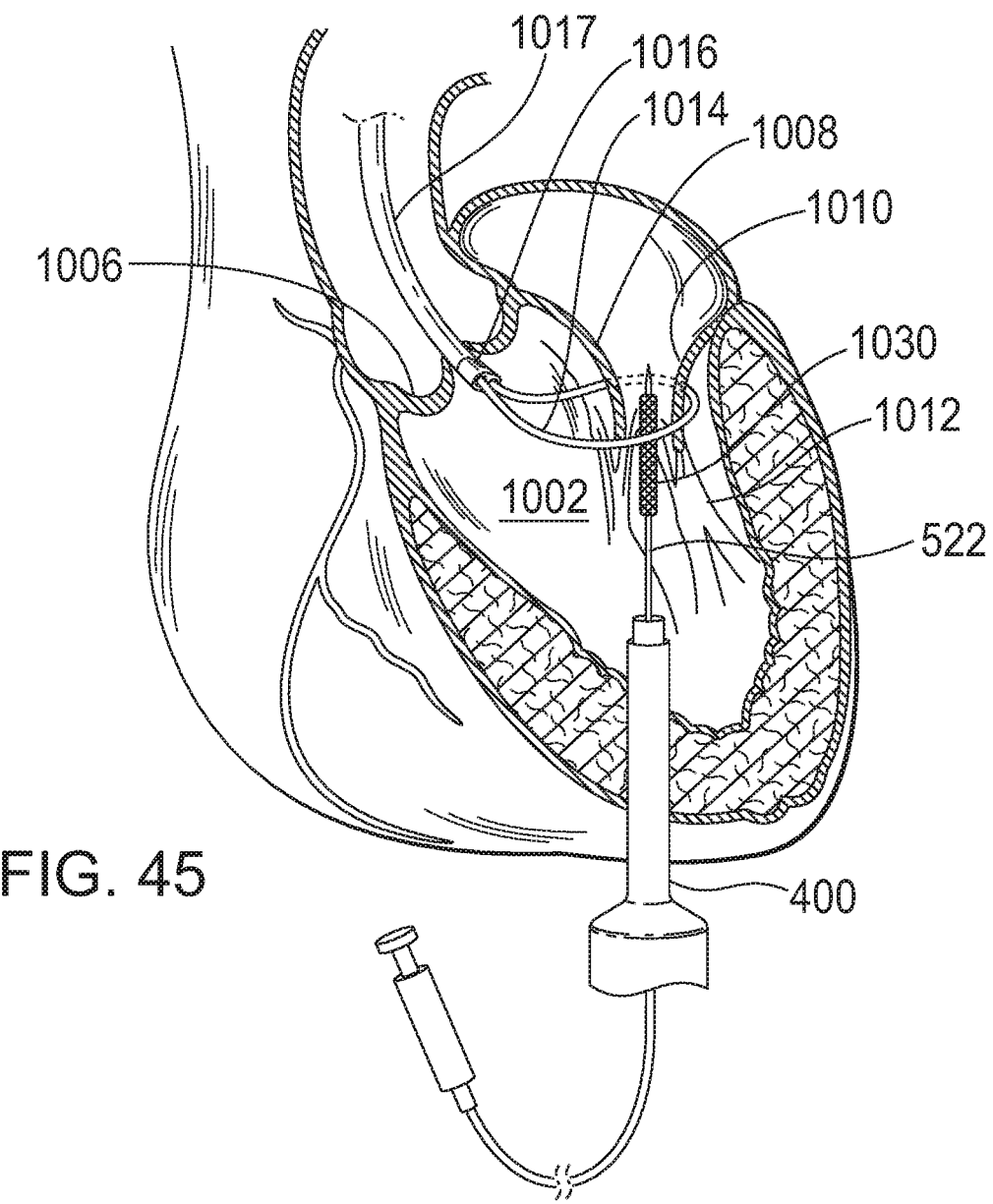
FIG. 45 is a cross-sectional view of a patient's heart illustrating the use of a support band that at least partially surrounds the native leaflets in combination with an expandable THV.

As shown in FIGS. 43 and 44, as distal end 1022 moves into receiving area 1020, locking member 1016 secures distal end 1022 to locking member 1016, thereby forming a support band that generally encircles the native leaflets (FIG. 45). FIG. 43 illustrates the formation of the support band when support member 1014 is coupled or secured to locking member 1016 at both ends (e.g., at both the proximal end 1018 and distal end 1022).

Referring to FIG. 44, an exemplary embodiment for securing locking member 1016 to distal end 1022 of support member 1014 is illustrated. As discussed above, proximal end 1018 can be secured to an inner surface 1024 of locking member 1016 by any suitable chemical or mechanical means. In the embodiment shown in FIG. 44, distal end 1022 is mechanically secured to receiving area 1020. Receiving area 1020 comprises a securing member 1026 that allows distal end 1022 to move into receiving area 1020, but restricts it from moving back out of receiving area 1020. In particular, securing member 1026 comprises one or more tab members that are biased inward, and distal end 1022 comprises a nose cone that has an indentation or groove 1028 that can receive the biased tab member as shown in FIG. 44. The nose cone 1022 preferably has a tapered end so that biased tab member 1026 will slide more easily along an outer surface of nose cone 1022 as it moves into receiving area 1020. When biased tab member 1026 reaches groove 1028, biased tab member 1026 extends into groove 1028 and restricts nose cone 1022 from moving back (proximally) out of locking member 1016. Tab members 1026 can be formed of any suitable material. In a preferred embodiment, tab members 1026 comprise NiTi spring tabs.

It should be noted that as discussed above, proximal end 1018 can be secured to locking member 1016 after support member 1014 is introduced into the body of the patient. If proximal end 1018 is configured for in situ securement to locking member 1016, it may be desirable to provide a securing member such as that described above and shown in FIG. 44 for securing the proximal end 1018 to locking member 1016.

As shown in FIG. 45, once support member 1014 has encircled the native leaflets and both ends of support member 1014 are coupled to locking member 1016, a THV 1030 can be delivered at least partially through or inside of the support band formed by the support member 1014 and locking member 1016 and deployed. The THV 1030 shown in FIG. 45 is a balloon expandable THV delivered transapically to the mitral valve annulus via an introducer sheath 400 and balloon delivery catheter 522, as discussed in more detail in other embodiments herein. However, it should be understood that other THV devices and delivery methods can be used to deploy a THV inside the support band. For example, THV 1030 can be a self-expanding prosthetic device and/or the THV 1030 can be delivered percutaneously to the mitral valve annulus.

Figure 46:
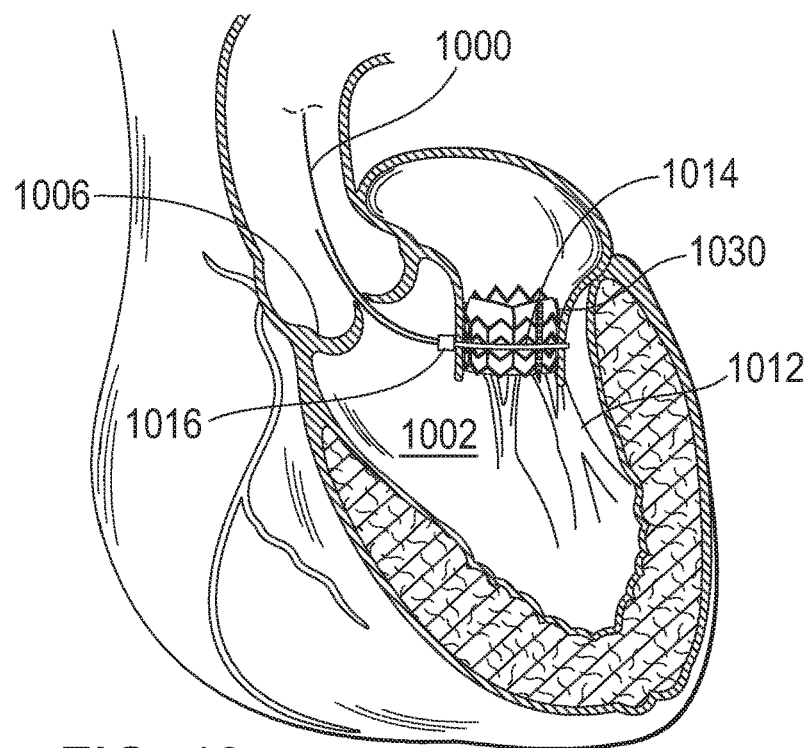
FIG. 46 is a cross-sectional view of a patient's heart illustrating the use of a support band that at least partially surrounds the native leaflets, shown with a THV expanded with the support band.
Figure 47:
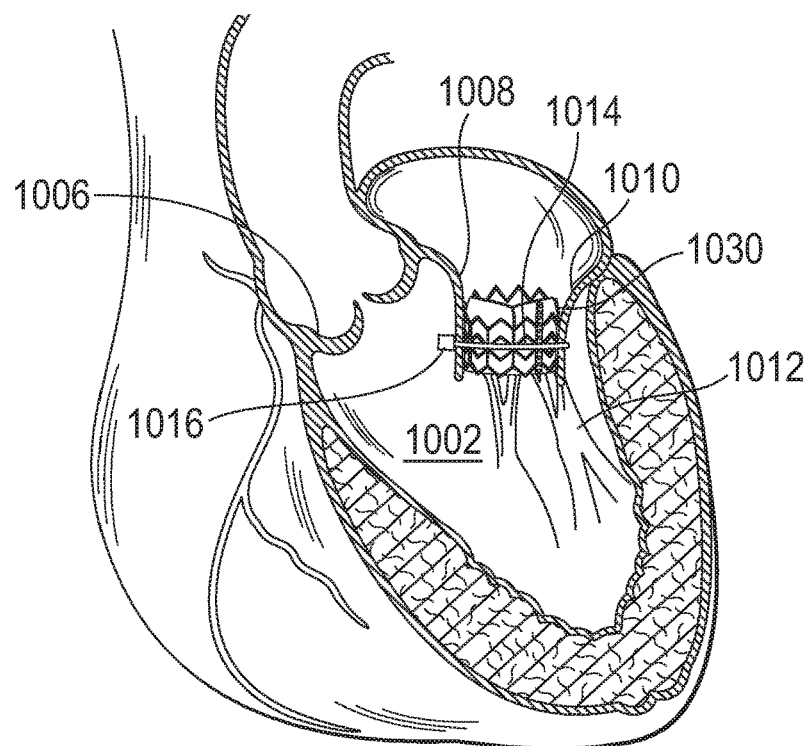
FIG. 47 is a cross-sectional view of the support band and THV shown in FIG. 46, with the guide wire removed.

As shown in FIG. 46, once THV 1030 is expanded in the mitral valve annulus and the native leaflets are captured between an outside surface of the THV 1030 and an inner surface of the support band, the THV delivery system (e.g., introducer sheath 400 and/or balloon delivery catheter 522) can be withdrawn from the left ventricle 1002. In addition, if it has not already been withdrawn, pushing member 1017 can also be withdrawn from the left ventricle 1022 at this time. Accordingly, as shown in FIG. 46, only THV 1030, the support band (i.e., support member 1014 and locking member 1016) and the guidewire 1000 remain in the heart of the patient. As shown in FIG. 47, guidewire 1000 can be withdrawn from the left ventricle (and the patient), leaving the THV 1030 and support band coupled to the native leaflets of the patient.

To facilitate the entrapment of the leaflets, the inside diameter of the support band (e.g., support member locked in a closed ring shape by the locking member) is preferably the same size or slightly smaller than the final outer diameter of the THV. By providing a support band of such a size, a relatively high retention force can be achieved between the support band and the THV upon deployment (expansion) of the THV. Also, tissue can grow around and into the support band further enhancing the retention of the THV. In addition, such an arrangement causes the leaflets to function as a sealing member between the THV and the support band, which can help reduce the occurrence of paravalvular leaks. Moreover, once the support band is secured in place by the outward force of the THV, the band tends to apply tension to the native leaflets, thereby pulling inward on the native annulus. Consequently, this arrangement helps treat the underlying condition by preventing or at least minimizing dilation of the native annulus. This is in contrast to known prosthetic devices that push outward on the native annulus and can, in some situations, exacerbate the underlying condition.

It should be understood that certain steps of the method described above and shown in FIGS. 40-47 can vary in the order in which they are performed. For example, if desired, the pushing member and/or the guidewire can be withdrawn from the patient before expansion of the THV. Such variations will be readily apparent to one of ordinary skill in the art.

Figure 48:
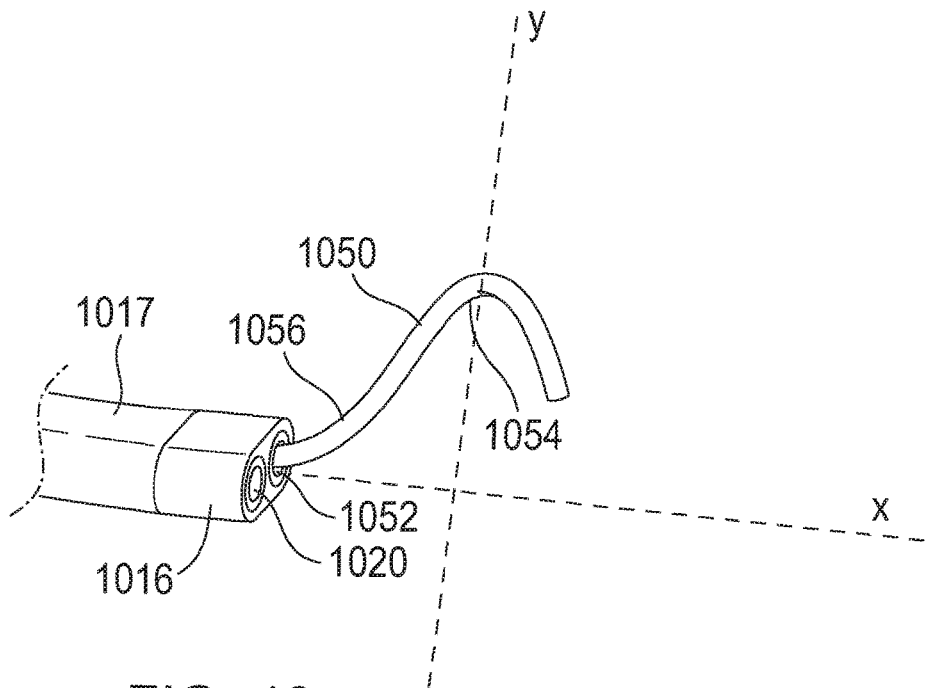
FIG. 48 is a view of a precurved catheter exiting a distal end of a delivery catheter (e.g., a pushing member and a locking member combination).
Figure 49:
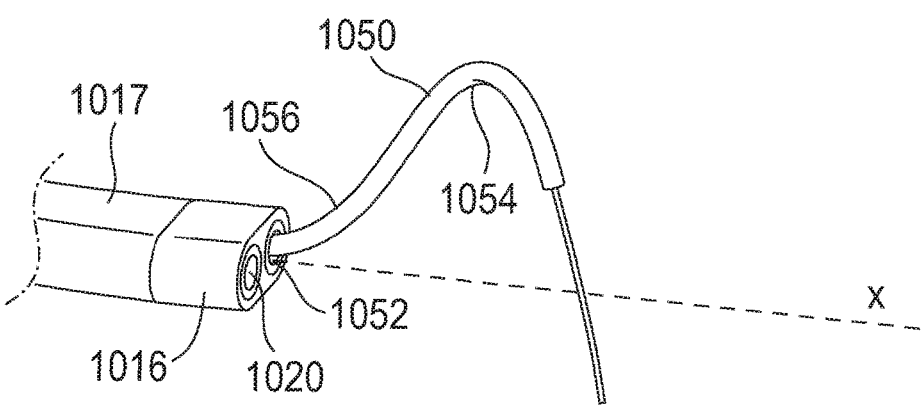
FIG. 49 is a view of the device of FIG. 48, shown with a precurved guide exiting a distal end of the precurved catheter shown in FIG. 48.

FIGS. 48-54 illustrate systems and methods delivering a support band around the native leaflets of a valve (e.g., the mitral valve). As discussed above in the embodiments shown in FIGS. 40-47, a support member can be delivered over a guidewire that at least partially encircles the native leaflets. FIG. 48 illustrates a delivery system that can more easily deliver the guidewire around the native leaflets. An inner, guidewire delivery catheter 1050 can extend through a main delivery catheter. The delivery catheter can be any structure that has a lumen capable of receiving catheter 1050. In FIG. 48, the delivery catheter comprises the combination of the pushing member 1017 and locking member 1016. Catheter 1050 extends through a first opening 1052 in locking member 1016 to exit the delivery catheter.

As noted above, a proximal end 1018 of support member 1014 can be secured to locking member 1016 in situ. In FIG. 48, the support member has not yet been delivered to locking member 1016, which permits catheter 1050 to be advanced through pusher member 1017 and a first opening 1052 in locking member 1016. As described below, catheter 1050 helps guidewire 1000 form a loop around the native leaflets prior to delivering support member 1014. After the guidewire is positioned around the native leaflets as described below, support member can be advanced through pusher member 1017 and its proximal end 1018 can be secured to locking member 1016 at or within opening 1052.

Alternatively, instead of passing through pusher member 1017 and locking member 1016, catheter 1050 can be delivered through another larger catheter. Thus, a larger catheter would replace the pushing member 1017 and locking member 1016 shown in FIG. 48. Once the guidewire is delivered through catheter 1050 and positioned around the native leaflets as described below, catheter 1050 and the larger delivery catheter can be withdrawn. Then, locking member 1016 and support member 1014 can be delivered over the guidewire in the manner described with respect to FIGS. 40-47.

Accordingly, catheter 1050 can be delivered through the pushing member/locking member or through a larger catheter, both of which are collectively referred to herein as the delivery catheter.

Figure 50:
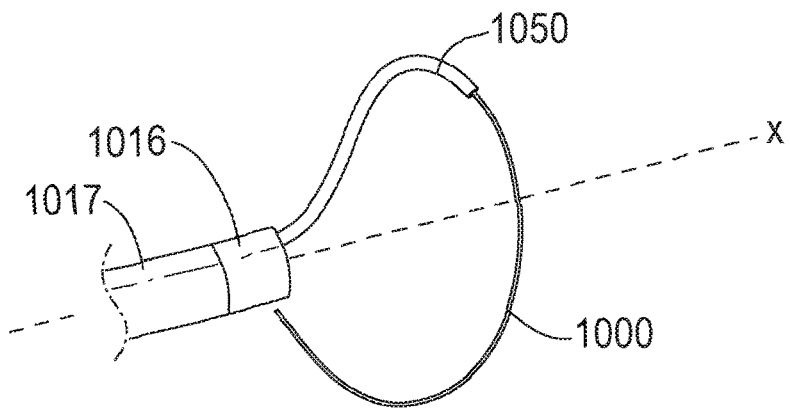
FIG. 50 illustrates the precurved guide wire of FIG. 49 further advancing out of the precurved catheter.
Figure 51:
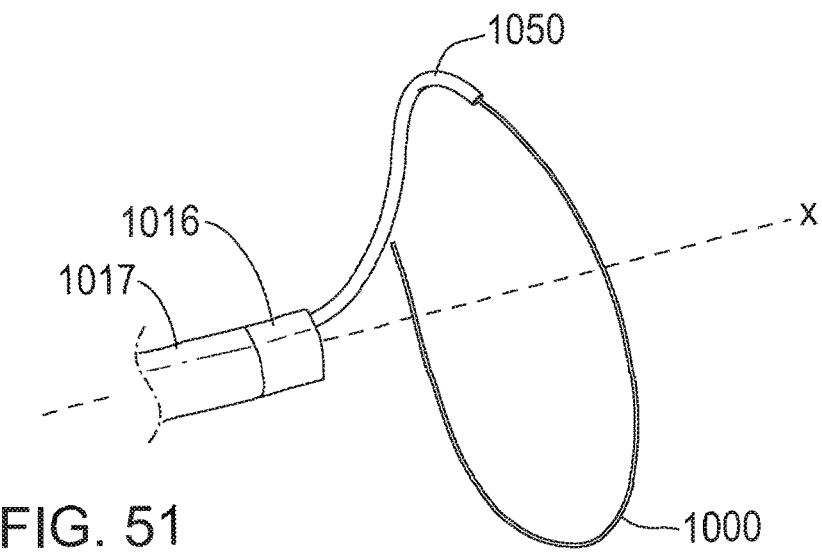
FIG. 51 illustrates the precurved guide wire of FIG. 50 further advancing out of the precurved catheter.
Figure 52:
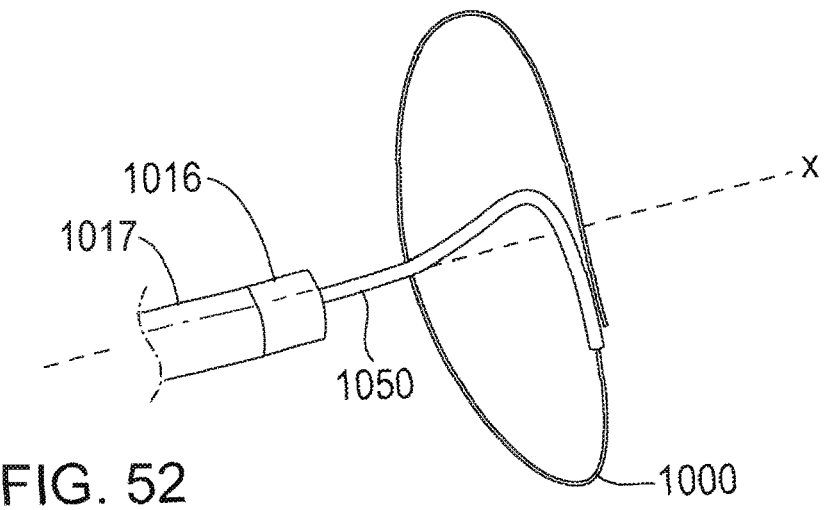
FIG. 52 illustrates the precurved guide wire of FIG. 51 further advancing out of the precurved catheter, and forming a generally circular loop.

Catheter 1050 can be used to facilitate delivery of guidewire 1000 around the native leaflets as follows. Catheter 1050 can be deformable and preshaped (e.g., heat set or formed of a shape memory material) to a specific curve. Thus, as catheter 1050 is pushed out of first opening 1052, it begins to conform to the predetermined curve. As shown in FIG. 48, catheter 1050 preferably is configured to have at least two different bending curves. A first predetermined curve 1054 (distal bending curve) of the catheter 1050 can be, for example, at an angle of about 60-180 degrees along a longitudinal axis (x-axis) of the delivery catheter (e.g., a larger catheter or pushing member 1017). A second predetermined curve 1056 (proximal bending curve) can also be of about 60-180 degrees. However, the first and second predetermined curves are preferably not in the same plane. In a preferred embodiment, the first predetermined curve 1064 is in a plane that is generally perpendicular to the axis of the delivery catheter (e.g., perpendicular to the longitudinal axis of the delivery catheter). Generally perpendicular means an angle that is between about 70 and 110 degrees from the axis of the delivery catheter. Thus, as shown in FIGS. 50-52, when a precurved guidewire 1000 is delivered out a distal end of catheter 1050, guidewire 1000 forms a loop that is also generally perpendicular to the longitudinal axis (x-axis) of the delivery catheter.

Figure 53:
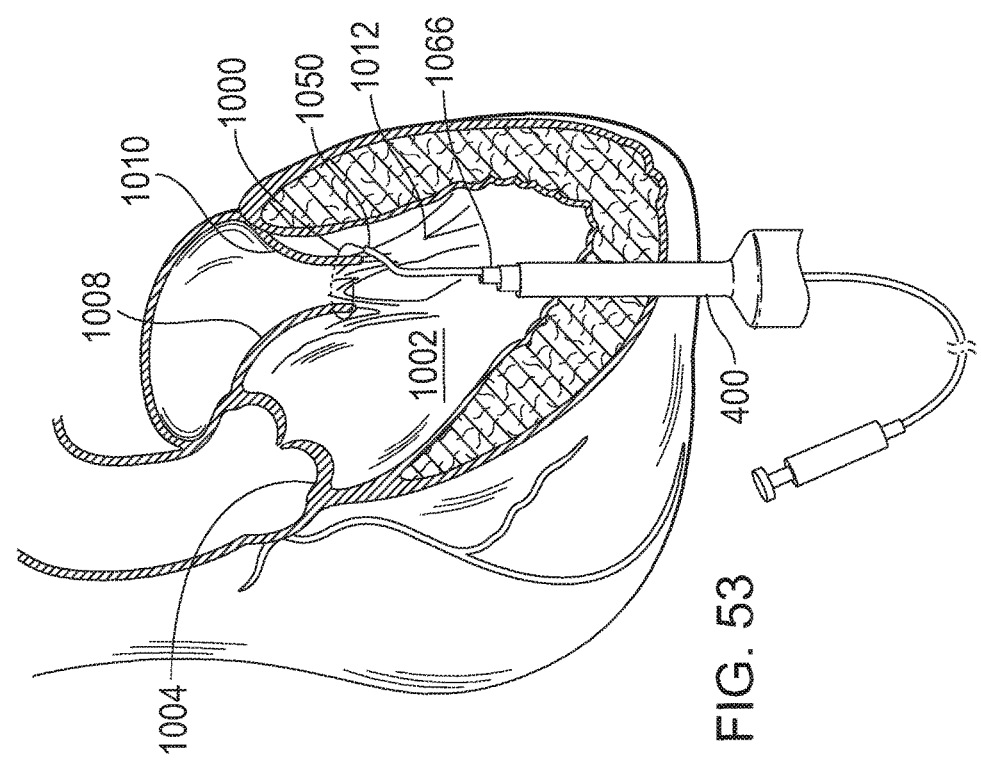
FIG. 53 is a cross-sectional view of a patient's heart illustrating the delivery of a precurved guide wire at least partially around the native leaflets.

Guidewire 1000 can be preformed to have a generally circular shape that has a diameter that is large enough to encircle the native leaflets of the mitral valve. Thus, as shown in FIG. 52, as guidewire 1000 exits catheter 1050, it tracks a circular path until it loops back over itself. Referring to FIG. 53, such an arrangement can facilitate the encircling of the leaflets by guidewire 1000.

In operation, when using a transapical approach as shown in FIG. 53, for example, the precurved catheter 1050 can be delivered through an introducer sheath 400 and a delivery catheter 1066. As catheter 1050 exits the delivery catheter 1066 it curves away from the longitudinal axis of the delivery catheter and approaches a position on the outflow side of the native leaflets of the mitral valve. Precurved guidewire 1000 can then be pushed distally out of catheter 1050. Because precurved guidewire 1000 natural condition is a generally circular shape, guidewire 1000 begins to encircle the native leaflets as it advances out of catheter 1050.

Figure 54:
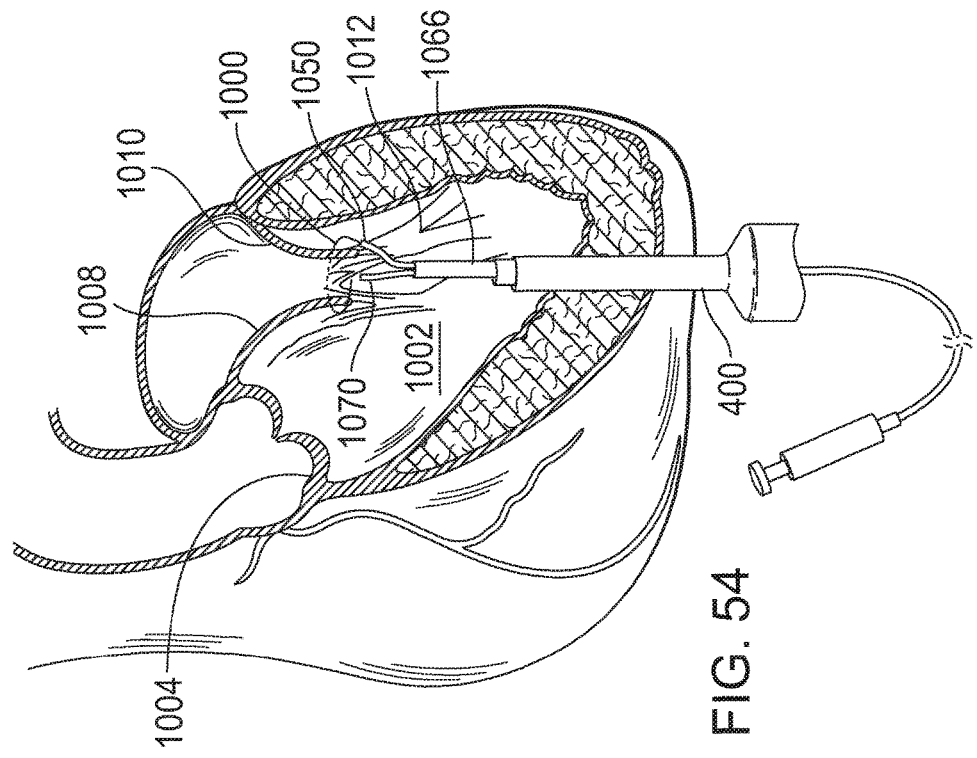
FIG. 54 is a cross-sectional view of a patient's heart illustrating the delivery of a precurved guide wire at least partially around the native leaflets, and a snare catheter to capture the distal end of the precurved guide wire.
Figure 55:
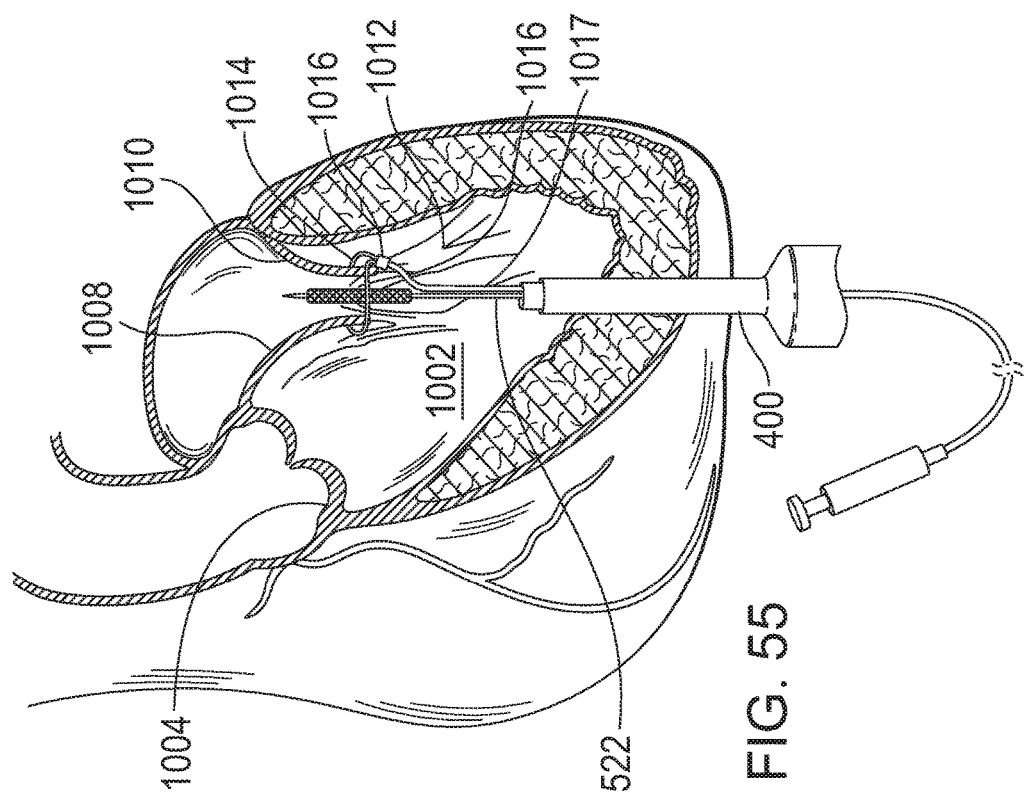
FIG. 55 is a cross-sectional view of a patient's heart illustrating a support member delivered over the precurved guide wire shown in FIG. 54 and locked into a support band.

As shown in FIG. 54, once guidewire 1000 generally surrounds the native leaflets, a snare catheter 1070 can be passed through the delivery catheter 1066 (or through receiving area 1020 as shown in FIG. 48, if the delivery catheter includes the locking member) to capture the end of guidewire 1000 and bring it back to second opening 1066. Then, support member 1014 can be delivered over the guidewire 1000 as described above with respect to FIGS. 40-47. After the support member is locked into the form of the support band, a THV can be delivered as shown in FIG. 55 (and as described in other embodiments) to capture or otherwise pinch the native leaflets between the support band and the THV.

Figure 56:
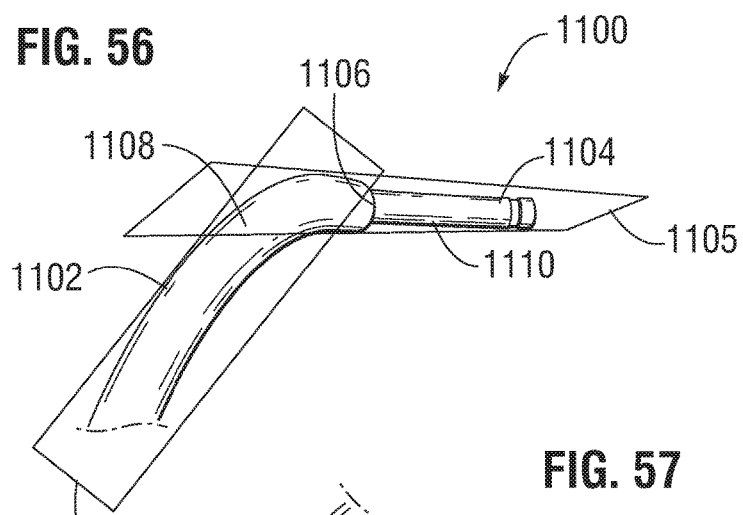
FIG. 56 illustrates a delivery system for delivering a support member at least partially around native leaflets of a heart valve.

FIG. 56 illustrates another delivery system for delivering a support band around the native leaflets of a valve (e.g., the mitral valve). Delivery system 1100 comprises a first, steerable catheter 1102 and a second pre-shaped catheter 1104 that can be advanced from a distal end 1106 of catheter 1102. Catheter 1104 can be pre-shaped (e.g., heat set or formed of a shape memory material) to a specific curve. Thus, as shown in FIG. 56, catheter 1102 can be curved to form a first bend 1108 and catheter 1104 can extend from catheter 1102 and form a second bend 1110. As shown in FIG. 56, catheter 1102 forms a first plane 1103 and catheter 1104 forms a second plane 1105 of an orientation different from that of first plane 1103.

The orientations of first and second catheters 1102, 1104 can be generally fixed by providing an orientation fixing element (e.g., an interlocking or interconnecting pathway, such as a key-way) between the two catheters. Such an orientation fixing elements can maintain the relative orientations of first and second catheters 1102, 1104 to ensure that the relative planes 1103, 1105 of the catheters are appropriately oriented for placement in the vicinity of the mitral valve.

Figure 57:
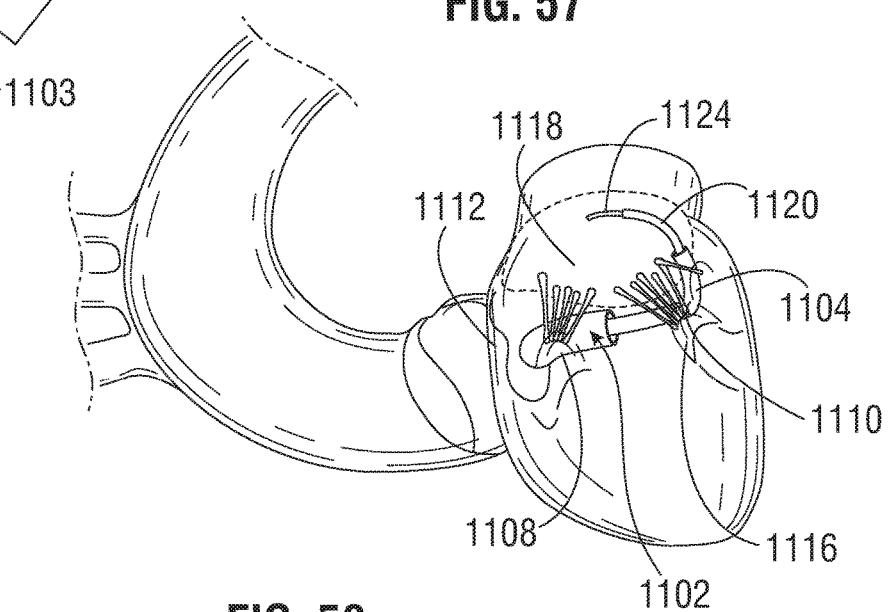
FIG. 57 illustrates a delivery system for delivering a support member at least partially around native leaflets of a heart valve.

Referring to FIG. 57, catheter 1102 can be advanced through an aortic valve 1112 so that a distal end 1114 of catheter 1104 is positioned adjacent the chordae tendineae 1116 and/or leaflets of a mitral valve 1118. Once the distal end of catheter 1104 is positioned adjacent the chordae tendineae 1116 of mitral valve 1118, a guidewire can be passed around at least some of the chordae tendineae 116 as described above (e.g., generally forming a loop around the native leaflets as shown in FIG. 42A).

To further define a path encircling the chordae tendineae 1116 of mitral valve 1118, a third catheter 1120 can extend from distal end 1114 of catheter 1104. Catheter 1120 can be configured to extend from distal end 1114 so that a distal end 1122 of catheter 1120 is generally aligned and directed to define a plane that is co-planar with the plane of the mitral annulus. As shown in FIG. 57, in this manner, a guidewire 1124 can be delivered through catheter 1120 until guidewire 1124 substantially encircles the chordae tendineae 1116 of mitral valve 1118. To further facilitate the encircling of the chordae tendineae 1116 of mitral valve 1118, catheter 1120 preferably is pre-shaped (e.g., heat set or formed of a shape memory material) to a curvature that generally corresponds to a curvature of a circle sized to surround the chordae tendineae 1116 of mitral valve 1118.

Thus, guidewire 1124 can be advanced through respective catheters 1102, 1104, 1120 to generally form a loop around the chordae tendineae 1116 of mitral valve 1118 in a manner similar to that shown in FIG. 52. Once guidewire 1124 is generally formed into a loop around the chordae tendineae 1116 of mitral valve 1118, guidewire 1124 can then be captured by a snare catheter (as described in more detail, for example, with respect to FIG. 54). After snaring guidewire 1124, guidewire 1124 can then be advanced back into one or more of catheters 1102, 1104, 1120 to a desired position for advancement of a support member over guidewire 1124. In one embodiment, guidewire 1124 can be advanced back entirely through one or more catheters to an introducer sheath.

After guidewire 1124 is in the desired position (e.g., with both ends accessible to a physician and with a portion of guidewire 1124 substantially encircling the chordae tendineae 1116), a support member can be advanced over guidewire 1124 as described above with respect to FIGS. 42-47.

Figure 58:
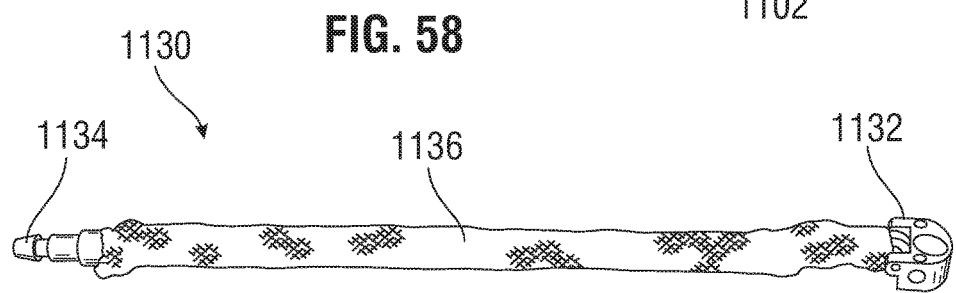
FIG. 58 illustrates a support member for at least partially surrounding native leaflets of a heart valve.

FIG. 58 illustrates another embodiment of a support member 1130 that can be advanced around the chordae tendineae 1116 of mitral valve 1118 and linked end-to-end to form a support band. Support member 1130 can comprise a locking member 1132 (e.g., a locker socket), a distal end 1134 that is configured to be coupled to locking member 1032, and a longitudinally extending linking portion 1136. Linking portion 1136 can comprise a braided member that has a cover or sheath generally surrounding the braided member. The cover can be formed of various materials, including for example, synthetic fibers such as polyethylene terephthalate (PET).

Figure 59:
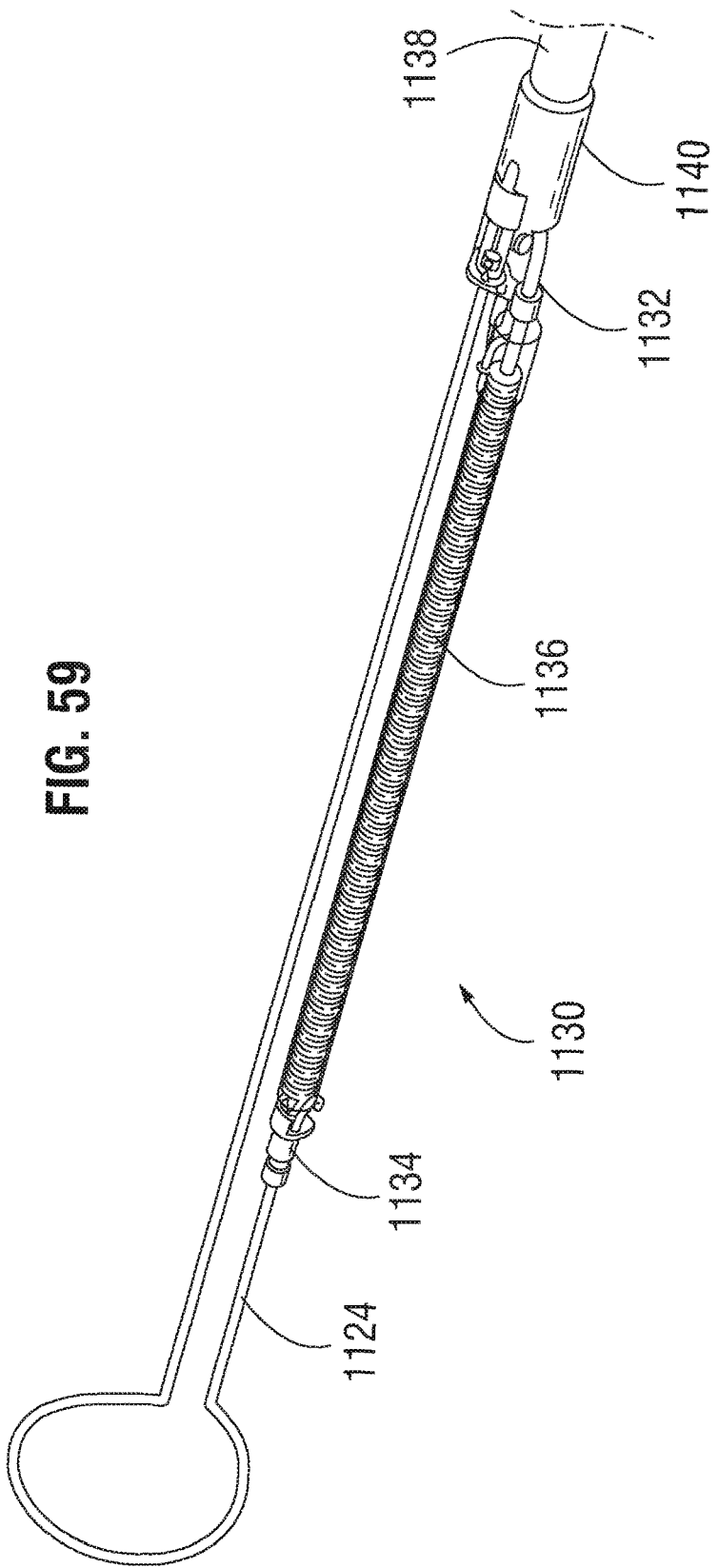
FIG. 59 illustrates a delivery system for delivering a support member at least partially around native leaflets of a heart valve.
Figure 60:
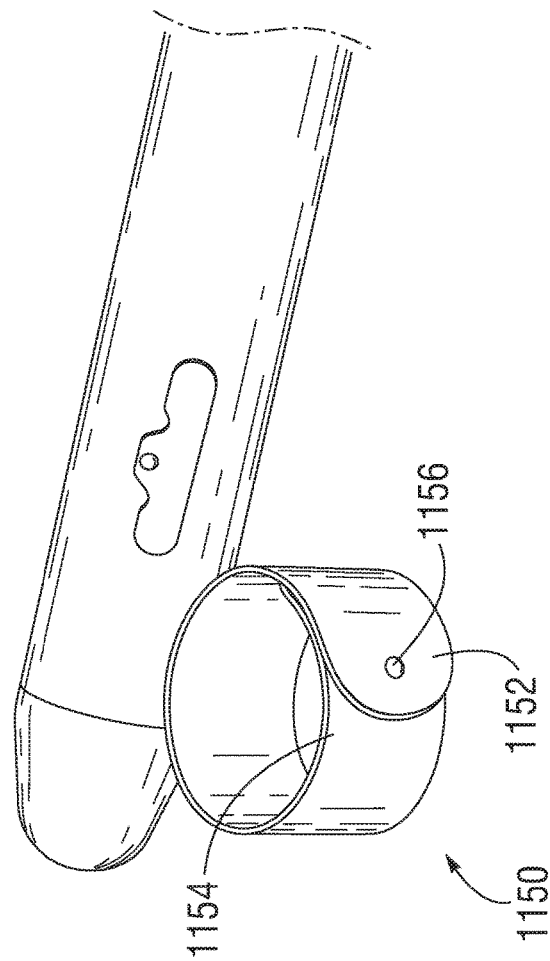
FIG. 60 illustrates the delivery system of FIG. 59 as it forms a closed loop support band.

FIGS. 59 and 60 illustrates support member 1130 being delivered over guidewire 1124. A pushing member 1138 can be positioned proximal to locking member 1132 to push and/or direct support member over guidewire 1124. Pushing member 1138 can also comprise a retaining member 1140 releasably coupled to locking member 1132 of support member 1130 to engage support member 1130. As shown in FIG. 60, support member 1130 can be advanced over guidewire 1124 (e.g., by moving pushing member 1138 distally along guidewire 1124) until distal end 1134 advances back and into a portion of locking member 1132 to form a support band around the chordae tendineae 1116 of mitral valve 1118. As described above with respect to FIG. 43, distal end 1134 can be configured to be received within a portion of locking member 1132, thereby securing distal end 1134 to locking member 1132 and forming a support band.

Figure 61:
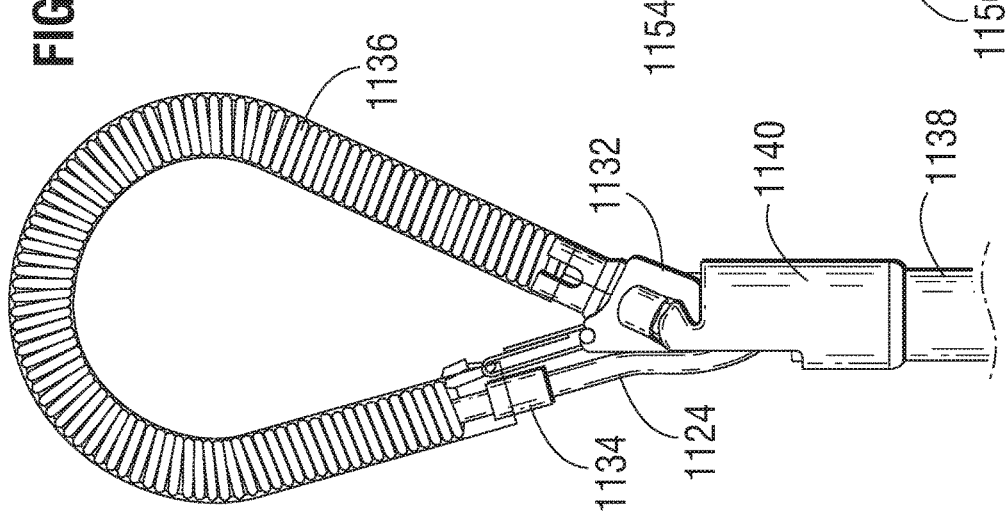
FIG. 61 illustrates another embodiment of a support member for at least partially surrounding native leaflets of a heart valve

FIG. 61 illustrates another embodiment of a support member 1150 that can be advanced around the chordae tendineae 1116 of mitral valve 1118 to form a support band. Support member 1150 is a coiled, expandable ring-shaped element that can provide radial rigidity in the vicinity of a mitral valve (e.g., valve leaflets and chordae region) to improve fixation of a prosthetic valve deployed within the annulus of a mitral valve.

Support member 1150 has a first end 1152 and a second end 1154. FIG. 61 illustrates an opening 1156 in first end 1152 that is positioned to engage with an extending portion 1158 (e.g., a bump or raised portion) on the delivery device to help retain support member 1150 within the delivery device until fully deployed. If desired, a locking element can be provided to secure first and second ends 1152, 1154 together. For example, in other embodiments, an extending portion (e.g., a bump or raised portion) can be provided on second end 1154 to allow first and second ends 1152, 1154 to be coupled together.

FIG. 62 illustrates a delivery device 1160 for retaining and delivering support member 1150. Delivery device 1160 can comprise a main body 1162 that has a port 1164 near a distal end portion 1166. FIG. 63 illustrates main body 1162 with support member 1150 positioned in the vicinity of port 1164 for deployment.

A retaining member (e.g., an extending portion) 1168 can be provided adjacent to side port 1164 to hold one end of support member 1150 within delivery device 1160 prior to and during deployment. As shown in FIG. 62, retaining member can comprise a spring member 1168 that is biased to extend into opening 1156 to secure one end of support member 1150 within main body 1162 until it is desirable to fully release support member 1150 from delivery device 1160.

A deployment shaft 1170 can be coupled to a deployment knob or handle 1172 to allow for rotation of deployment shaft 1170 relative to main body 1162. In operation, delivery device 1160 can be delivered transapically into the vicinity of the mitral valve and support member 1150 can be released from main body 1162 as shown in FIGS. 64A-64E.

Figure 64A:
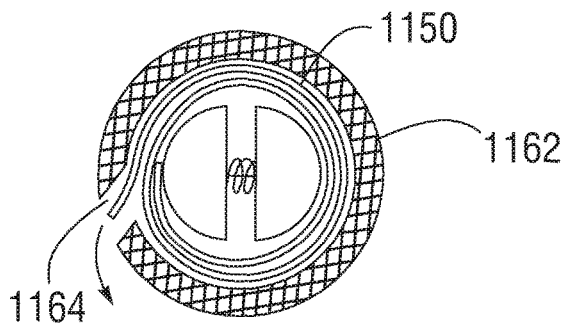
FIGS. 64A-64E illustrate the deployment of a support member to at least partially surround native leaflets of a heart valve.
Figure 64B:
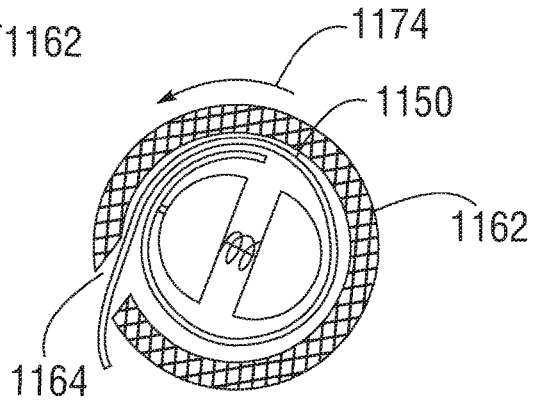
Figure 64C:
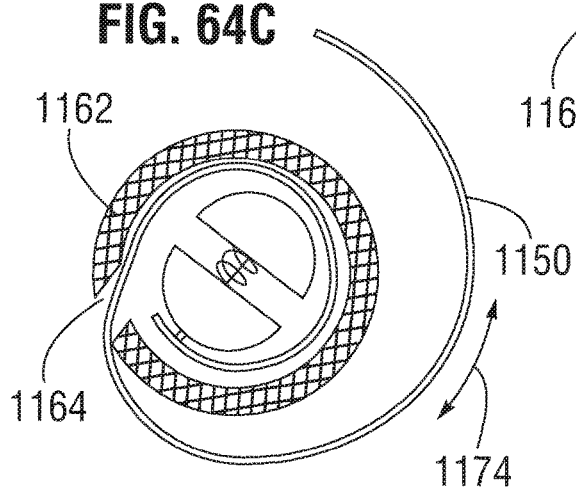
Figure 64D:
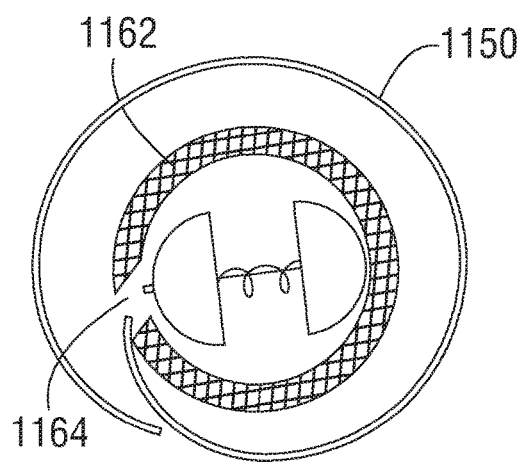
Figure 64E:
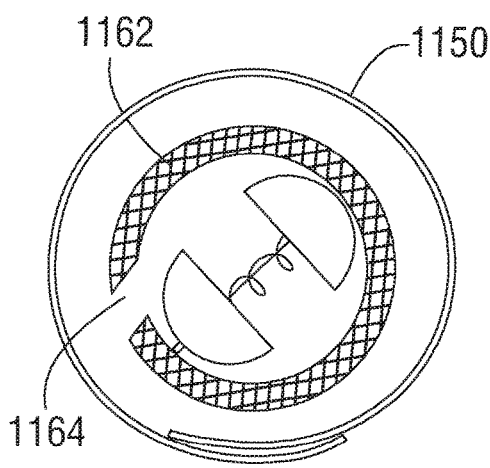

FIGS. 64A-64E illustrate cross-sectional views of support member 1150 and delivery system 1160 as support member 1150 is deployed. As shown in FIG. 64A, support member 1150 is coiled or rolled up within main body 1162 in the vicinity of port 1164, with first end 1152 of support member 1150 being generally aligned with port 1164. By rotating deployment shaft 1170 in the direction shown by arrow 1174, first end 1152 of support member 1150 extends out of port 1164 to begin delivery of support band 1150 around the mitral valve leaflets. FIGS. 64B-64E illustrate the advancement of support band 1150 out of port 1164 until support member 1150 is fully deployed to form a support band that extends substantially around the mitral valve leaflets. For clarity, the mitral valve leaflets are not illustrated in FIGS. 64A-64E.

Figure 65:
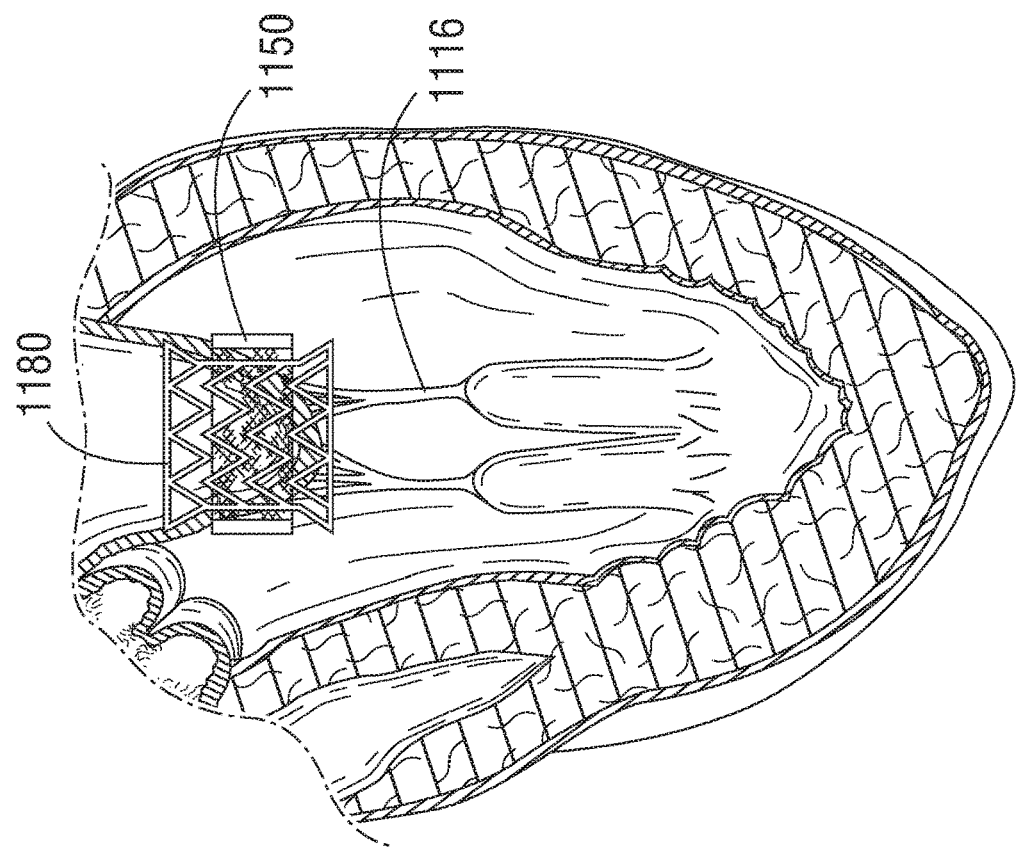
FIG. 65 illustrates a prosthetic heart valve deployed within a support member that at least partially surrounds native leaflets of a heart valve.

Once support member 1150 is fully deployed from delivery device 1160, a prosthetic heart valve 1180 can be deployed within support member 1150, as described in other embodiments herein. FIG. 65 illustrates prosthetic heart valve 1180 expanded within a fully deployed support member 1150.

Figure 66:
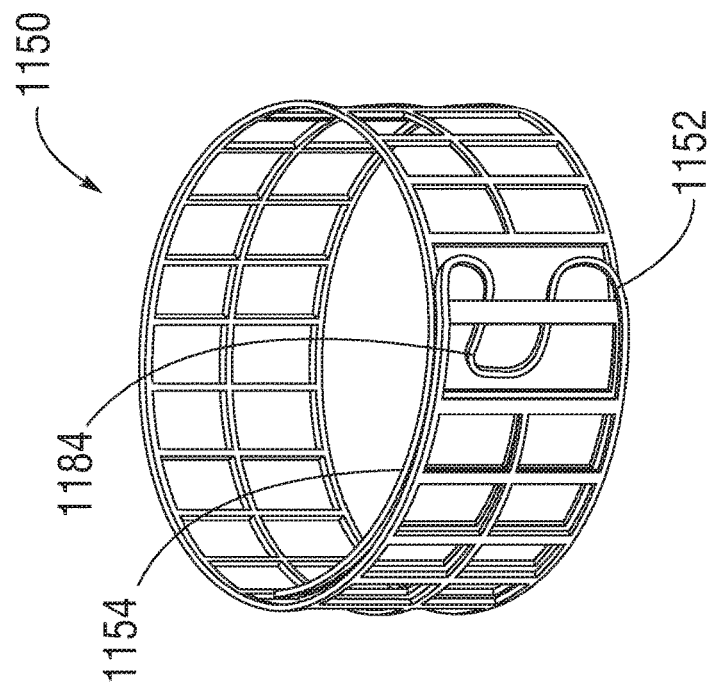
FIG. 66 illustrates an open-frame configuration of a support member.

Support member 1150 can be formed of various materials. For example, support member 1150 can be formed of polymers or metals (e.g., Nitinol). Moreover, in addition to comprising a coiled sheet of material as shown in FIG. 61, support member 1150 can be formed with an open frame configuration as shown in FIG. 66. The open frame configuration shown in FIG. 66 can be formed, for example, by laser cutting a flat sheet of Nitinol or other materials. In addition, as shown in FIG. 66, a latch or locking member 1184 can be provided on a first and/or second end 1152, 1154 to engage with the opposing end or side of support member 1150 to secure first and second ends 1152, 1154 to one another.

Although the description above describes a precurved catheter and a precurved guidewire, it should be understood that other structures can be used with similar results. For example, rather than delivering a guidewire to receive a support member (FIGS. 53-55), it may be desirable to deliver a support band itself using a precurved catheter and a precurved support member delivered through the precurved catheter. Similar to guidewire 1000 shown in FIGS. 53-55, the support member can be precurved so that it forms a circular shape and at least partially surrounds the native leaflets. A securing mechanism can then be delivered to secure two ends of the support member in various ways. For example, a snare catheter 1070 (FIG. 54) can capture a distal end of the support member and a securing mechanism can be delivered over both ends of the support member in the same general manner as that described and shown above with respect to FIGS. 23-24.

Depending on the anatomical approach to the mitral valve various other precurved configurations may be desirable. For example, for the transapical approach shown in FIGS. 53-55 it is desirable that the loop of the guidewire (or other curving member) is approximately perpendicular to the axis of the delivery catheter. Other approaches such as the approach through the aortic annulus may require other angles between the delivery system and the plane formed by the loop of guidewire (or other curving member).

Other methods of delivering a support band and THV to the mitral valve or any other heart valve are also possible. For example, in certain embodiments, the support band and the THV are delivered surgically to the desired heart valve (e.g., in an open-heart surgical procedure). Furthermore, in certain embodiments in which the support band and THV are delivered surgically, non-compressible THVs are used.

Having illustrated and described the principles of the disclosed technology, it will be apparent to those skilled in the art that the disclosed embodiments can be modified in arrangement and detail without departing from such principles. In view of the many possible embodiments to which the principles of the disclosed technologies can be applied, it should be recognized that the illustrated embodiments are only preferred examples of the technologies and should not be taken as limiting the scope of the invention. Rather, the scope of the invention is defined by the following claims and their equivalents. We therefore claim all that comes within the scope and spirit of these claims.

What is claimed is:

1. A method comprising:
    advancing a delivery catheter into a body of a patient;
    advancing a cord distally through the delivery catheter such that a distal end portion of the cord extends beyond a distal end of the delivery catheter and the cord curves around tissue in the heart; and
    capturing the distal end portion of the cord with a snare;
    pulling the snare and the distal end portion of the cord so as to form a loop around the tissue in the heart; and
    pulling the snare and the distal end portion of the cord proximally back through the delivery catheter.

2. The method of claim 1, further comprising advancing a support member over the cord such that the support member curves around tissue in the heart.

3. The method of claim 2, further comprising pushing a pusher member over the cord to push the support member over the cord and around the tissue in the heart.

4. The method of claim 2, wherein the support member comprises a tubular braided cover.

5. A method comprising:
    advancing a delivery catheter into a body of a patient;
    advancing a cord distally through the delivery catheter such that a distal end portion of the cord extends beyond a distal end of the delivery catheter and the cord curves around tissue in the heart;
    advancing a snare out of the delivery catheter; and
    capturing the distal end portion of the cord with the snare.

6. A method comprising:
    advancing a delivery catheter into a body of a patient;
    advancing a cord distally through the delivery catheter such that a distal end portion of the cord extends beyond a distal end of the delivery catheter and the cord curves around tissue in the heart; and
    capturing the distal end portion of the cord with a snare;
    wherein the cord comprises a precurved guidewire configured to curve around tissue in the heart when the precurved guidewire is advanced beyond the distal end of the delivery catheter.

7. A method comprising:
    advancing a delivery catheter into a body of a patient;
    advancing a cord distally through the delivery catheter such that a distal end portion of the cord extends beyond a distal end of the delivery catheter and the cord curves around tissue in the heart; and
    capturing the distal end portion of the cord with a snare;
    wherein advancing the cord distally through the delivery catheter comprises:
    advancing a precurved catheter out of the delivery catheter, wherein the precurved catheter is configured to bend in a predetermined manner when it is advanced out of the delivery catheter; and
    advancing the cord out of the precurved catheter.

8. A method comprising:
    advancing a delivery catheter into a body of a patient;
    advancing a cord distally through the delivery catheter such that a distal end portion of the cord extends beyond a distal end of the delivery catheter and the cord curves around tissue in the heart; and
    capturing the distal end portion of the cord with a snare; and
    pulling the snare and the distal end portion of the cord so as to form a loop around the tissue in the heart;
    wherein the cord forms a loop around the native mitral valve leaflets, and the method further comprises delivering a prosthetic heart valve to a position between the native leaflets and expanding the prosthetic heart valve to capture the native leaflets between the cord and the prosthetic heart valve.

9. A system comprising:
    a delivery catheter having a distal end;
    a cord configured to extend distally through the delivery catheter in a first direction beyond the distal end of the delivery catheter; a support member comprising an internal lumen for receiving the cord; an elongated pusher member configured to push the support member over the cord; and a snare configured to capture a distal end portion of the cord and pull the distal end portion of the cord in a second direction so as to form a loop around the tissue in the heart;

wherein the snare is further configured to pull the distal end portion of the cord in the second direction back through the delivery catheter.

10. A system comprising:

a delivery catheter having a distal end;

a cord configured to extend distally through the delivery catheter and beyond the distal end of the delivery catheter such that the cord can curve around tissue in the heart to form at least a partial loop around the tissue in the heart;

a support member having a lumen for receiving the cord, the cord being configured to support the support member adjacent the tissue in the heart; an elongated pusher member configured to push the support member over the cord; and a snare configured to capture a distal end portion of the cord;

wherein the snare is further configured to pull the distal end portion of the cord back through the delivery catheter.

11. A system comprising:

a delivery catheter having a distal end;

a cord configured to extend distally through the delivery catheter and beyond the distal end of the delivery catheter such that the cord can curve around tissue in the heart to form at least a partial loop around the tissue in the heart; and a support member having a lumen for receiving the cord, the cord being configured to support the support member adjacent the tissue in the heart;

wherein the cord comprises a precurved guidewire having a precurved portion that is biased to return to a predetermined curved configuration when it is advanced beyond the distal end of the delivery catheter, the predetermined curved configuration configured to curve around the tissue in the heart to form at least a partial loop around the tissue in the heart.

12. A system comprising:

a delivery catheter having a distal end;

a cord configured to extend distally through the delivery catheter and beyond the distal end of the delivery catheter such that the cord can curve around tissue in the heart to form at least a partial loop around the tissue in the heart; and a support member having a lumen for receiving the cord, the cord being configured to support the support member adjacent the tissue in the heart; and a precurved catheter configured to extend through a lumen of the delivery catheter, the precurved catheter comprising a precurved distal end portion that is biased to return to a predetermined curved configuration when it is advanced out of an opening in the delivery catheter, the precurved catheter comprising a lumen configured to receive the cord such that the cord can be advanced through the precurved catheter and the delivery catheter.

* * * * *